United States Patent
Qiu et al.

(10) Patent No.: US 9,675,632 B2
(45) Date of Patent: Jun. 13, 2017

(54) NUCLEOSIDE AND NUCLEOTIDE DERIVATIVES

(71) Applicant: ENANTA PHARMACEUTICALS, INC., Watertown, MA (US)

(72) Inventors: Yao-Ling Qiu, Andover, MA (US); Xiaowen Peng, Sudbury, MA (US); Xuri Gao, Newton, MA (US); Hui Cao, Belmont, MA (US); Yat Sun Or, Watertown, MA (US)

(73) Assignee: ENANTA PHARMACEUTICALS, INC., Watertown, MA (US)

( * ) Notice: Subject to any disclaimer, the term of this patent is extended or adjusted under 35 U.S.C. 154(b) by 0 days.

(21) Appl. No.: 14/836,157

(22) Filed: Aug. 26, 2015

(65) Prior Publication Data

US 2016/0058783 A1  Mar. 3, 2016

Related U.S. Application Data

(60) Provisional application No. 62/041,971, filed on Aug. 26, 2014, provisional application No. 62/080,827, filed on Nov. 17, 2014.

(51) Int. Cl.

| | |
|---|---|
| *A01N 43/04* | (2006.01) |
| *A61K 31/70* | (2006.01) |
| *A61K 31/7072* | (2006.01) |
| *A61K 45/06* | (2006.01) |
| *C07H 19/06* | (2006.01) |
| *C07H 19/10* | (2006.01) |
| *A61K 31/706* | (2006.01) |
| *A61K 31/7052* | (2006.01) |
| *A61K 31/7068* | (2006.01) |
| *A61K 31/7064* | (2006.01) |

(52) U.S. Cl.
CPC .......... *A61K 31/7072* (2013.01); *A61K 45/06* (2013.01); *C07H 19/06* (2013.01); *C07H 19/10* (2013.01); *A61K 31/706* (2013.01); *A61K 31/7052* (2013.01); *A61K 31/7064* (2013.01); *A61K 31/7068* (2013.01)

(58) Field of Classification Search
None
See application file for complete search history.

(56) References Cited

U.S. PATENT DOCUMENTS

| | | | |
|---|---|---|---|
| 4,336,381 A | 6/1982 | Nagata et al. | |
| 5,041,449 A | 8/1991 | Belleau et al. | |
| 5,047,407 A | 9/1991 | Belleau et al. | |
| 5,210,085 A | 5/1993 | Liotta et al. | |
| 5,814,639 A | 9/1998 | Liotta et al. | |
| 5,914,331 A | 6/1999 | Liotta et al. | |
| 6,812,219 B2 | 11/2004 | LaColla et al. | |
| 6,914,054 B2 | 7/2005 | Sommadossi et al. | |
| 7,247,621 B2 | 7/2007 | Hong et al. | |
| 7,438,920 B1 | 10/2008 | Kim et al. | |
| 7,589,077 B2 | 9/2009 | Kumar et al. | |
| 7,608,600 B2 | 10/2009 | Storer et al. | |
| 7,625,875 B2 | 12/2009 | Gosselin et al. | |
| 7,951,787 B2 | 5/2011 | McGuigan | |

(Continued)

FOREIGN PATENT DOCUMENTS

| | | |
|---|---|---|
| EP | 0337713 | 11/1989 |
| WO | 0132153 A2 | 5/2001 |

(Continued)

OTHER PUBLICATIONS

Hong et al. Tetrahedron Letters (1998), vol. 39, pp. 225-228.*
Jessel et al. Eur. J. Org. Chem. (2011), pp. 1702-1713.*
Li, et al., Synthesis of 2'-C-Branched Nucleosides, Organic Preparations and Procedures International, 42:191-283 (2010).
Hayashi, et al., "Adenallene and cytallene: Acyclic nucleoside analogues that inhibit replication and cytopathic effect of human immunodeficiency virus in vitro," Proceedings of the National Academy of Science, 85:6127-6131,1988.

(Continued)

*Primary Examiner* — Patrick Lewis
(74) *Attorney, Agent, or Firm* — Edgar W. Harlan; Carolyn S. Elmore, Esq.; Elmore Patent Law Gorup, P.C.

(57) ABSTRACT

The present invention discloses compounds of formula (I), or a pharmaceutically acceptable salt thereof:

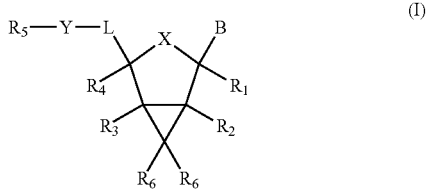

which inhibit, preventing or treating abnormal cellular proliferation and/or a viral infection, particularly by HIV, HCV or HBV. Consequently, the compounds of the present invention interfere with the replication cycle of a virus and are also useful as antiviral agents, or interfere with host cellular biochemical process and are also useful as antiproliferative agents. The present invention further relates to pharmaceutical compositions comprising the aforementioned compounds for administration to a subject suffering from viral infection and/or cell proliferation. The invention also relates to methods of treating a viral infection and/or cell proliferation in a subject by administering a pharmaceutical composition comprising the compounds of the present invention. The present invention relates to novel antiviral/anti-proliferative compounds represented herein above, pharmaceutical compositions comprising such compounds, and methods for the treatment or prophylaxis of viral infection in a subject in need of such therapy with said compounds.

17 Claims, No Drawings

(56) References Cited

U.S. PATENT DOCUMENTS

| | | | |
|---|---|---|---|
| 8,163,707 | B2 | 4/2012 | Qiu et al. |
| 8,575,119 | B2 | 11/2013 | Wang et al. |
| 8,637,475 | B1 | 1/2014 | Storer et al. |
| 8,846,638 | B2 | 9/2014 | Or et al. |
| 9,085,599 | B2 | 7/2015 | Or et al. |
| 2003/0087873 | A1 | 5/2003 | Stuyver et al. |
| 2004/0006007 | A1 | 1/2004 | Gosselin et al. |
| 2005/0009737 | A1 | 1/2005 | Clark et al. |
| 2005/0282837 | A1 | 12/2005 | Marquez et al. |
| 2007/0015905 | A1 | 1/2007 | LaColla et al. |
| 2008/0139802 | A1 | 6/2008 | Axt et al. |
| 2009/0192077 | A1 | 7/2009 | Sei et al. |
| 2009/0306007 | A1 | 12/2009 | Wagner |
| 2009/0317361 | A1 | 12/2009 | Cho et al. |
| 2010/0016251 | A1 | 1/2010 | Sofia et al. |
| 2010/0074889 | A1 | 3/2010 | Qiu et al. |
| 2010/0074890 | A1 | 3/2010 | Hagel et al. |
| 2010/0081628 | A1 | 4/2010 | Du et al. |
| 2010/0279973 | A1 | 11/2010 | Chun et al. |
| 2011/0251152 | A1 | 10/2011 | Ross et al. |
| 2011/0257122 | A1 | 10/2011 | Sofia et al. |
| 2012/0237480 | A1 | 9/2012 | Or et al. |
| 2013/0078217 | A1 | 3/2013 | Wang et al. |
| 2013/0315864 | A1 | 11/2013 | Or et al. |
| 2014/0219958 | A1 | 8/2014 | Luly et al. |

FOREIGN PATENT DOCUMENTS

| | | | |
|---|---|---|---|
| WO | 0160315 | A2 | 8/2001 |
| WO | 0190121 | A2 | 11/2001 |
| WO | 2004099241 | A1 | 11/2004 |
| WO | 2005003147 | | 1/2005 |
| WO | 2008045419 | A1 | 4/2008 |
| WO | 2010135569 | | 11/2010 |
| WO | 2012040127 | A1 | 3/2012 |
| WO | 2012094248 | | 7/2012 |
| WO | 2013187978 | | 12/2013 |
| WO | 2014019344 | A1 | 2/2014 |
| WO | 2014076490 | | 5/2014 |
| WO | 2014169278 | | 10/2014 |
| WO | 2014169280 | | 10/2014 |

OTHER PUBLICATIONS

International Search Report for PCT/US12/29381, dated Jun. 28, 2012.
Foldesi, et al., "The Synthesis of Deuterionucleosides," Nucleoside, Nucleotides and Nucleic Acids, 19(10-12):1615-1656, 2000.
Sajiki, et al., "Palladium-Catalyzed Base-Selective H-D Exchange Reaction of Nucleosides in Deuterium Oxide," Synlett, 9:1385-1388, 2005.
Maeda, et al., "Chemical Alteration of Nucleic Acids and Their Components. XII) Hydrogen-Deuterium Exchange of Nucleosides and Nucleotides Catalyzed by Platinum," Tetrabedron Letters, 19:1643-1646. 1975.
Banker, et al., "Modern Pharmaceutics," Marcel Dekker, Inc., 3:596, 1996.
Wolff, et al., "Burger's Medicinal Chemistry and Drug Discovery," John Wiley & Sons, 5(1):975-977, 1995.
Atzrodt, et al., "The Renaissance of H/D/ Exchange," Angew. Chem. Int. Ed., 46:7744-7765, 2007.
Jung, et al., "Preparation of 4'-Substituted Thymidines by Substitution of the Thymidine 5'-Esters," J. Org. Chem., 66:2624-2635. 2001.
Esaki, et al., "Synthesis of Base-Selectively Deuterium-Labelled Nucleosides by the Pd/C-Catalyzed H-D Exchange Reaction in Deuterium Oxide," Heterocycles, 66:361-369, 2005.
De Voss, et al., "General Approach to the Synthesis of Specifically Deuterium-Labeled Nucleosides," J. Org. Chem., 59:2715-2723, 1994.
Chun, et. al., "Synthesis of Stable Isotope Labeled Analogs of the Anti-Hepatitis C Virus Nucleotide Prodrugs PSI-7977 and PSI-352938," Nucleosides, Nucleotides and Nucleic Acids, 30:886, 2011.
Maurel, et al., "Detection of reactive free radicals derived from nucleosides by liquid chromatography coupled to tandem mass spectrometry of DMPO spin trapping adducts," Rapid Communications in Mass Spectrometry, 20(15):2235-2242, 2006.
Kushner, et al., "Pharmacological uses and perspectives of heavy water and deuterated compounds," Canadian Journal of Physiology and Pharmacology, 77(2):79-88, 1999.
Haskins, "the Application of Stable Isotopes in Biomedical Research," Biomedical Mas Spectrometry, 9(7):269-277, 1982.
PUBCHEM Uridine-5,6-d2, CID 46783218, pp. 1-3, Create Date: Jul. 26, 2010; p. 1; (retrieved on Aug. 25, 2014]. Retrieved from the Internet: <URL:https://pubchem.ncbi.nlm.nih.gov/summary/summary.cgi?cid=46783218>.
U.S. Appl. No. 14/959,364, filed Dec. 4, 2015.
U.S. Appl. No. 14/933,752, filed Nov. 5, 2015.
PUBCHEM Substance Record for SID 104646269, Deposit Date: Feb. 22, 2011, (retrieved on Nov. 12, 2015), Retrieved from the Internet, <URL: https://pubchem.ncbi.nlm.nih.gov/substance/104646269>.
PUBCHEM Substance Record for SID 10315736, Deposit Date: Mar. 14, 2006 (retrieved on Oct. 1, 2015), Retrieved from the Internet, <URL: https://pubchem.ncbi.nlm.nih.gov/substance/10315736#section=Top>.

* cited by examiner

NUCLEOSIDE AND NUCLEOTIDE DERIVATIVES

RELATED APPLICATIONS

This application claims the benefit of U.S. Provisional Application No. 62/041,971, filed on Aug. 26, 2014 and U.S. Provisional Application No. 62/080,827, filed on Nov. 17, 2014. The entire teachings of the above applications are incorporated herein by reference.

TECHNICAL FIELD

The present invention relates generally to compounds and pharmaceutical compositions useful as antiviral and anti-proliferative agents. Specifically, the present invention relates to nucleoside and nucleotide (referred to below as "nucleos(t)ide") derivatives with a fused 2',3'-cyclopropyl modification and methods for their preparation and use.

BACKGROUND OF THE INVENTION

Synthetic nucleosides such as 5-iodouracil and 5-fluorouracil have been used for the treatment of cancer for many years. Since the 1980's, synthetic nucleosides have also been a focus of interest for the treatment of HIV and hepatitis.

In 1981, acquired immune deficiency syndrome (AIDS) was identified as a disease that severely compromises the human immune system, and that, almost without exception, leads to death. In 1983, the etiological cause of AIDS was determined to be the human immunodeficiency virus (HIV). In 1985, it was reported that the synthetic nucleoside 3'-azido-3'-deoxythymidine (AZT) inhibits the replication of human immunodeficiency virus. Since then, a number of other synthetic nucleosides, including 2',3'-dideoxyinosine (DDI), 2',3'-dideoxycytidine (DDC), and 2',3'-dideoxy-2',3'-didehydrothymidine (D4T), have been proven to be effective against HIV. After cellular phosphorylation to the 5'-triphosphate by cellular kinases, these synthetic nucleosides are incorporated into a growing strand of viral DNA, causing chain termination due to the absence of the 3'-hydroxyl group. They can also inhibit the viral enzyme reverse transcriptase.

The success of various synthetic nucleosides in inhibiting the replication of HIV in vivo or in vitro has led a number of researchers to design and test nucleosides that substitute a heteroatom for the carbon atom at the 3'-position of the nucleoside. European Patent Publication No. 0,337,713 and U.S. Pat. No. 5,041,449, assigned to BioChem Pharma, Inc., disclose 2-substituted-4-substituted-1,3-dioxolanes that exhibit antiviral activity. U.S. Pat. No. 5,047,407 and European Patent Publication No. 0,382,526, also assigned to BioChem Pharma, Inc., disclose that a number of 2-substituted-5-substituted-1,3-oxathiolane nucleosides have antiviral activity, and specifically report that 2-hydroxymethyl-5-(cytosin-1-yl)-1,3-oxathiolane (referred to below as BCH-189) has approximately the same activity against HIV as AZT, with little toxicity.

It has also been disclosed that cis-2-hydroxymethyl-5-(5-fluorocytosin-1-yl)-1,3-oxathiolane ("FTC") has potent HIV activity. Schinazi, et al., "Selective Inhibition of Human Immunodeficiency viruses by Racemates and Enantiomers of cis-5-Fluoro-1-[2-(Hydroxymethyl)-1,3-Oxathiolane-5-yl]-Cytosine" Antimicrobial Agents and Chemotherapy, November 1992, 2423-2431. See also U.S. Pat. Nos. 5,210,085; 5,814,639; and 5,914,331.

Another virus that causes a serious human health problem is the hepatitis B virus (referred to below as "HBV"). HBV is second only to tobacco as a cause of human cancer. The mechanism by which HBV induces cancer is still not completely known. It is postulated that it may directly trigger tumor development, or indirectly trigger tumor development through chronic inflammation, cirrhosis, and cell regeneration associated with the infection.

After a two to six month incubation period in which the host is unaware of the infection, HBV infection can lead to acute hepatitis and liver damage, that causes abdominal pain, jaundice, and elevated blood levels of certain enzymes. HBV can cause fulminant hepatitis, a rapidly progressive, often fatal form of the disease in which massive sections of the liver are destroyed.

Patients typically recover from acute hepatitis. In some patients, however, high levels of viral antigen persist in the blood for an extended, or indefinite, period, causing a chronic infection. Chronic infections can lead to chronic persistent hepatitis. Patients infected with chronic persistent HBV are most common in developing countries. By mid-1991, there were approximately 225 million chronic carriers of HBV in Asia alone, and worldwide, almost 300 million carriers. Chronic persistent hepatitis can cause fatigue, cirrhosis of the liver, and hepatocellular carcinoma, a primary liver cancer.

In Western industrialized countries, high risk groups for HBV infection include those in contact with HBV carriers or their blood samples. The epidemiology of HBV is very similar to that of acquired immune deficiency syndrome, which accounts for why HBV infection is common among patients with AIDS or AIDS related complex. However, HBV is more contagious than HIV.

Both FTC and 3TC exhibit activity against HBV. Furman, et al., "The Anti-Hepatitis B Virus Activities, Cytotoxicities, and Anabolic Profiles of the (−) and (+) Enantiomers of cis-5-Fluoro-1-[2-(Hydroxymethyl)-1,3-oxathiolane-5-yl]-Cytosine" Antimicrobial Agents and Chemotherapy, December 1992, pp. 2686-2692; and Cheng, et al., Journal of Biological Chemistry, 267(20), pp. 13938-13942 (1992). Other compounds that exhibit activity against HBV in humans include Clevudine or CLV (L-FMAU) (Pharmasset, Inc. under license from The University of Georgia Research Foundation and Yale University), L-dT and L-dC (Idenix Pharmaceuticals, Inc.), and Entecavir (BMS). Adefovir dipivoxil (Gilead) and Tenofovir disoproxil (Gilead) are acyclic nucleoside phosphonate derivatives as anti-HBV drugs.

HCV is the major causative agent for post-transfusion and for sporadic non A, non B hepatitis (Alter, H. J. (1990) *J. Gastro. Hepatol.* 1:78-94; Dienstag, J. L. (1983) *Gastro* 85:439-462). Despite improved screening, HCV still accounts for at least 25% of the acute viral hepatitis in many countries (Alter, H. J. (1990) supra; Dienstag, J. L. (1983) supra; Alter M. J. et al. (1990a) *J.A.M.A.* 264:2231-2235; Alter M. J. et al (1992) *N. Engl. J. Med.* 327:1899-1905; Alter, M. J. et al. (1990b) *N. Engl. J. Med.* 321:1494-1500). Infection by HCV is insidious in a high proportion of chronically infected (and infectious) carriers who may not experience clinical symptoms for many years. The high rate of progression of acute infection to chronic infection (70-100%) and liver disease (>50%), its world-wide distribution and lack of a vaccine make HCV a significant cause of morbidity and mortality. Currently, a few drugs and many drug candidates have been used and are being studied to treat HCV. These drugs or drug candidates include interferon, ribavirin, protease inhibitor, polymerase inhibitor, NS5A inhibitor, and cyclophilin inhibitor. Sofosbuvir (Gilead, a modified uridine monophosphate prodrug) has been approved recently to treat HCV by functioning as a viral RNA chain terminator. Various combinations of drugs or drug candidates have been continuously active in clinical settings. Selection of patients for treatment may be determined by biochemical, virologic, and when necessary, liver biopsy findings, rather than presence or absence of symptoms.

Interferon is given by injection, and may have a number of side effects including flu-like symptoms such as headaches, fever, fatigue, loss of appetite, nausea, vomiting, depression and thinning of hair. It may also interfere with the production of white blood cells and platelets by depressing the bone marrow. Periodic blood tests are required to monitor blood cells and platelets. Ribavirin can cause sudden, severe anemia, and birth defects so women should avoid pregnancy while taking it and for 6 months following treatment. The severity and type of side effects differ for each individual. Treatment of children with HCV is not currently approved but is under investigation. While 50-60% of patients respond to treatment initially, lasting clearance of the virus occurs in only about 10-40% of patients. Treatment may be prolonged and given a second time to those who relapse after initial treatment. Re-treatment with bioengineered consensus interferon alone results in elimination of the virus in 58% of patients treated for one year. Side effects occur but the medication is usually well tolerated. Combined therapy (interferon and ribavirin) shows elimination of the virus in 47% after 6 months of therapy. Side effects from both drugs may be prominent.

There are many other DNA or RNA viruses or retroviruses which can cause social distress and serious human health problems to almost every human organ and system with varied morbidity and mortality. These pathogens may include West Nile virus (WNV), Yellow Fever virus (YFV), influenza virus, respiratory syncytial virus (RSV), human cytomegalovirus (HCMV), human papillomavirus (HPV), SARS coronavirus, herpes virus, human T-lymphotropic virus (HTLV), and rabies, etc. Certain viral infections might play a pivotal pathogenetic role in the development of many chronic diseases.

A tumor is an unregulated, disorganized proliferation of cell growth. A tumor is malignant, or cancerous, if it has the properties of invasiveness and metastasis. Invasiveness refers to the tendency of a tumor to enter surrounding tissue, breaking through the basal laminas that define the boundaries of the tissues, thereby often entering the body's circulatory system. Metastasis refers to the tendency of a tumor to migrate to other areas of the body and establish areas of proliferation away from the site of initial appearance.

Cancer is now the second leading cause of death in the United States. Over 8,000,000 persons in the United States have been diagnosed with cancer, with 1,208,000 new diagnoses expected in 1994. Over 500,000 people die annually from the disease in this country.

Cancer is not fully understood on the molecular level. It is known that exposure of a cell to a carcinogen such as certain viruses, certain chemicals, or radiation, leads to DNA alteration that inactivates a "suppressive" gene or activates an "oncogene." Suppressive genes are growth regulatory genes, which upon mutation, can no longer control cell growth.

Oncogenes are initially normal genes (called prooncongenes) that by mutation or altered context of expression become transforming genes. The products of transforming genes cause inappropriate cell growth. More than twenty different normal cellular genes can become oncongenes by genetic alteration. Transformed cells differ from normal cells in many ways, including cell morphology, cell-to-cell interactions, membrane content, cytoskeletal structure, protein secretion, gene expression and mortality (transformed cells can grow indefinitely).

All of the various cell types of the body can be transformed into benign or malignant tumor cells. The most frequent tumor site is lung, followed by colorectal, breast, prostate, bladder, pancreas and then ovary. Other prevalent types of cancer include leukemia, central nervous system cancers, including brain cancer, melanoma, lymphoma, erythroleukemia, uterine cancer, and head and neck cancer.

Cancer is now primarily treated with one or a combination of three means of therapies: surgery, radiation and chemotherapy. Surgery involves the bulk removal of diseased tissue. While surgery is sometimes effective in removing tumors located at certain sites, for example, in the breast, colon and skin, it cannot be used in the treatment of tumors located in other areas, such as the backbone, or in the treatment of disseminated neoplastic conditions such as leukemia. Chemotherapy involves the disruption of cell replication or cell metabolism. It is used most often in the treatment of leukemia, as well as breast, lung, and testicular cancer.

There are five major classes of chemotherapeutic agents currently in use for the treatment of cancer: natural products and their derivatives; anthacyclines; alkylating agents; antiproliferatives (also called antimetabolites); and hormonal agents. Chemotherapeutic agents are often referred to as antineoplastic agents.

The alkylating agents are believed to act by alkylating and cross-linking guanine and possibly other bases in DNA, arresting cell division. Typical alkylating agents include nitrogen mustards, ethyleneimine compounds, alkyl sulfates, cisplatin and various nitrosoureas. A disadvantage with these compounds is that they not only attack malignant cells, but also other cells which are naturally dividing, such as those of bone marrow, skin, gastrointestinal mucosa, and fetal tissue.

Antimetabolites are typically reversible or irreversible enzyme inhibitors or compounds that otherwise interfere with the replication, replication translation or transcription of nucleic acids.

Several synthetic nucleosides have been identified that exhibit anticancer activity. A well known nucleoside derivative with strong anticancer activity is 5-fluorouracil. 5-fluorouracil has been used clinically in the treatment of malignant tumors, including, for example, carcinomas, sarcomas, skin cancer, cancer of the digestive organs, and breast cancer. 5-Fluorouracil, however, causes serious adverse reactions such as nausea, alopecia, diarrhea, stomatitis, leukocytic thrombocytopenia, anorexia, pigmentation and edema. Derivatives of 5-fluorouracil with anti-cancer activity have been described in U.S. Pat. No. 4,336,381, and in Japanese Patent Publication Nos. 50-50383, 50-50384, 50-64281, 51-146482, and 53-84981.

U.S. Pat. No. 4,000,137 discloses that the peroxidate oxidation product of inosine, adenosine or cytidine with methanol or ethanol has activity against lymphocytic leukemia.

Cytosine arabinoside (also referred to as Cytarabin, araC, and Cytosar) is a nucleoside analog of deoxycytidine that was first synthesized in 1950 and introduced into clinical medicine in 1963. It is currently an important drug in the treatment of acute myeloid leukemia. It is also active against acute lymphocytic leukemia, and to a lesser extent, is useful in chronic myelocytic leukemia and non-Hodgkin's lymphoma. The primary action of araC is inhibition of nuclear DNA synthesis. Handschumacher, R. and Cheng, Y., "Purine and Pyrimidine Antimetabolites" *Cancer Medicine, Chapter XV*-1, 3rd Edition, Edited by J. Holland, et al., Lea and Febigol, publishers.

5-Azacytidine is a cytidine analog that is primarily used in the treatment of acute myelocytic leukemia and myelodysplastic syndrome.

2-Fluoroadenosine-5'-phosphate (Fludara, also referred to as FaraA) is one of the most active agents in the treatment of chronic lymphocytic leukemia. The compound acts by inhibiting DNA synthesis. Treatment of cells with F-araA is associated with the accumulation of cells at the G1/S phase boundary and in S phase; thus, it is a cell cycle S phase-specific drug. Incorporation of the active metabolite, F-araATP, retards DNA chain elongation. F-araA is also a potent inhibitor of ribonucleotide reductase, the key enzyme responsible for the formation of dATP.

2-Chlorodeoxyadenosine is useful in the treatment of low grade B-cell neoplasms such as chronic lymphocytic leukemia, non-Hodgkins' lymphoma, and hairy-cell leukemia.

In light of the fact that various viral infections have reached epidemic levels worldwide, and have tragic effects on the infected patient, there remains a strong need to provide new effective pharmaceutical agents to treat these diseases that have low toxicity to the host. Further, there is a need to provide new antiproliferative agents.

Therefore, it is an object of the present invention to provide a method and composition for the treatment of human patients with viral infections.

It is a further object of the present invention to provide new antiproliferative agents.

It is still another object of the present invention to provide a new process for the preparation of 2',3'-fused cyclopropylated nucleos(t)ide derivatives of the present invention.

SUMMARY OF THE INVENTION

The present invention includes β-D and β-L-nucleoside derivatives, pharmaceutical compositions comprising such compounds, as well as methods to treat or prevent viral infection or abnormal cellular proliferation comprising administering said compounds or compositions. In addition, the present invention includes the process for the preparation of such compounds, and the related β-D and β-L-nucleoside derivatives.

In its principal aspect, the present invention provides a compound of Formula (I):

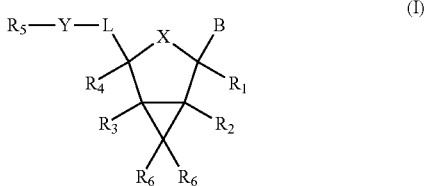

or a pharmaceutically acceptable salt thereof, wherein:
B is a nucleobase;
X is selected from the group consisting of: O, S, NH, NMe, $CH_2$, CHF, $CF_2$, $C=CH_2$, C=CHF, and $C=CF_2$; preferably, X is O;
$R_1$ and $R_4$ are each independently selected from the group consisting of: hydrogen, halogen, —CN, —$N_3$, and optionally substituted $C_1$-$C_4$ alkyl; preferably, $R_1$ is hydrogen, fluoro, or methyl; preferably, $R_4$ is hydrogen, fluoro, —$N_3$, or methyl;

$R_2$ and $R_3$ are each independently selected from the group consisting of: hydrogen, OH, $OR_{11}$, halogen, —CN, —$N_3$, $NH_2$, $OC(O)R_{11}$, $OC(O)OR_{11}$, $OC(O)(NR_{11}R_{12})$, $N(R_{11})C(O)R_{11}$, $N(R_{11})C(O)OR_{11}$, $N(R_{11})C(O)(NR_{11}R_{12})$, $OP(O)(OR_1)(OR_{12})$, $OP(O)(OR_1)(NR_{11}R_{12})$, $OP(O)(OR_{11})(NR_{11}R_{12})$; wherein at least one of $R_2$ and $R_3$ is not hydrogen; preferably, $R_2$ and $R_3$ are each independently OH, fluoro, OMe, OAc, or $OP(O)(OH)_2$; or alternatively, $R_2$ and $R_3$ are taken together with the carbon atoms to which they are attached to form a cyclic carbonate, optionally substituted cyclic carbamate, optionally substituted cyclic phosphate, optionally substituted cyclic phosphoramidate or optionally substituted cyclic phosphorodiamidate;

$R_{11}$ and $R_{12}$ at each occurrence are independently selected from the group consisting of: hydrogen, optionally substituted $C_1$-$C_{20}$ alkyl, and optionally substituted $C_2$-$C_{20}$ alkenyl; or when they occur together, $R_{11}$ and $R_{12}$ are alternatively taken together with the atoms to which they are attached and any intervening atoms to form a heterocyclic ring;

L is $CH_2$, CHMe or absent;
Y is O, $NR_{11}$, or $CH_2$;
$R_5$ is selected from the group consisting of: hydrogen, monophosphoryl, diphosphoryl, triphosphoryl, $C(O)R_{11}$, $C(O)OR_{11}$, $C(O)(NR_{11}R_{12})$, and —$(P(=Y^1)(—Y^2—R^x)(—Y^3))_n—R^y$;
n is 1 to 3;
$Y^1$ is O or S;
$Y^2$ and $Y^3$ at each occurrence are each independently O, S, or NH;
$R^x$ and $R^y$ at each occurrence are each independently selected from the group consisting of: hydrogen, optionally substituted $C_1$-$C_{20}$ alkyl, optionally substituted $C_2$-$C_{20}$ alkenyl, optionally substituted $C_3$-$C_8$ cycloalkyl, optionally substituted aryl, and optionally substituted heteroaryl; or alternatively $R^x$ and $R^y$ are taken together with the atoms to which they are attached to form a heterocyclic ring or ring system;

Alternatively, $R^3$ and $R^5$ are taken together with the atoms to which they are attached to form —$P(=Y)(Y^2—R^x)Y^4$—; wherein $Y^4$ is O or NH; and $R_6$ at each occurrence is each independently selected from the group consisting of hydrogen, halogen, and optionally substituted $C_1$-$C_4$ alkyl. Preferably, $R_6$ at each occurrence is each independently hydrogen or fluoro.

In one embodiment, the present invention provides a pharmaceutical composition comprising a therapeutically effective amount of a compound or combination of compounds of the present invention, or a pharmaceutically acceptable salt thereof.

In another embodiment, the present invention provides a method of inhibiting the replication of an RNA or DNA containing virus comprising contacting said virus with a therapeutically effective amount of a compound or a combination of compounds of the present invention, or a pharmaceutically acceptable salt thereof. Particularly, this invention is directed to methods of inhibiting the replication of HIV, HBV, RSV, HCMV, HPV and HCV.

In yet another embodiment, the present invention provides a method of treating or preventing infection caused by an RNA or DNA-containing virus comprising administering to a patient in need of such treatment a therapeutically effective amount of a compound or combination of compounds of the present invention, or a pharmaceutically acceptable salt thereof. Particularly, this invention is directed to methods of treating or preventing infection caused by HIV, HBV, RSV, HCMV, HPV and HCV.

In still another embodiment, the present invention provides the use of a compound or combination of compounds of the present invention, or a pharmaceutically acceptable salt form thereof, as defined hereinafter, in the preparation of a medicament for the treatment or prevention of infection caused by RNA or DNA-containing virus, specifically HIV, HBV, RSV, HCMV, HPV and HCV.

DETAILED DESCRIPTION OF THE INVENTION

In one embodiment of the present invention is a compound of Formula (I) as illustrated above, or a pharmaceutically acceptable salt thereof.

In another embodiment of the present invention is a fused 2',3'-cyclopropanated nucleos(t)ide derivative represented by formula (I-D) or its β-L isomer (I-L) as illustrated below, or pharmaceutically acceptable salt thereof:

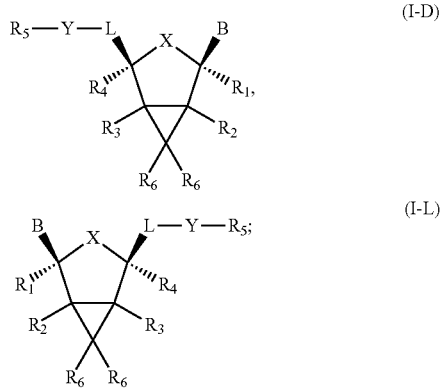

wherein $R_1$, $R_2$, $R_3$, $R_4$, $R_5$, $R_6$, B, L, X, and Y are as previously defined.

In yet another embodiment of the present invention is a fused 2',3'-cyclopropanated nucleos(t)ide derivative represented by formula (I-a) or its isomer (I-b) as illustrated below, or pharmaceutically acceptable salt thereof:

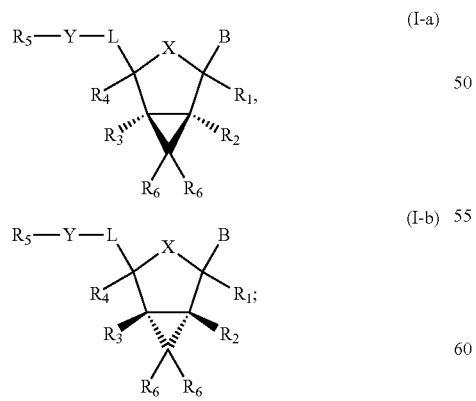

wherein $R_1$, $R_2$, $R_3$, $R_4$, $R_5$, $R_6$, B, L, X, and Y are as previously defined.

In a particular embodiment of the present invention is a fused 2',3'-cyclopropanated nucleos(t)ide derivative represented by formula (Ia), or its β-L enantiomer (Ib), or pharmaceutically acceptable salt thereof:

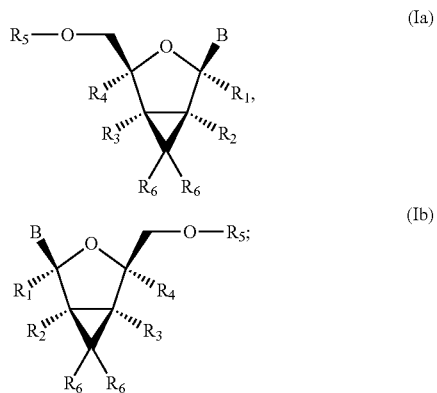

wherein $R_1$, $R_2$, $R_3$, $R_4$, $R_5$, $R_6$, and B are as previously defined.

In another particular embodiment of the present invention is a fused 2',3'-cyclopropanated nucleoside derivative represented by formula (II), or pharmaceutically acceptable salt thereof:

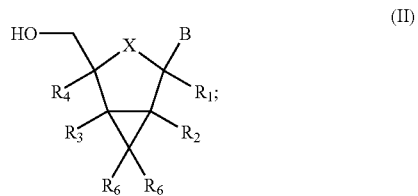

wherein $R_1$, $R_2$, $R_3$, $R_4$, $R_6$, B and X are as previously defined.

In another particular embodiment of the present invention is a fused 2',3'-cyclopropanated nucleoside derivative represented by formula (IIa), or its β-L enantiomer (IIb), or pharmaceutically acceptable salt thereof:

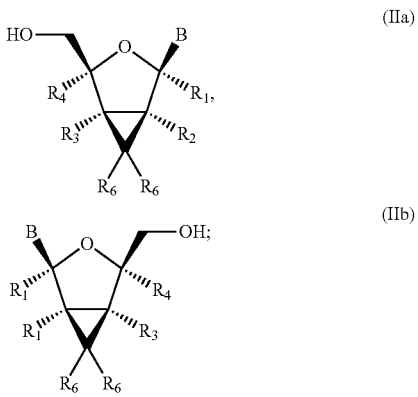

wherein $R_1$, $R_2$, $R_3$, $R_4$, $R_6$, and B are as previously defined.

In another embodiment of the present invention is a fused 2',3'-cyclopropanated nucleotide derivative represented by formula (III), or pharmaceutically acceptable salt thereof:

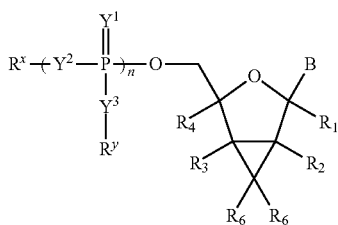
(III)

wherein $R_1$, $R_2$, $R_3$, $R_4$, $R_6$, $R^x$, $R^Y$, B, n, $Y^1$, $Y^2$ and $Y^3$ are as previously defined.

In another particular embodiment of the present invention is a fused 2',3'-cyclopropanated nucleotide derivative represented by formula (IIIa), or pharmaceutically acceptable salt thereof:

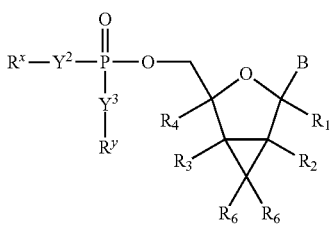
(IIIa)

wherein $R_1$, $R_2$, $R_3$, $R_4$, $R_6$, $R^x$, $R^Y$, B, $Y^2$ and $Y^3$ are as previously defined.

In another particular embodiment of the present invention is a fused 2',3'-cyclopropanated nucleotide derivative represented by formula (IIIb), or pharmaceutically acceptable salt thereof:

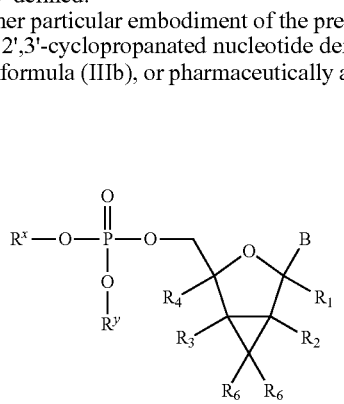
(IIIb)

wherein $R_1$, $R_2$, $R_3$, $R_4$, $R_6$, $R^x$, $R^Y$, n and B are as previously defined.

In another particular embodiment of the present invention is a fused 2',3'-cyclopropanated nucleotide derivative represented by formula (IIIc), or pharmaceutically acceptable salt thereof:

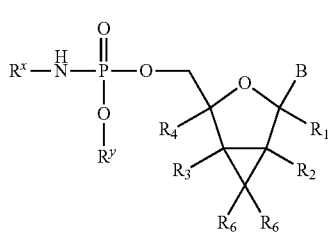
(IIIc)

wherein $R_1$, $R_2$, $R_3$, $R_4$, $R_6$, $R^x$, $R^Y$, and B are as previously defined.

In another particular embodiment of the present invention is a fused 2',3'-cyclopropanated nucleotide derivative represented by formula (IIId), or pharmaceutically acceptable salt thereof:

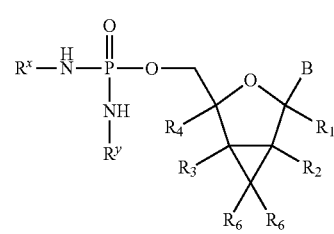
(IIId)

wherein $R_1$, $R_2$, $R_3$, $R_4$, $R_6$, $R^x$, $R^Y$, and B are as previously defined.

In another particular embodiment of the present invention is a fused 2',3'-cyclopropanated nucleotide derivative represented by formula (IIIe), or pharmaceutically acceptable salt thereof:

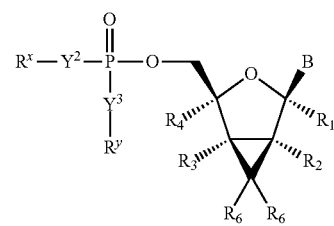
(IIIe)

wherein $R_1$, $R_2$, $R_3$, $R_4$, $R_6$, $R^x$, $R^Y$, B, $Y^2$ and $Y^3$ are as previously defined.

Illustrative structures of formula (IIIe) can be represented by formula (IIIe1~IIIe9):

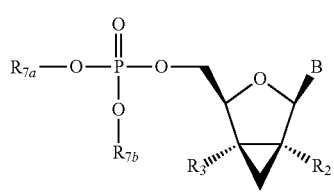
(IIIe1)

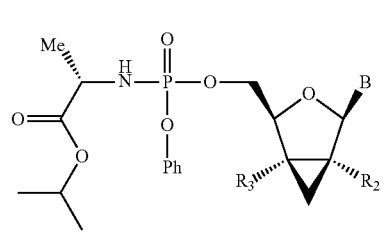
(IIIe2)

-continued

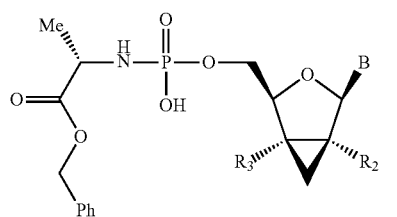
(IIIe3)

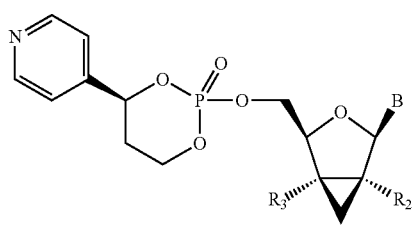
(IIIe4)

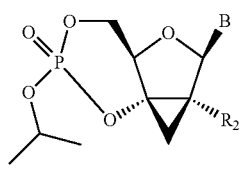
(IIIe5)

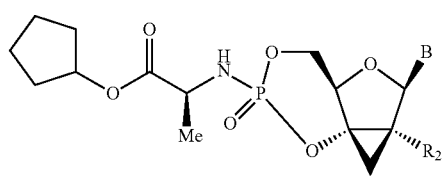
(IIIe6)

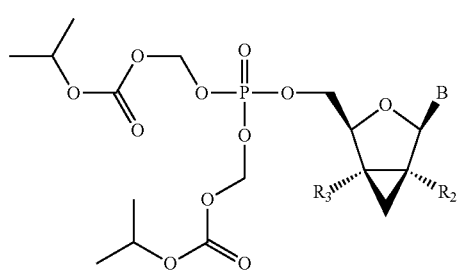
(IIIe7)

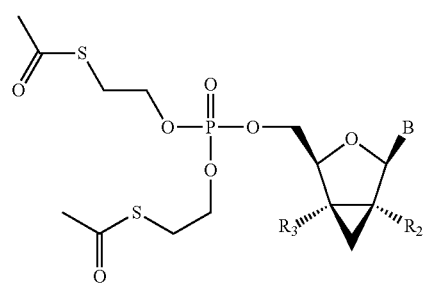
(IIIe8)

-continued

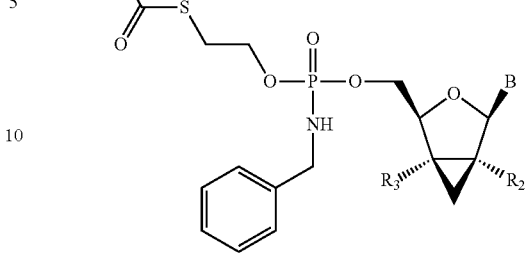
(IIIe9)

wherein $R_2$, $R_3$, and B are as previously defined; $R_{7a}$ and $R_{7b}$ are independently hydrogen, substituted or unsubstituted —$C_1$-$C_{20}$ alkyl, or a group that is preferentially removed in a hepatocyte to yield the corresponding OH group. The term "preferentially removed in a hepatocyte" as used herein means at least part of the group is removed in a hepatocyte at a rate higher than the rate of removal of the same group in a non-hepatocytic cell (e.g., fibroblast or lymphocyte). It is therefore contemplated that the removable group includes all pharmaceutically acceptable groups that can be removed by a reductase, esterase, cytochrome P450 or any other specific liver enzyme. Alternative contemplated groups may also include groups that are not necessarily preferentially removed in a hepatocyte, but effect at least some accumulation and/or specific delivery to a hepatocyte (e.g., esters with selected amino acids, including valine, leucine, isoleucine, or polyarginine or polyaspartate).

In some embodiments of the present invention, $R_5$ is a monophosphoryl. In some embodiments of the present invention, $R_5$ is a diphosphoryl. In some embodiments of the present invention, $R_5$ is a triphosphoryl.

In some embodiments of the present invention, $R_1$ and $R_6$ at each occurrence are each independently hydrogen, fluoro or methyl; $R_2$ and $R_3$ at each occurrence are each independently fluoro, OH, OMe or $NH_2$; $R_4$ at each occurrence is each independently hydrogen, fluoro, methyl or —$N_3$.

In some embodiments of the present invention, $R_1$ and $R_6$ at each occurrence are each independently hydrogen, fluoro or methyl; $R_2$ at each occurrence is each independently hydrogen, fluoro, OH, OMe or $NH_2$; $R_3$ at each occurrence is each independently fluoro, OH, OMe or $NH_2$; $R_4$ at each occurrence is each independently hydrogen, fluoro, methyl or —$N_3$.

In some embodiments of the present invention, $R_1$ and $R_6$ at each occurrence are each independently hydrogen, fluoro or methyl; $R_2$ at each occurrence is each independently fluoro, OH, OMe or $NH_2$; $R_3$ at each occurrence is each independently hydrogen, fluoro, OH, OMe or $NH_2$; $R_4$ at each occurrence is each independently hydrogen, fluoro, methyl or —$N_3$.

In some embodiments of the present invention, L is $CH_2$; Y is O; $Y^1$ is O; $Y^2$ and $Y^3$ at each occurrence are each independently O or NH.

In certain embodiments of the present invention, —$Y^2$—$R^x$ and —$Y^3$—$R^y$ at each occurrence are each independently an amino acid or derivative thereof, or an ester thereof.

In some embodiments of the present invention, —$Y^2$—$R^x$ and —$Y^3$—$R^y$ at each occurrence are each independently an N-linked or O-linked amino acid residue or an N-linked or O-linked residue of an amino acid derivative.

In yet another particular embodiment of the present invention is a fused 2',3'-cyclopropanated nucleos(t)ide derivative represented by formula (I), or pharmaceutically acceptable salt thereof, with B at each occurrence is preferably a heterocycle moiety containing at least one nitrogen, most preferably a pyrimidinyl, purinyl group or the like of the general formula of (B1)-(B2):

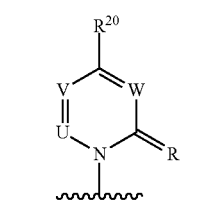

(B1)

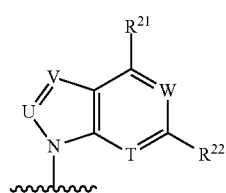

(B2)

wherein:

R is selected from the group consisting of: O, S, NR$^x$, NC(O)R$^x$, NC(O)OR$^x$ and NC(O)NR$^x$R$^y$;

T, U, V and W are each independently N or CR$_{17}$; wherein R$_{17}$ at each occurrence is independently selected from a group consisting of: hydrogen, halogen, —CN, —C(O)R$^x$, —C(O)NR$^x$R$^y$, —NO$_2$, —N$_3$, —OR$^x$, —SR$^x$, —NR$^x$R$^y$, —OC(O)R$^x$, —OC(O)OR$^x$, —NHC(O)R$^x$, —NHC(O)OR$^x$ and —NHC(O)NR$^x$R$^y$, substituted or unsubstituted aryl, substituted or unsubstituted heteroaryl, substituted or unsubstituted heterocyclic, substituted or unsubstituted —C$_1$-C$_8$ alkyl, substituted or unsubstituted —C$_2$-C$_8$ alkenyl, substituted or unsubstituted —C$_2$-C$_8$ alkynyl;

R$^{20}$, R$^{21}$ and R$^{22}$ are each independently selected from the group consisting of: hydrogen, halogen, —CN, —C(O)R$^x$, —C(O)NR$^x$R$^y$, —NO$_2$, —N$_3$, —OR$^x$, —SR$^x$, —NR$^x$R$^y$, —OC(O)R$^x$, —OC(O)OR$^x$, —NHC(O)R$^x$, —NHC(O)OR$^x$ and —NHC(O)NR$^x$R$^y$, substituted or unsubstituted aryl, substituted or unsubstituted heteroaryl, substituted or unsubstituted heterocyclic, substituted or unsubstituted —C$_1$-C$_8$ alkyl, substituted or unsubstituted —C$_2$-C$_8$ alkenyl, substituted or unsubstituted —C$_2$-C$_8$ alkynyl.

Illustrative structures of B can be represented by formula (B1a~B1r), (B2a~B2o), and (B3a~B3j):

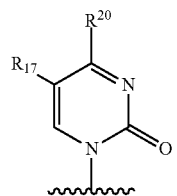

(B1a)

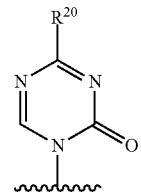

(B1b)

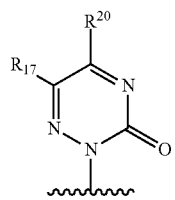

(B1c)

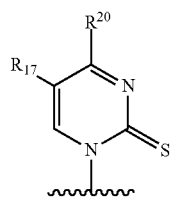

(B1d)

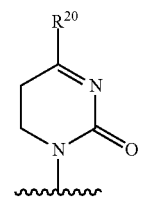

(B1e)

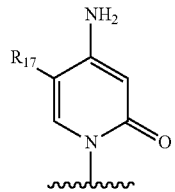

(B1f)

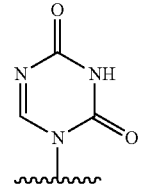

(B1g)

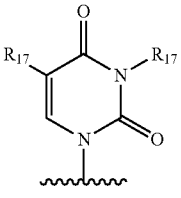

(B1h)

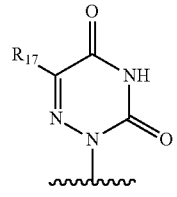

(B1i)

-continued
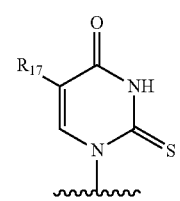
(B1j)
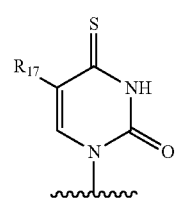
(B1k)
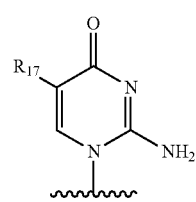
(B1l)
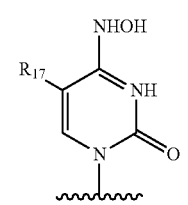
(B1m)
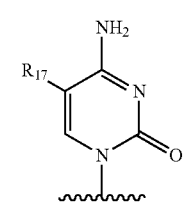
(B1n)
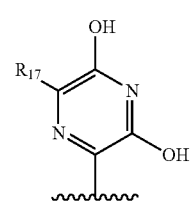
(B1o)
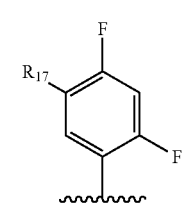
(B1p)
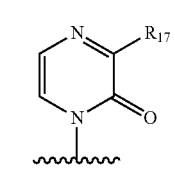
(B1q)
-continued
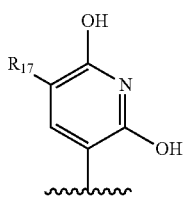
(B1r)
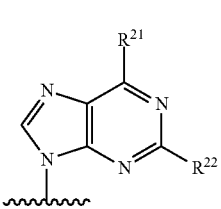
(B2a)
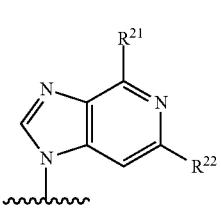
(B2b)
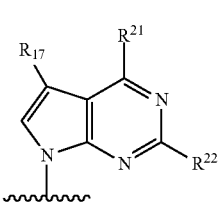
(B2c)
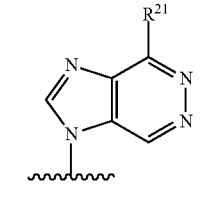
(B2d)
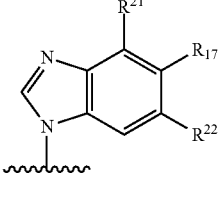
(B2e)
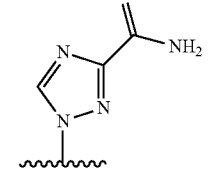
(B2f)
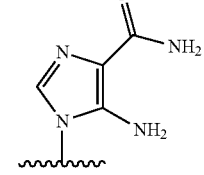
(B2g)

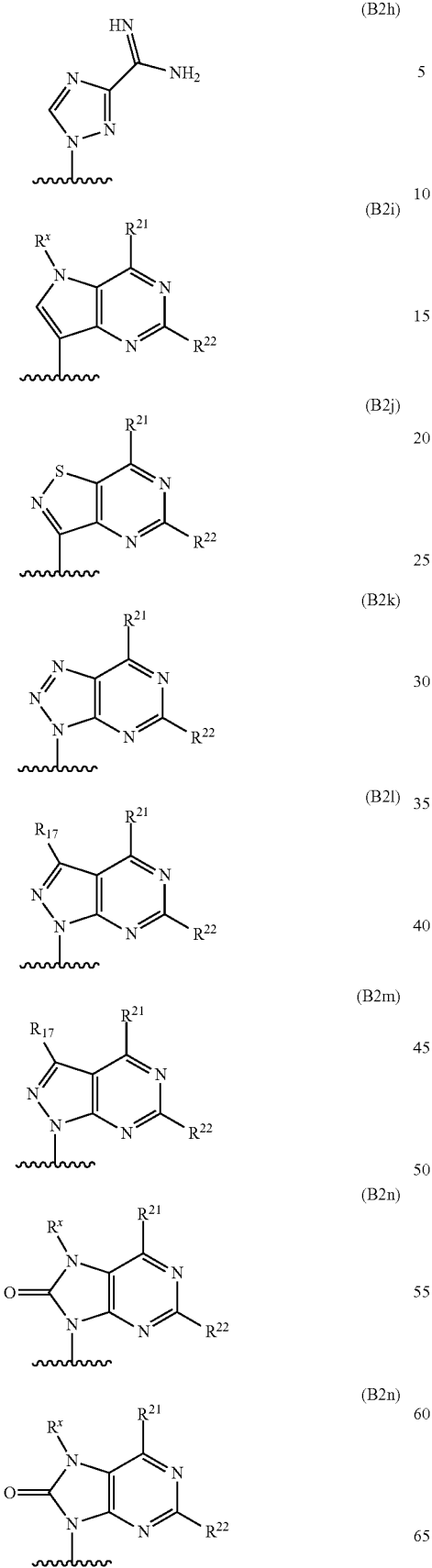
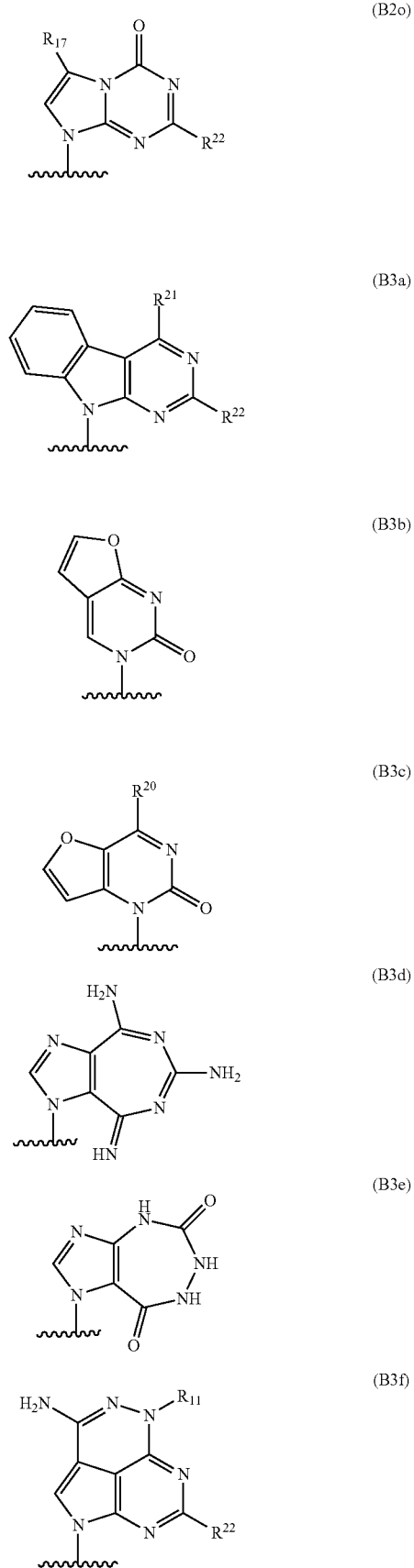

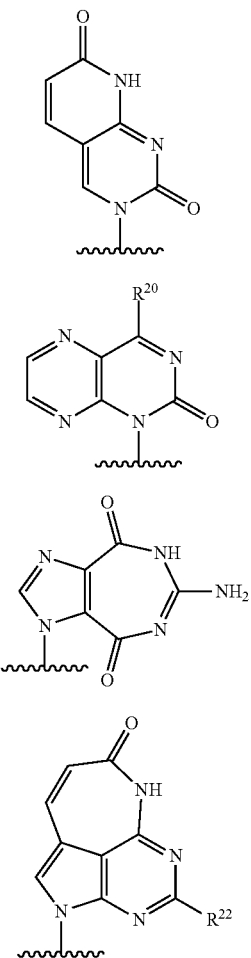

wherein $R^x$, $R_{17}$, $R_{11}$, $R^{20}$, $R^{21}$ and $R^{22}$ are as previously defined.

In one embodiment of the invention, the fused 2',3'-cyclopropanated nucleos(t)ide derivatives of the invention are the isolated β-D or β-L isomer. In another embodiment of the invention, the nucleos(t)ide derivative is in a enantiomeric mixture in which the desired enantiomer is at least 95%, 98% or 99% free of the other enantiomer. In a preferred embodiment, the nucleos(t)ide derivatives are enantiomerically enriched.

In one embodiment of the present invention, the compounds of the formula (I) are in the β-D configuration. In an alternate embodiment of the present invention, the compounds of formula (I) are in the β-L configuration.

Some of the nucleos(t)ide derivatives depicted above are in the β-D configuration, however, it should be understood that the nucleos(t)ide derivatives in this invention can be either in the β-L or β-D configuration.

The nucleoside derivatives of the present invention are biologically active molecules that are useful in the treatment or prophylaxis of viral infections, and in particular human immunodeficiency virus (HIV) and/or hepatitis B virus (HBV) infection. The compounds are also useful for the treatment of abnormal cellular proliferation, including tumors and cancer. In another embodiment of the present invention, the compounds of the invention are useful in the treatment of HCV. One can easily determine the spectrum of activity by evaluating the compound in the assays described herein or with another confirmatory assay.

For instance, in one embodiment the efficacy of the antiviral compound is measured according to the concentration of compound necessary to reduce the plaque number of the virus in vitro, according to methods set forth more particularly herein, by 50% (i.e. the compound's $EC_{50}$). In preferred embodiments the compound exhibits an $EC_{50}$ of less than 15 or preferably, less than 10 micromolar in vitro.

In another embodiment, for the treatment or prophylaxis of a viral infection, and in particular an HIV, HCV or HBV infection, in a host, a compound of the invention or a derivative or pharmaceutically acceptable salt thereof can be administered in combination or alternation with another antiviral agent, such as an anti-HIV agent or anti-hepatitis agent, including those of the formula above. Alternatively, for the treatment of abnormal cellular proliferation, such as tumors and cancer, in a host, the compound of the invention or a derivative or pharmaceutically acceptable salt thereof can be administered in combination or alternation with another antiproliferative agent, such as an anti-neoplastic agent, including those of the formula above. In general, in combination therapy, effective dosages of two or more agents are administered together, whereas during alternation therapy, an effective dosage of each agent is administered serially. The dosages will depend on absorption, inactivation and excretion rates of the drug as well as other factors known to those skilled in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

The compounds of the present invention can also be used to treat equine infectious anemia virus (EIAV), feline immunodeficiency virus, and simian immunodeficiency virus. (Wang, S., et al., "Activity of nucleoside and non-nucleoside reverse transcriptase inhibitors (NNRTI) against equine infectious ane mia virus (EIAV)." *First National Conference on Human Retroviruses and Related Infections*, Washington, D.C., Dec. 12-16, 1993; Sellon D. C., "Equine Infectious Anemia" *Vet. Clin. North Am. Equine Pract. United States*, 9: 321-336, 1993; Philpott, M. S., et al. "Evaluation of 9-(2-phosphonylmethoxyethyl)adenine therapy for feline immunodeficiency virus using a quantitative polymerase chain reaction" *Vet. Immunol. Immunopathol.* 35:155-166, 1992.

The present invention also provides a pharmaceutical composition for the treatment and/or prophylaxis of a viral infection, and in particular a HBV, HCV or HIV infection, in a host, preferably a human, comprising a therapeutically effective amount of a compound of the present invention, optionally in a pharmaceutically acceptable carrier.

The present invention also provides a pharmaceutical composition for the treatment and/or prophylaxis of an abnormal cellular proliferation, such as tumors and cancer, in a host, preferably a human, comprising a therapeutically effective amount of a compound of the present invention, optionally in a pharmaceutically acceptable carrier.

The present invention also provides a pharmaceutical composition for the treatment and/or prophylaxis of a viral infection, and in particular a HBV, HCV or HIV infection, in a host, preferably a human, comprising a therapeutically effective amount of a compound of the present invention, in combination with one or more other effective antiviral agent, and in particular an anti-HBV, anti-HCV or anti-HIV agent, optionally in a pharmaceutically acceptable carrier.

The present invention also provides a pharmaceutical composition for the treatment and/or prophylaxis of an abnormal cellular proliferation, such as tumors and cancer, in a host, preferably a human, comprising a therapeutically effective amount of a compound of the present invention, in combination with one or more other effective antiproliferative agent, such as an antineoplastic agent, optionally in a pharmaceutically acceptable carrier.

The present invention also provides a method for the treatment and/or prophylaxis of a viral infection, and in particular a HBV, HCV or HIV infection, in a host, preferably a human, comprising administering to the host a therapeutically effective amount of a compound of the present invention, optionally in a pharmaceutically acceptable carrier.

The present invention also provides a method for the treatment and/or prophylaxis of an abnormal cellular proliferation, such as tumors and cancer, in a host, preferably a human, comprising administering to the host a therapeutically effective amount of a compound of the present invention, optionally in a pharmaceutically acceptable carrier.

The present invention also provides a method for the treatment and/or prophylaxis of a viral infection, and in particular a HBV, HCV or HIV infection, in a host, preferably a human, comprising administering to the host a therapeutically effective amount of a compound of the present invention, in combination and/or alternation with one or more other effective antiviral agent, and in particular an anti-HBV, anti-HCV or anti-HIV agent, optionally in a pharmaceutically acceptable carrier.

The present invention also provides a method for the treatment and/or prophylaxis of an abnormal cellular proliferation, such as tumors and cancer, in a host, preferably a human, comprising administering to the host a therapeutically effective amount of a compound of the present invention, in combination and/or alternation with one or more other effective antiproliferative agent, such as an antineoplastic agent, optionally in a pharmaceutically acceptable carrier.

The present invention also provides a use of a compound of the present invention, optionally in a pharmaceutically acceptable carrier, for the treatment and/or prophylaxis of a viral infection, and in particular a HBV, HCV or HIV infection, in a host, preferably a human.

The present invention also provides a use of a compound of the present invention, optionally in a pharmaceutically acceptable carrier, for the treatment and/or prophylaxis of an abnormal cellular proliferation, such as tumors and cancer, in a host, preferably a human.

The present invention also provides a use of a compound of the present invention, in combination and/or alternation with one or more other effective antiviral agent, and in particular an anti-HBV, anti-HCV or anti-HIV agent, optionally in a pharmaceutically acceptable carrier, for the treatment and/or prophylaxis of a viral infection, and in particular a HBV, HCV or HIV infection, in a host, preferably a human.

The present invention also provides a use of a compound of the present invention, in combination and/or alternation with one or more other effective antiproliferative agent, such as an antineoplastic agent, optionally in a pharmaceutically acceptable carrier, for the treatment and/or prophylaxis of an abnormal cellular proliferation, such as tumors and cancer, in a host, preferably a human.

The present invention also provides a use of a compound of the present invention, optionally in a pharmaceutically acceptable carrier, in the manufacture of a medicament for the treatment and/or prophylaxis of a viral infection, and in particular a HBV, HCV or HIV infection, in a host, preferably a human.

The present invention also provides a use of a compound of the present invention, optionally in a pharmaceutically acceptable carrier, in the manufacture of a medicament for the treatment and/or prophylaxis of an abnormal cellular proliferation, such as tumors and cancer, in a host, preferably a human.

The present invention also provides a use of a compound of the present invention, in combination and/or alternation with one or more other effective antiviral agent, and in particular an anti-HBV, anti-HCV or anti-HIV agent, optionally in a pharmaceutically acceptable carrier, in the manufacture of a medicament for the treatment and/or prophylaxis of a viral infection, and in particular a HBV, HCV or HIV infection, in a host, preferably a human.

The present invention also provides a use of a compound of the present invention, in combination and/or alternation with one or more other effective antiproliferative agent, such as an antineoplastic agent, optionally in a pharmaceutically acceptable carrier, in the manufacture of a medicament for the treatment and/or prophylaxis of an abnormal cellular proliferation, such as tumors and cancer, in a host, preferably a human.

The invention also provides synthetic methods useful for preparing the compounds of the invention, as well as intermediates disclosed herein that are useful in the preparation of the compounds of the present invention.

The invention as disclosed herein is method and composition for the treatment of HIV, hepatitis B or C, or abnormal cellular proliferation, in humans or other host animals, that includes administering a therapeutically effective amount of a β-D- or β-L-nucleoside derivatives, a pharmaceutically acceptable derivative, including a compound which has been alkylated or acylated on sugar or phosphonate moiety, or on the purine or pyrimidine, or a pharmaceutically acceptable salt thereof, optionally in a pharmaceutically acceptable carrier. The compounds of this invention either possess antiviral (i.e., anti-HIV-1, anti-HIV-2, anti-hepatitis B/C virus) activity or antiproliferative activity, or are metabolized to a compound that exhibits such activity. The invention as disclosed herein also includes the process for the preparation of such β-D- or β-L-nucleoside derivatives.

Stereoisomerism and Polymorphism

The compounds of the present invention may have asymmetric centers and occur as racemates, racemic mixtures, individual diastereomers or enantiomers, with all isomeric forms being included in the present invention. Compounds of the present invention having a chiral center may exist in and be isolated in optically active or racemic forms. Some compounds may exhibit polymorphism. The present invention encompasses racemic, optically-active, polymorphic, or stereoisomeric form, or mixtures thereof, of a compound of the invention, which possess the useful properties described herein. Optically active forms of the compounds can be prepared using any method known in the art, including but not limited to by resolution of the racemic form by recrystallization techniques, by synthesis from optically-active starting materials; by chiral synthesis, or by chromatographic separation using a chiral stationary phase or by enzymatic resolution.

DEFINITIONS

Listed below are definitions of various terms used to describe this invention. These definitions apply to the terms as they are used throughout this specification and claims, unless otherwise limited in specific instances, either individually or as part of a larger group.

The term "nucleobase," as used herein, refers to the base portion of a nucleoside or nucleotide. In some embodiments, a nucleobase is an optionally substituted aryl, optionally substituted aryl heteroaryl, or optionally substituted heterocyclic. In certain embodiments, a nucleobase is a heterocycle containing at least one nitrogen. In certain embodiments, a nucleobase is preferably a purine or pyrimidine base, as defined herein.

The term "purine" or "pyrimidine" base refers to, but is not limited to, adenine, $N^6$-alkylpurines, $N^6$-acylpurines (wherein acyl is C(O)(alkyl, aryl, alkylaryl, or arylalkyl)), $N^6$-benzylpurine, 6-halopurine, 6-vinylpurine, 6-acetylenic purine, 6-alkoxy purine, 6-alkylaminopurine, 6-alkylthio purine, $N^2$-alkylpurines, $N^2$-alkyl-6-thiopurines, thymine, cytosine, 5-fluorocytosine, 5-methylcytosine, 6-azapyrimidine, including 6-azacytosine, 2- and/or 4-mercaptopyrmidine, uracil, 5-halouracil, including 5-fluorouracil, 5-alkylpyrimidines, 5-benzylpyrimidines, 5-halopyrimidines, 5-vinylpyrimidine, 5-acetylenic pyrimidine, 5-acyl pyrimidine, 5-hydroxyalkyl purine, 5-amidopyrimidine, 5-cyanopyrimidine, 5-iodopyrimidine, 5-iodo-pyrimidine, 5-Br-vinyl pyrimidine, 6-Br-vinyl pyrimidine, 5-nitropyrimidine, $N^2$-alkylpurines, $N^2$-alkyl-6-thiopurines, 5-azacytidinyl, 5-azauracilyl, triazolopyridinyl, imidazolopyridinyl, pyrrolopyrimidinyl, pyrrolotriazine, and pyrazolopyrimidinyl. Purine bases include, but are not limited to, guanine, adenine, hypoxanthine, 7-deazaguanine, 7-fluoro-7-deazaguanine, 7-deazaadenine, 7-fluoro-7-deazaadenine, 3-deazaadenine, 8-azaadenine, 2,6-diaminopurine, 2-amino-6-chloropurine, 6-ethoxypurine, 6-cyclopropylaminopurine, 6-methoxylpurine and 6-chloropurine. Functional oxygen and nitrogen groups on the base can be protected as necessary or desired. Suitable protecting groups are well known to those skilled in the art, and include trimethylsilyl, dimethylhexylsilyl, t-butyldimethylsilyl, and t-butyldiphenylsilyl, trityl, alkyl groups, and acyl groups such as acetyl and propionyl, methanesulfonyl, and p-toluenesulfonyl.

The term "aryl," as used herein, refers to a mono- or polycyclic carbocyclic ring system including, but not limited to, phenyl, naphthyl, tetrahydronaphthyl, indanyl, and indenyl.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl.

In accordance with the invention, any of the aryls, substituted aryls, heteroaryls and substituted heteroaryls described herein, can be any aromatic group. Aromatic groups can be substituted or unsubstituted.

The terms "alkyl", as used herein, refers to saturated, straight- or branched-chain hydrocarbon radicals. Preferred alkyl groups include $C_1$-$C_4$-alkyl, $C_1$-$C_8$-alkyl, $C_1$-$C_{12}$-alkyl and $C_1$-$C_{20}$-alkyl groups which contain between one and four, one and eight, one and twelve or one and twenty carbon atoms, respectively. As used herein, the term "$C_1$-$C_{20}$-alkyl" embraces $C_1$-$C_4$-alkyl, $C_1$-$C_8$-alkyl, $C_1$-$C_{12}$-alkyl and $C_1$-$C_{20}$-alkyl groups. Examples of $C_1$-$C_8$ alkyl radicals include, but are not limited to, methyl, ethyl, propyl, isopropyl, n-butyl, tert-butyl, neopentyl, n-hexyl, heptyl and octyl radicals; and examples of $C_1$-$C_{12}$ alkyl radicals include, but are not limited to, ethyl, propyl, isopropyl, n-hexyl, octyl, decyl, dodecyl radicals.

The term "alkenyl" as used herein, refers to straight- or branched-chain hydrocarbon radicals having at least one carbon-carbon double bond by the removal of a single hydrogen atom. Preferred alkenyl groups include $C_2$-$C_4$-alkenyl, $C_2$-$C_8$-alkenyl, $C_2$-$C_{12}$-alkenyl and $C_2$-$C_{20}$-alkenyl groups which contain between two and four, two and eight, two and twelve or two and twenty carbon atoms, respectively. As used herein, the term "$C_2$-$C_{20}$-alkenyl" embraces $C_2$-$C_4$-alkenyl, $C_2$-$C_8$-alkenyl, $C_2$-$C_{12}$-alkenyl and $C_2$-$C_{20}$-alkenyl groups. Alkenyl groups include, but are not limited to, for example, ethenyl, propenyl, butenyl, 1-methyl-2-buten-1-yl, heptenyl, octenyl, and the like.

The term "alkynyl" as used herein, refers to straight- or branched-chain hydrocarbon radicals containing having at least one carbon-carbon triple bond by the removal of a single hydrogen atom. Preferred alkynyl groups include $C_2$-$C_4$-alkynyl, $C_2$-$C_8$-alkynyl, $C_2$-$C_{12}$-alkynyl and $C_2$-$C_{20}$-alkynyl groups which contain between two and four, two and eight, two and twelve or two and twenty carbon atoms, respectively. As used herein, the term "$C_2$-$C_{20}$-alkynyl" embraces $C_2$-$C_4$-alkynyl, $C_2$-$C_8$-alkynyl, $C_2$-$C_{12}$-alkynyl and $C_2$-$C_{20}$-alkynyl groups. Representative alkynyl groups include, but are not limited to, for example, ethynyl, 1-propynyl, 1-butynyl, heptynyl, octynyl, and the like.

The term "$C_3$-$C_8$-cycloalkyl", or "$C_3$-$C_{12}$-cycloalkyl," as used herein, refers to a monocyclic or polycyclic saturated carbocyclic ring compound. Examples of $C_3$-$C_8$-cycloalkyl include, but not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, bicyclo[2.2.1]heptyl, and bicyclo[2.2.2]octyl.

The terms "$C_2$-$C_8$ alkylene," or "$C_2$-$C_8$ alkenylene," as used herein, refer to saturated or unsaturated respectively, straight- or branched-chain hydrocarbon di-radicals containing between two and eight carbon atoms, while the diradical may reside at the same or different carbon atoms.

The term "$C_3$-$C_8$ cycloalkenyl", or "$C_3$-$C_{12}$ cycloalkenyl" as used herein, refers to monocyclic or polycyclic carbocyclic ring compound having at least one carbon-carbon double bond. Examples of $C_3$-$C_8$ cycloalkenyl include, but not limited to, cyclopropenyl, cyclobutenyl, cyclopentenyl, cyclohexenyl, cycloheptenyl, cyclooctenyl, and the like; and examples of $C_3$-$C_{12}$ cycloalkenyl include, but not limited to, cyclopropenyl, cyclobutenyl, cyclopentenyl, cyclohexenyl, cycloheptenyl, cyclooctenyl, and the like.

It is understood that any alkyl, alkenyl, alkynyl and cycloalkyl moiety described herein can also be an aliphatic group, an alicyclic group or a heterocyclic group. An "aliphatic" group is a non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted.

The term "alicyclic," as used herein, denotes a monovalent group derived from a monocyclic or bicyclic saturated carbocyclic ring compound by the removal of a single hydrogen atom. Examples include, but not limited to, cyclopropyl, cyclobutyl, cyclopentyl, cyclohexyl, bicyclo[2.2.1]heptyl, and bicyclo[2.2.2]octyl. Such alicyclic groups may be further substituted.

The terms "heterocyclic" or "heterocycloalkyl" can be used interchangeably and referred to a non-aromatic ring or a bi- or tri-cyclic group fused system, where (i) each ring system contains at least one heteroatom independently selected from oxygen, sulfur and nitrogen, (ii) each ring system can be saturated or unsaturated, (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted. Representative heterocyclic groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl. Such heterocyclic groups may be further substituted.

The term "substituted" refers to substitution by independent replacement of one, two, or three or more of the hydrogen atoms thereon with substituents including, but not limited to, —F, —Cl, —Br, —I, —OH, protected hydroxy, —$NO_2$, —$N_3$, —CN, —$NH_2$, protected amino, oxo, thioxo, alkyl, alkenyl, alkynyl, cycloalkyl, heterocycloalkyl, aryl, heteroaryl, —NH—$C_1$-$C_{12}$-alkyl, —NH—$C_2$-$C_8$-alkenyl, —NH—$C_2$-$C_8$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_8$-alkenyl, —O—$C_2$-$C_8$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_8$-alkenyl, —CONH—$C_2$-$C_8$-alkynyl, —CONH—$C_3$-$C_{12}$-cycloalkyl, —CONH-aryl, —CONH-heteroaryl, —CONH-heterocycloalkyl, —$OCO_2$—$C_1$-$C_{12}$-alkyl, —$OCO_2$—$C_2$-$C_8$-alkenyl, —$OCO_2$—$C_2$-$C_8$-alkynyl, —$OCO_2$—$C_3$-$C_{12}$-cycloalkyl, —$OCO_2$-aryl, —$OCO_2$-heteroaryl, —$OCO_2$-heterocycloalkyl, —$OCONH_2$, —OCONH—$C_1$-$C_{12}$-alkyl, —OCONH—$C_2$-$C_8$-alkenyl, —OCONH—$C_2$-$C_8$-alkynyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_8$-alkenyl, —NHC(O)—$C_2$-$C_8$-alkynyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_8$-alkenyl, —$NHCO_2$—$C_2$-$C_8$-alkynyl, —$NHCO_2$—$C_3$-$C_{12}$-cycloalkyl, —$NHCO_2$-aryl, —$NHCO_2$-heteroaryl, —$NHCO_2$-heterocycloalkyl, —$NHC(O)NH_2$, —NHC(O)NH—$C_1$-$C_{12}$-alkyl, —NHC(O)NH—$C_2$-$C_8$-alkenyl, —NHC(O)NH—$C_2$-$C_8$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, $NHC(S)NH_2$, —NHC(S)NH—$C_1$-$C_{12}$-alkyl, —NHC(S)NH—$C_2$-$C_8$-alkenyl, —NHC(S)NH—$C_2$-$C_8$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —$NHC(NH)NH_2$, —NHC(NH)NH—$C_1$-$C_{12}$-alkyl, —NHC(NH)NH—$C_2$-$C_8$-alkenyl, —NHC(NH)NH—$C_2$-$C_8$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_8$-alkenyl, —NHC(NH)—$C_2$-$C_8$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_8$-alkenyl, —C(NH)NH—$C_2$-$C_8$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_8$-alkenyl, —S(O)—$C_2$-$C_8$-alkynyl, —S(O)—$C_3$-$C_{12}$-cycloalkyl, —S(O)-aryl, —S(O)-heteroaryl, —S(O)-heterocycloalkyl —$SO_2NH_2$, —$SO_2NH$—$C_1$-$C_{12}$-alkyl, —$SO_2NH$—$C_2$-$C_8$-alkenyl, —$SO_2NH$—$C_2$-$C_8$-alkynyl, —$SO_2NH$—$C_3$-$C_{12}$-cycloalkyl, —$SO_2NH$-aryl, —$SO_2NH$-heteroaryl, —$SO_2NH$-heterocycloalkyl, —$NHSO_2$—$C_1$-$C_{12}$-alkyl, —$NHSO_2$—$C_2$-$C_8$-alkenyl, —$NHSO_2$—$C_2$-$C_8$-alkynyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_8$-alkenyl, —S—$C_2$-$C_8$-alkynyl, —S—$C_3$-$C_{12}$-cycloalkyl, —S-aryl, —S-heteroaryl, —S-heterocycloalkyl, or methylthiomethyl. It is understood that the aryls, heteroaryls, alkyls, and the like can be further substituted.

The term "halogen," as used herein, refers to an atom selected from fluorine, chlorine, bromine and iodine.

The term "hydroxy activating group", as used herein, refers to a labile chemical moiety which is known in the art to activate a hydroxyl group so that it will depart during synthetic procedures such as in a substitution or an elimination reactions. Examples of hydroxyl activating group include, but not limited to, mesylate, tosylate, triflate, p-nitrobenzoate, phosphonate and the like.

The term "activated hydroxy", as used herein, refers to a hydroxy group activated with a hydroxyl activating group, as defined above, including mesylate, tosylate, triflate, p-nitrobenzoate, phosphonate groups, for example.

The term "hydroxy protecting group" or "thiol protecting group," as used herein, refers to a labile chemical moiety which is known in the art to protect a hydroxyl group or thiol against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis,* 3rd edition, John Wiley & Sons, New York (1999). Examples of hydroxyl protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl(trityl), tetrahydrofuryl, methoxymethyl, methylthiomethyl, benzyloxymethyl, 2,2,2-trichloroethoxymethyl, 2-(trimethylsilyl)ethoxymethyl, methanesulfonyl, para-toluene-sulfonyl, trimethylsilyl, triethylsilyl, triisopropylsilyl, and the like. Preferred hydroxyl protecting groups for the present invention are acetyl (Ac or —C(O)$CH_3$), benzoyl (Bz or —C(O)$C_6H_5$), and trimethylsilyl (TMS or —Si($CH_3$)$_3$).

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group", as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery*, (Drugs and the Pharmaceutical Sciences; Volume 53), Marcel Dekker, Inc., New York (1992).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis,* 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

The term "amino acid" refers to naturally occurring and synthetic α, β, γ, or δ amino acids, and includes but is not limited to, amino acids found in proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In certain embodiments, the amino acid is in the L-configuration. In certain embodiments, the amino acid is in the D-configuration. In certain embodiments, the amino acid is provided as a substituent of a compound described herein, wherein the amino acid is a residue selected from the group consisting of alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl and β-histidinyl. Preferably, the amino acid residue is connected to the rest of the molecule via an ester or amide bond.

The term "amino acid derivative" refers to a group derivable from a naturally or Non-naturally occurring amino acid, as described and exemplified herein. Amino acid derivatives are apparent to those of skill in the art and include, but are not limited to, ester, amino alcohol, amino aldehyde, amino lactone, and N-methyl derivatives of naturally and non-naturally occurring amino acids. In an embodiment, an amino acid derivative is provided as a substituent of a compound described herein, wherein the substituent is —NR$^u$-G(S$_c$)—C(O)-Q$^1$, wherein Q$^1$ is —SR$^v$, —NR$^v$R$^v$ or alkoxyl, R$^v$ is hydrogen or alkyl, S$_c$ is a side-chain of a naturally occurring or non-naturally occurring amino acid, G is C$_1$-C$_2$ alkyl, and R$^u$ is hydrogen; or R$^u$ and S$_c$ are taken together with the atoms to which they are attached to form a five-membered heterocyclic ring. In an embodiment, an amino acid derivative is provided as a substituent of a compound described herein, wherein the substituent is —O—C(O)-G(S$_c$)—NH-Q$^2$, wherein Q$^2$ is hydrogen or alkoxyl, S$_c$ is a side-chain of a naturally occurring or non-naturally occurring amino acid and G is C$_1$-C$_2$ alkyl. In certain embodiments, Q$^2$ and S$_c$ are taken together with the atoms to which they are attached to form a five-membered heterocyclic ring. In certain embodiments, G is an optionally substituted methylene and S$_c$ is selected from the group consisting of hydrogen, alkyl, arylalkyl, heterocycloalkyl, carboxylalkyl, heteroarylalkyl, aminoalkyl, hydroxylalkyl, aminoiminoaminoalkyl, aminocarbonylalkyl, sulfanylalkyl, carbamoylalkyl, alkylsulfanylalkyl and hydroxylarylalkyl. In an embodiment, an amino acid derivative is provided as a substituent of a compound described herein, wherein the amino acid derivative is in the D-configuration. In an embodiment, an amino acid derivative is provided as a substituent of a compound described herein, wherein the amino acid derivative is in the L-configuration.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "protected amino," as used herein, refers to an amino group protected with an amino protecting group as defined above.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, N Y, 1986.

The term "protic solvent' as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, N Y, 1986.

The term "hydrogen" includes deuterium and the listing of hydrogen and deuterium in the alternative with respect to some variables is not intended to infer or imply that other hydrogens are not intended to envision deuterium. In general, the identification of an element embraces the isotopes of the element, as suitable for the preparation a pharmaceutical.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the Formula herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, $2^{nd}$ Ed. Wiley-VCH (1999); T. W. Greene and P. G. M. Wuts, *Protective Groups in Organic Synthesis*, 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The term "subject" as used herein refers to an animal. Preferably the animal is a mammal. More preferably the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentane-propionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a pharmaceutically acceptable salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to a compound of the invention. Various forms of prodrugs are known in the art, for example, as discussed in Bundgaard, (ed.), Design of Prodrugs, Elsevier (1985); Widder, et al. (ed.), Methods in Enzymology, Vol. 4, Academic Press (1985); Krogsgaard-Larsen, et al., (ed). "Design and Application of Prodrugs, Textbook of Drug Design and Development, Chapter 5, 113-191 (1991); Bundgaard, et al., *Journal of Drug Deliver Reviews,* 8:1-38(1992); Bundgaard, *J. of Pharmaceutical Sciences,* 77:285 et seq. (1988); Higuchi and Stella (eds.) Prodrugs as Novel Drug Delivery Systems, American Chemical Society (1975); Bernard Testa & Joachim Mayer, "Hydrolysis In Drug And Prodrug Metabolism: Chemistry, Biochemistry And Enzymology," John Wiley and Sons, Ltd. (2002); and J. Rautio et al., "Prodrugs: design and clinical applications", *Nature Review—Drug Discovery,* 7, 255-270 (2008).

The present invention also relates to solvates of the compounds of Formula (I), for example hydrates.

This invention also encompasses pharmaceutical compositions containing, and methods of treating viral infections through administering, pharmaceutically acceptable prodrugs of compounds of the invention. For example, compounds of the invention having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the invention. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyl-oxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to a compound of the invention, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the compound of the invention.

Solid dosage forms for oral administration include capsules, tablets, pills, powders, and granules. In such solid dosage forms, compound of the invention is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to a compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of a compound of the invention prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al., and WO 98/43650 by Montgomery, all of which are incorporated herein by reference). A discussion of pulmonary delivery of antibiotics is also found in U.S. Pat. No. 6,014,969, incorporated herein by reference.

According to the methods of treatment of the present invention, viral infections, conditions are treated or prevented in a patient such as a human or another animal by administering to the patient a therapeutically effective amount of a compound of the invention, in such amounts and for such time as is necessary to achieve the desired result.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). A therapeutically effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the invention described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of a therapeutically effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically excipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

When the compositions of this invention comprise a combination of a compound of the invention described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The said "additional therapeutic or prophylactic agents" includes but not limited to, immune therapies (eg. interferon), therapeutic vaccines, antifibrotic agents, anti-inflammatory agents such as corticosteroids or NSAIDs, bronchodilators such as beta-2 adrenergic agonists and xanthines (e.g. theophylline), mucolytic agents, anti-muscarinics, anti-leukotrienes, inhibitors of cell adhesion (e.g. ICAM antagonists), anti-oxidants (e.g. N-acetylcysteine), cytokine agonists, cytokine antagonists, lung surfactants and/or antimicrobial and anti-viral agents (e.g. ribavirin and amantidine). The compositions according to the invention may also be used in combination with gene replacement therapy.

Unless otherwise defined, all technical and scientific terms used herein are accorded the meaning commonly known to one of ordinary skill in the art. All publications, patents, published patent applications, and other references mentioned herein are hereby incorporated by reference in their entirety.

Pharmaceutically Acceptable Derivatives

The compound of the present invention can be administered as any derivative that upon administration to the recipient, is capable of providing directly or indirectly, the parent compound. Further, the modifications can affect the biological activity of the compound, in some cases increasing the activity over the parent compound. This can easily be assessed by preparing the derivative and testing its antiviral and anti-proliferative activity according to the methods described herein, or other method known to those skilled in the art.

In cases where compounds are sufficiently basic or acidic to form stable nontoxic acid or base salts, administration of the compound as a pharmaceutically acceptable salt may be appropriate. Examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, α-ketoglutarate and α-glycerophosphate. Suitable inorganic salts may also be formed, including sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Any of the nucleosides described herein can be administrated as a nucleotide prodrug to increase the activity, bioavailability, stability or otherwise alter the properties of the nucleoside. A number of nucleotide prodrug ligands are known. In general, alkylation, acylation or other lipophilic modification of the mono, di or triphosphate of the nucleoside will increase the stability of the nucleotide. Examples of substituent groups that can replace one or more hydrogens on the phosphate moiety are alkyl, aryl, steroids, carbohydrates, including sugars, 1,2-diacylglycerol and alcohols. Many are described in R. Jones and N. Bischofberger, *Antiviral Research*, 27 (1995) 1-17. Any of these can be used in combination with the disclosed nucleosides to achieve a desired effect.

The active nucleoside can also be provided as a 5'-phosphoether lipid or a 5'-ether lipid, as disclosed in the following references, which are incorporated by reference herein: Kucera, L. S. et al., 1990. "Novel membrane interactive ether lipid analogs that inhibit infectious HIV-1 production and induce defective virus formation." *AIDS Res. Hum. Retro Viruses.* 6:491-501; Piantadosi, C., J. et al., 1991. "Synthesis and evaluation of novel ether lipid nucleoside conjugates for anti-HIV activity." *J. Med. Chem.* 34:1408.1414; Hosteller, K. Y. et al., 1992. "Greatly enhanced inhibition of human immunodeficiency virus type 1 replication in CEM and HT4-6C cells by 3'-deoxythymidine diphosphate dimyristoylglycerol, a lipid prodrug of 3'-deoxythymidine." *Antimicrob. Agents Chemother.* 36:2025.2029; Hostetler, K. Y., et al., 1990. "Synthesis and antiretroviral activity of phospholipid analogs of azidothymidine and other antiviral nucleosides." *J. Biol. Chem.* 265:61127.

Nonlimiting examples of U.S. patents that disclose suitable lipophilic substituents that can be covalently incorporated into the nucleoside, preferably at the 5'-OH position of the nucleoside or lipophilic preparations, include U.S. Pat. No. 5,149,794 (Sep. 22, 1992, Yatvin et al.); U.S. Pat. No. 5,194,654 (Mar. 16, 1993, Hostetler et al., U.S. Pat. No. 5,223,263 (Jun. 29, 1993, Hostetler et al.); U.S. Pat. No. 5,256,641 (Oct. 26, 1993, Yatvin et al.); U.S. Pat. No. 5,411,947 (May 2, 1995, Hostetler et al.); U.S. Pat. No. 5,463,092 (Oct. 31, 1995, Hostetler et al.); U.S. Pat. No. 5,543,389 (Aug. 6, 1996, Yatvin et al.); U.S. Pat. No. 5,543,390 (Aug. 6, 1996, Yatvin et al.); U.S. Pat. No. 5,543,391 (Aug. 6, 1996, Yatvin et al.); and U.S. Pat. No. 5,554,728 (Sep. 10, 1996; Basava et al.), all of which are incorporated herein by reference. Foreign patent publications that disclose lipophilic substituents that can be attached to the nucleosides of the present invention, or lipophilic preparations, include WO 89/02733, WO 90/00555, WO 91/16920, WO 91/18914, WO 93/00910, WO 94/26273, WO 96/15132, EP 0 350 287, and WO 91/19721.

Nonlimiting examples of nucleotide prodrugs are described in the following references: J. K. Dickson, Jr. et al., "Orally active squalene synthetase inhibitors: bis((acyloxy)alkyl) prodrugs of the α-phosphonosylfonic acid moiety" *J. Med. Chem.* 1996, 39, 661-664; T. Kurz, et al., "Synthesis and antimalarial activity of chain substituted pivaloyloxymethyl ester analogues of Fosmidomycin and FR900098" *Bioorg. Med. Chem.* 2006, 14, 5121-5135; J. E. Starrett, Jr. et al., "Synthesis, oral bioavilability determination, and in vitro evaluation of prodrugs of the antiviral agent 9-[2-(phosphonomethoxy)ethyl]adenine (PMEA)" *J. Med. Chem.* 1994, 37, 1857-1864; H. T. Serafinowska, et al., "Synthesis and in vivo evaluation of prodrugs of 9-[2-(phosphonomethoxy)ethoxy]adenine" *J. Med. Chem.* 1995, 38, 1372-1379; S. Benzaria, et al, "Synthesis, in vitro antiviral evaluation, and stability studies of bis(S-acyl-2-thioethyl) ester derivatives of 9-[2-(phosphonomethoxy) ethyl]adenine (PMEA) as potential PMEA prodrugs with improved oral bioavailability" *J. Med. Chem.* 1996, 39, 4958-4965; M. S. Louie and H. Chapman, "An efficient process for the synthesis of cyclic HPMPC" *Nucleosides, Nucleotides Nucleic acid* 2001, 20, 1099-1102; J.-R. Choi, et al., "A novel class of phosphonate nucleosides. 9-[(1-phosphonomethoxy)-cyclopropyl)methyl]-guanine as a potent and selective anti-HBV agent" *J. Med. Chem.* 2004, 47, 2864-2869; M. Wu, et al, "Synthesis of 9-[1-(substituted)-3-(phosphonomethoxy)propyl]adenine derivatives as possible antiviral agents" *Nucleosides, Nucleotides Nucleic acid.* 2005, 24, 1543-1568; X. Fu, et al., "Design and synthesis of novel bis(L-amino acid) ester prodrugs of 9-[2-(phosphonomethoxy)ethyl]adenine (PMEA) with improved anti-HBV activity" *Bioorg. Med. Chem. Lett.* 2007, 17, 465-470.

Similarly, the 5'-phosphonate can also be provided as various phosphonate prodrug to increase the activity, bioavailability, stability or otherwise alter the properties of the phosphonate. A number of phosphonate prodrug ligands are known. In general, alkylation, acylation or other lipophilic modification of one or more hydroxy on the phosphonate moiety can be used to achieve a desired effect.

Combination and Alternation Therapy for HIV, HBV or HCV

It has been recognized that drug-resistant variants of HIV, HBV and HCV can emerge after prolonged treatment with an antiviral agent. Drug resistance most typically occurs by mutation of a gene that encodes for a protein such as an enzyme used in viral replication, and most typically in the case of HIV, reverse transcriptase, protease, or DNA polymerase, and in the case of HBV, DNA polymerase, or in the case of HCV, RNA polymerase, protease, or helicase. Recently, it has been demonstrated that the efficacy of a drug against HIV infection can be prolonged, augmented, or restored by administering the compound in combination or alternation with a second, and perhaps third, antiviral compound that induces a different mutation from that caused by the principle drug. Alternatively, the pharmacokinetics, bio-distribution, or other parameter of the drug can be altered by such combination or alternation therapy. In general, combination therapy is typically preferred over alternation therapy because it induces multiple simultaneous stresses on the virus.

The second antiviral agent for the treatment of HIV, in one embodiment, can be a reverse transcriptase inhibitor (a "RTI"), which can be either a synthetic nucleoside (a "NRTI") or a non-nucleoside compound (a "NNRTI"). In an alternative embodiment, in the case of HIV, the second (or third) antiviral agent can be a protease inhibitor. In other embodiments, the second (or third) compound can be a pyrophosphate analog, or a fusion binding inhibitor. A list compiling resistance data collected in vitro and in vivo for a number of antiviral compounds is found in Schinazi, et al, Mutations in retroviral genes associated with drug resistance, *International Antiviral News*, 1997.

Preferred compounds for combination or alternation therapy for the treatment of HBV include 3TC, FTC, L-FMAU, interferon, adefovir dipivoxil, entecavir, telbivudine (L-dT), valtorcitabine (3'-valinyl L-dC), β-D-dioxolanyl-guanine (DXG), β-D-dioxolanyl-2,6-diaminopurine (DAPD), and β-D-dioxolanyl-6-chloropurine (ACP), famciclovir, penciclovir, lobucavir, ganciclovir, and ribavirin.

Preferred examples of antiviral agents that can be used in combination or alternation with the compounds disclosed herein for HIV therapy include cis-2-hydroxymethyl-5-(5-fluorocytosin-1-yl)-1,3-oxathiolane (FTC); the (−)-enantiomer of 2-hydroxymethyl-5-(cytosin-1-yl)-1,3-oxathiolane (3TC); ziagen (abacavir), emtriva, viread (tenofovir DF), carbovir, acyclovir, foscarnet, interferon, AZT, DDI, D4T, CS-87 (3'-azido-2',3'-dideoxyuridine), and β-D-dioxolane nucleosides such as β-D-dioxolanyl-guanine (DXG), β-D-dioxolanyl-2,6-diaminopurine (DAPD), and β-D-dioxolanyl-6-chloropurine (ACP), and integrase inhibitors such as MK-0518.

Preferred protease inhibitors (PIs) include crixivan (indinavir), viracept (nelfinavir), norvir (ritonavir), invirase (saquinavir), aptivus (tipranavir), kaletra, lexiva (fosamprenavir), reyataz (atazanavir) and TMC-114.

Preferred Non-Nucleoside Reverse Transcriptase Inhibitors (NNRTIs) include rescripton (delavirdine), sustiva (efavirenz), viramune (nevirapine) and TMC-125.

Preferred Entry inhibitors include fuzeon (T-20), PRO-542, TNX-355, vicriviroc, aplaviroc and maraviroc.

A more comprehensive list of compounds that can be administered in combination or alternation with any of the disclosed nucleosides include (1S,4R)-4-[2-amino-6-cyclopropyl-amino)-9H-purin-9-yl]-2-cyclopentene-1-methanol succinate ("1592", a carbovir analog; GlaxoWellcome); 3TC: (−)-β-L-2',3'-dideoxy-3'-thiacytidine (GlaxoWellcome); a-APA R18893: a-nitro-anilino-phenylacetamide; A-77003; C2 symmetry-based protease inhibitor (Abbott); A-75925: C2 symmetry-based protease inhibitor (Abbott); AAP-BHAP: bishetero-arylpiperazine analog (Upjohn); ABT-538: C2-symmetry-based protease inhibitor (Abbott); AzddU: 3'-azido-2',3'-dideoxyuridine; AZT: 3'-azido-3'-deoxythymidine (GlaxoWellcome); AZT-p-ddI: 3'-azido-3'-deoxythymidilyl-(5',5')-2',3'-dideoxyinosinic acid (Ivax); BHAP: bisheteroaryl-piperazine; BILA 1906: N-{1S-[[[3-[2S-{(1,1-dimethylethyl)amino]carbonyl}-4R]-3-pyridinylmethyl)thio]-1-piperidinyl]-2R-hydroxy-1S-(phenylmethyl)-propyl]amino]-carbonyl]-2-methylpropyl}-2-quinolinecarboxamide (Bio Mega/Boehringer-Ingelheim); BILA 2185: N-(1,1-dimethylethyl)-1-[2S-[[2-2,6-dimethyphenoxy)-1-xoethyl]amino]-2R-hydroxy-4-phenylbutyl]-4R-pyridinylthio)-2-piperidinecarboxamide (BioMega/Boehringer-Ingelheim); BMS 186,318: aminodiol derivative HIV-1 protease inhibitor (Bristol-Myers-Squibb); d4API: 9-[2,5-d]hydro-5-(phosphonomethoxy)-2-furanyladenine (Gilead); d4C: 2',3'-didehydro-2',3'-dideoxycytidined; d4T: 2',3'-didehydro-3'-deoxythymidine (Bristol-Myers-Squibb); ddC: 2',3'-dideoxycytidine (Roche); ddI: 2',3'-dideoxyinosine (Bristol-Myers-Squibb); DMP-266: a 1,4-dihydro-2H-3,1-benzoxazin-2-one; DMP-450: {[4R-(4-a,5-a,6-b,7-b)]-hexahydro-5,6-bis(hydroxy)-1,3-bis(3-amino)phenyl]-methyl)-4,7-bis-(phenylmethyl)-2H-1,3-diazepin-2-one}-bismesylate (Gilead); DXG: (−)-β-D-dioxolane-guanosine (Gilead); EBU-dM: 5-ethyl-1-ethoxymethyl-6-(3,5-dimethylbenzyl)-uracil; E-EBU: 5-ethyl-1-ethoxymethyl-6-benzyluracil; DS: dextran sulfate; E-EPSeU: 1-(ethoxymethyl)-(6-phenyl-selenyl)-5-ethyluracil; E-EPU: 1-(ethoxymethyl)-(6-phenylthio)-5-ethyluracil; FTC: β-2',3'-dideoxy-5-fluoro-3'-thiacytidine (Gilead); HBY097: S-4-isopropoxycarbonyl-6-methoxy-3-(methylthio-methyl)-3,4-dihydroquinoxalin-2 (1H)-thione; HEPT: 1-[(2-hydroxyethoxy)-methyl]-6-(phenylthio)thymine; HIV-1: human immunodeficiency virus type 1; JM2763: 1,1'-(1,3-propanediyl)-bis-1,4,8,11-tetraaza-cyclotetradecane (Johnson Matthey); JM3100: 1,1'-[1,4-phenylenebis-(methylene)]-bis-1,4,8,11-tetraazacyclotetradecane (Johnson Matthey); KNI-272: (2S,3S)-3-amino-2-hydroxy-4-phenylbutyric acid-containing tripeptide; L-697,593; 5-ethyl-6-methyl-3-(2-phthalimido-ethyl)pyridin-2(1H)-one; L-735,524: hydroxy-amino-pentane amide HIV-1 protease inhibitor (Merck); L-697,661: 3-{[(4,7-dichloro-1,3-benzoxazol-2-yl)methyl]amino}-5-ethyl-6-methylpyridin-2(1H)-one; L-FDDC: (−)-β-L-5-fluoro-2',3'-dideoxycytidine; L-FDOC: (−)-β-L-fluoro-dioxolane cytosine; MKC442: 6-benzyl-1-ethoxymethyl-5-isopropyluracil (1-EBU; Mitsubishi); Nevirapine: 11-cyclopropyl-5,11-dihydro-4-methyl-6H-dipyridol-[3,2-b:2',3'-e]-diazepin-6-one (Boehringer-Ingelheim); NSC648400: 1-benzyloxymethyl-5-ethyl-6-(alpha-pyridylthio)uracil (E-BPTU); P9941: [2-pyridylacetyl-IlePheAla-y(CHOH)]$_2$ (Dupont Merck); PFA: phosphonoformate (foscamet; Astra); PMEA: 9-(2-phosphonylmethoxyethyl)adenine (Gilead); PMPA: (R)-9-(2-phosphonylmethoxypropyl)adenine (Gilead); Ro 31-8959: hydroxyethylamine derivative HIV-1 protease inhibitor (Roche); RPI-312: peptidyl protease inhibitor, 1-[(3S)-3-(n-alpha-benzyloxycarbony 1)-1-asparginyl)-amino-2-hydroxy-4-phenylbutyryl]-n-tert-1-proline amide; 2720: 6-chloro-3,3-dimethyl-4-(isopropenyloxycarbonyl)-3,4-dihydro-quinoxalin-2-(1H)-thione; SC-52151: hydroxy-ethylurea isostere protease inhibitor (Searle); SC-55389A: hydroxyethyl-urea isostere protease inhibitor (Searle); TIBO R82150: (+)-(5S)-4,5,6,7-tetrahydro-5-methyl-6-(3-methyl-2-butenyl)-imidazo[4,5,1-jk]-[1,4]benzodiazepin-2(1H)-thione (Janssen); TIBO 82913: (+)-(5s)-4,5,6,7,-tetrahydro-9-chloro-5-methyl-6-(3-methyl-2-butenyl)imidazo[4,5,1jk]-[1,4]benzo-diazepin-2 (1H)-thione (Janssen); TSAO-m3T: [2',5'-bis-O-(tert-butyl-dimethylsilyl)-3'-spiro-5'-(4'-amino-1',2'-oxathiole-2',2'-dioxide)]-β-D-pento-furanosyl-N3-methylthymine; U90152: 1-[3-[(1-methylethyl)-amino]-2-pyridinyl]-4-[[5-[(methylsulphonyl)-amino]-1H-indol-2-yl]carbonyl]piperazine; UC: thiocarboxanilide derivatives (Uniroyal); UC-781: N-[4-chloro-3-(3-methyl-2-butenyloxy)phenyl]-2-methyl-3-furancarbothioamide; UC-82: N-[4-chloro-3-(3-methyl-2-butenyloxy)phenyl]-2-methyl-3-thiophenecarbothioamide; VB 11,328: hydroxyethyl-sulphonamide protease inhibitor (Vertex); VX-478: hydroxyethylsulphonamide protease inhibitor (Vertex); XM 323: cyclic urea protease inhibitor (Dupont Merck).

The compound of the invention can also be administered in combination or alternation with ribavarin, interferon, interleukin or a stabilized prodrug of any of them. More broadly described, the compound can be administered in combination or alternation with any of the anti-HCV drugs listed below.

Table of anti-Hepatitis C Compounds in Current Clinical Development

| Drug name | Drug category | Pharmaceutical Company |
|---|---|---|
| PEGASYS pegylated interferon alfa-2a | Long acting interferon | Roche |
| INFERGEN interferon alfacon-1 | Long acting interferon | InterMune |
| OMNIFERON natural interferon | Long acting interferon | Viragen |
| ALBUFERON | Long acting interferon | Human Genome Sciences |
| REBIF interferon beta-la | Interferon | Ares-Serono |
| Interferon lambda | Interferon | BMS |
| Omega Interferon | Interferon | BioMedicine |
| Oral Interferon alpha | Oral Interferon | Amarillo Biosciences |
| Interferon gamma-lb | Anti-fibrotic | InterMune |
| IP-501 | Anti-fibrotic | InterMune |
| Merimebodib VX-497 | IMPDH inhibitor (inosine monophosphate dehydrogenase) | Vertex |
| AMANTADINE (Symmetrel) | Broad Antiviral Agent | Endo Labs Solvay |
| IDN-6556 | Apotosis regulation | Idun Pharma. |
| XTL-002 | Monoclonal Antibody | XTL |
| HCV/MF59 | Vaccine | Chiron |
| CIVACIR | Polyclonal Antibody Therapeutic vaccine | NABI Innogenetics |
| VIRAMIDINE | Nucleoside Analogue | ICN |
| ZADAXIN (thymosin alfa-1) | Immunomodulator | Sci Clone |
| CEPLENE (histamine) | Immunomodulator | Maxim |
| VX 950/LY 570310 | Protease inhibitor | Vertex/Eli Lilly |
| ISIS 14803 | Antisense | Isis Pharmaceutical/Elan |
| IDN-6556 | Caspase inhibitor | Idun Pharmaceuticals |
| JTK 003 | Polymerase Inhibitor | AKROS Pharma |
| Tarvacin | Anti-Phospholipid Therapy | Peregrine |

Table of anti-Hepatitis C Compounds in Current Clinical Development

| Drug name | Drug category | Pharmaceutical Company |
|---|---|---|
| HCV-796 | Polymerase Inhibitor | ViroPharma/Wyeth |
| CH-6 | Protease inhibitor | Schering |
| ANA971 | Isatoribine | ANADYS |
| ANA245 | Isatoribine | ANADYS |
| CPG 10101 (Actilon) | Immunomodulator | Coley |
| Rituximab (Rituxam) | Anti-CD2O Monoclonal Antibody | Genetech/IDEC |
| NM283 (Valopicitabine) | Polymerase Inhibitor | Idenix Pharmaceuticals |
| HEPX ™-C | Monoclonal Antibody | XTL |
| IC41 | Therapeutic Vaccine | Intercell |
| Medusa Interferon | Longer acting interferon | Flamel Technology |
| E-1 | Therapeutic Vaccine | Innogenetics |
| Multiferon | Long Acting Interferon | Viragen |
| BILN 2061 | Protease inhibitor | Boehringer-Ingelheim |
| TMC435350 | Protease inhibitor | Tibotec/Medivir |
| Telaprevir (VX-950) | Protease inhibitor | Vertex |
| Boceprevir (SCH 503034) | Protease inhibitor | Schering-Plough |
| ACH-1625 | Protease inhibitor | Achillion |
| ACH-2684 | Protease inhibitor | Achillion |
| ABT-450 | Protease inhibitor | Abbott/Enanta |
| BI-201335 | Protease inhibitor | Boehringer-Ingelheim |
| PHX-1766 | Protease inhibitor | Phenomix |
| VX-500 | Protease inhibitor | Vertex |
| MK-7009 | protease inhibitor | Merck |
| MK-5172 | protease inhibitor | Merck |
| R7227 (ITMN-191) | protease inhibitor | InterMune |
| Narlaprevir (SCH 900518) | Protease inhibitor | Schering/Merck |
| BI201335 | Protease inhibitor | Boehringer-Ingelheim |
| BMS-650032 | Protease inhibitor | BMS |
| GS-9256 | Protease inhibitor | Gilead |
| GS-9451 | Protease inhibitor | Gilead |
| Alinia (nitazoxanide) | To be determined | Romark |
| ABT-072 | Polymerase Inhibitor | Abbott |
| ABT-333 | Polymerase Inhibitor | Abbott |
| Filibuvir (PF-00868554) | Polymerase Inhibitor | Pfizer |
| VCH-916 | Polymerase Inhibitor | Vertex |
| R7128 (PSI6130) | Polymerase Inhibitor | Roche/Pharmasset |
| IDX184 | Polymerase Inhibitor | Idenix |
| INX-189 | Polymerase Inhibitor | Inhibitex |
| GS-7977 | Polymerase Inhibitor | Gilead |
| PSI-938 | Polymerase Inhibitor | Pharmasset |
| R1626 | Polymerase inhibitor | Roche |
| MK-3281 | Polymerase inhibitor | Merck |
| PSI-7851 | Polymerase inhibitor | Pharmasset |
| ANA598 | Polymerase inhibitor | Anadys Pharmaceuticals |
| BI-207127 | Polymerase inhibitor | Boehringer-Ingelheim |
| GS-9190 | Polymerase inhibitor | Gilead |
| GS-9669 | Polymerase inhibitor | Gilead |
| VCH-759 | Polymerase Inhibitor | Vertex |
| VX-135 | Polymerase Inhibitor | Vertex |
| VX-222 | Polymerase Inhibitor | Vertex |
| TMC647055 | Polymerase Inhibitor | Janssen |
| MBX-700 | Polymerase Inhibitor | Microbiotix/Merck |
| IDX21437 | Polymerase Inhibitor | Idenix |
| IDX20963 | Polymerase Inhibitor | Idenix |
| ACH-3422 | Polymerase Inhibitor | Achillion |
| Clemizole | NS4B inhibitor | Eiger Biopharmaceuticals |
| A-832 | NS5A inhibitor | ArrowTherapeutics |
| BMS-790052 | NS5A inhibitor | Bristol-Myers-Squibb |
| BMS-824393 | NS5A inhibitor | Bristol-Myers-Squibb |
| GS-5885 | NS5A inhibitor | Gilead |
| GS-5816 | NS5A inhibitor | Gilead |
| PPI-688 | NS5A inhibitor | Presidio |
| ACH-3102 | NS5A inhibitor | Achillion |
| IDX-719 | NS5A inhibitor | Idenix |
| ITX5061 | Entry inhibitor | iTherx |
| GS-9450 | Caspase inhibitor | Gilead |
| ANA773 | TLR agonist immunomodulator | Anadys |
| CYT107 | immunomodulator | Cytheris |
| SPC3649 (LNA-ANTIMIR ™-122) | microRNA | Santaris Pharma |
| Debio 025 | Cyclophilin inhibitor | Novartis/Debiopharm |
| SCY-635 | Cyclophilin inhibitor | Scynexis |

Combination Therapy for the Treatment of Proliferative Conditions

In another embodiment, the compounds, when used as an antiproliferative, can be administered in combination with another compound that increases the effectiveness of the therapy, including but not limited to an antifolate, a 5-fluoropyrimidine (including 5-fluorouracil), a cytidine analogue such as β-L-1,3-dioxolanyl cytidine or β-L-1,3-dioxolanyl 5-fluorocytidine, antimetabolites (including purine antimetabolites, cytarabine, fudarabine, floxuridine, 6-mercaptopurine, methotrexate, and 6-thioguanine), hydroxyurea, mitotic inhibitors (including CPT-11, Etoposide (VP-21), taxol, and vinca alkaloids such as vincristine and vinblastine, an alkylating agent (including but not limited to busulfan, chlorambucil, cyclophosphamide, ifofamide, mechlorethamine, melphalan, and thiotepa), nonclassical alkylating agents, platinum containing compounds, bleomycin, an anti-tumor antibiotic, an anthracycline such as doxorubicin and dannomycin, an anthracenedione, topoisomerase II inhibitors, hormonal agents (including but not limited to corticosteroids (dexamethasone, prednisone, and methylprednisone), androgens such as fluoxymesterone and methyltestosterone, estrogens such as diethylstilbesterol, antiestrogens such as tamoxifen, LHRH analogues such as leuprolide, antiandrogens such as flutamide, aminoglutethimide, megestrol acetate, and medroxyprogesterone), asparaginase, carmustine, lomustine, hexamethyl-melamine, dacarbazine, mitotane, streptozocin, cisplatin, carboplatin, levamasole, and leucovorin. The compounds of the present invention can also be used in combination with enzyme therapy agents and immune system modulators such as an interferon, interleukin, tumor necrosis factor, macrophage colony-stimulating factor and colony stimulating factor.

Although the invention has been described with respect to various preferred embodiments, it is not intended to be limited thereto, but rather those skilled in the art will recognize that variations and modifications may be made therein which are within the spirit of the invention and the scope of the appended claims.

ABBREVIATIONS

Abbreviations which may be used in the descriptions of the scheme and the examples that follow are: Ac for acetyl; AcOH for acetic acid; AIBN for azobisisobutyronitrile; BINAP for 2,2'-bis(diphenylphosphino)-1,1'-binaphthyl; Boc$_2$O for di-tert-butyl-dicarbonate; Boc for t-butoxycarbonyl; Bpoc for 1-methyl-1-(4-biphenylyl)ethyl carbonyl; Bz for benzoyl; Bn for benzyl; BocNHOH for tert-butyl N-hydroxycarbamate; t-BuOK for potassium tert-butoxide; Bu$_3$SnH for tributyltin hydride; BOP for (benzotriazol-1-yloxy)tris(dimethylamino)phosphonium Hexafluorophosphate; Brine for sodium chloride solution in water; BSA for N,O-bis(trimethylsilyl)acetamide; CDI for carbonyldiimidazole; CH$_2$Cl$_2$ for dichloromethane; CH$_3$ for methyl; CH$_3$CN for acetonitrile; Cs$_2$CO$_3$ for cesium carbonate; CuCl for copper (I) chloride; CuI for copper (I) iodide; dba for dibenzylidene acetone; dppb for diphenylphos-phinobutane; DBU for 1,8-diazabicyclo[5.4.0]-undec-7-ene; DCC for N,N'-dicyclohexyl-carbodiimide; DEAD for diethylazodicarboxylate; DIAD for diisopropyl azodicarboxylate; DIPEA or (i-Pr)$_2$EtN for N,N,-diisopropylethyl amine; Dess-Martin periodinane for 1,1,1-tris(acetyloxy)-1,1-dihydro-1,2-benziodoxol-3-(1H)-one; DMAP for 4-dimethyl-amino-pyridine; DME for 1,2-dimethoxyethane; DMF for N,N-dimethylformamide; DMSO for dimethyl sulfoxide; DMT for di(p-methoxyphenyl)-phenylmethyl or dimethoxytrityl; DPPA for diphenylphosphoryl azide; EDC for N-(3-dimethylaminopropyl)-N'-ethylcarbodiimide; EDC HCl for N-(3-dimethylaminopropyl)-N'-ethylcarbodiimide hydrochloride; EtOAc for ethyl acetate; EtOH for ethanol; Et$_2$O for diethyl ether; HATU for O-(7-azabenzotriazol-1-yl)-N,N,N',N',-tetramethyluronium Hexafluoro-phosphate; HCl for hydrogen chloride; HOBT for 1-hydroxybenzotriazole; K$_2$CO$_3$ for potassium carbonate; n-BuLi for n-butyl lithium; i-BuLi for i-butyl lithium; t-BuLi for t-butyl lithium; PhLi for phenyl lithium; LDA for lithium diisopropylamide; LiTMP for lithium 2,2,6,6-tetramethyl-piperidinate; MeOH for methanol; Mg for magnesium; MOM for methoxymethyl; Ms for mesyl or —SO$_2$—CH$_3$; Ms$_2$O for methanesulfonic anhydride or mesyl-anhydride; MTBE for t-butyl methyl ether; NaN(TMS)$_2$ for sodium bis(trimethylsilyl)amide; NaCl for sodium chloride; NaH for sodium hydride; NaHCO$_3$ for sodium bicarbonate or sodium hydrogen carbonate; Na$_2$CO$_3$ sodium carbonate; NaOH for sodium hydroxide; Na$_2$SO$_4$ for sodium sulfate; NaHSO$_3$ for sodium bisulfite or sodium hydrogen sulfite; Na$_2$S$_2$O$_3$ for sodium thiosulfate; NH$_2$NH$_2$ for hydrazine; NH$_4$HCO$_3$ for ammonium bicarbonate; NH$_4$Cl for ammonium chloride; NMO for N-methylmorpholine N-oxide; NaIO$_4$ for sodium periodate; Ni for nickel; OH for hydroxyl; OsO$_4$ for osmium tetroxide; PTSA for p-toluenesulfonic acid; PPTS for pyridiniump-toluenesulfonate; TBAF for tetrabutylammonium fluoride; TEA or Et$_3$N for triethylamine; TES for triethylsilyl; TESCl for triethylsilyl chloride; TESOTf for triethylsilyl trifluoromethanesulfonate; TFA for trifluoroacetic acid; THF for tetrahydrofuran; TMEDA for N,N,N',N'-tetramethylethylene-diamine; TPP or PPh$_3$ for triphenyl-phosphine; Troc for 2,2,2-trichloroethyl carbonyl; Ts for tosyl or —SO$_2$—C$_6$H$_4$CH$_3$; Ts$_2$O for tolylsulfonic anhydride or tosyl-anhydride; TsOH for p-tolylsulfonic acid; Pd for palladium; Ph for phenyl; POPd for dihydrogen dichlorobis(di-tert-butylphosphinito-κP)palladate(II); Pd$_2$(dba)$_3$ for tris(dibenzylideneacetone)dipalladium (O); Pd(PPh$_3$)$_4$ for tetrakis(triphenylphosphine)-palladium (O); PdCl$_2$(PPh$_3$)$_2$ for trans-dichloro-bis-(triphenylphosphine)palladium (II); Pt for platinum; Rh for rhodium; Ru for ruthenium; TBS for tert-butyl dimethylsilyl; TMS for trimethylsilyl; or TMSCl for trimethylsilyl chloride.

Synthetic Methods

The compounds and processes of the present invention will be better understood in connection with the following synthetic schemes that illustrate the methods by which the compounds of the invention may be prepared. These schemes are of illustrative purpose, and are not meant to limit the scope of the invention. Equivalent, similar, or suitable solvents, reagents or reaction conditions may be substituted for those particular solvents, reagents, or reaction conditions described herein without departing from the general scope of the method of synthesis.

The syntheses of various nucleoside analogs have been well documented in the literature, the following reviews are incorporated hereinwith by references: D. M. Huryn and M. Okabe, Chem. Rev. 1992, 92, 1745; K. W. Pankiewicz, Carbohydrate Research, 2000, 327, 87-105; G. Gumina et al, Antiviral Nucleosides: Chiral Synthesis and Chemotherapy, C. K. Chu (Ed.), Elsevier, 2003, pages 1-76 and 77-189; nucleoside analogs used as antimetabolites have been summarized: M. M. Mader and J. R. Henry, Comprehensive Medicinal Chemistry II, Elsevier, 2007, Vol. 7, pages 55-79; nucleoside analogs used as antiviral agents have been summarized: Comprehensive Medicinal Chemistry II, Elsevier, 2007, Vol. 7, pages 295-327 by E. Littler and X-X Zhou; and pages 338-343 by T. A. Lyle; and pages 398-400 by U. Schmitz et al. The synthesis of each of these individual analog can be found in the literatures cited therein. Nonlimiting examples of process are also incorporated hereinwith by reference: Clark et al., J. Med. Chem. 2005, 48, 5504; Clark et al., Bioorg. Med. Chem. Lett. 2006, 16, 1712; Clark et al., J. Carbohydr. Chem. 2006, 25, 461; Seela et al., Org. Biomol. Chem. 2008, 6, 596; Pan et al., J. Org. Chem. 1999, 94, 4; Shi et al., Bioorg. Med. Chem. 2005, 13, 1641; He et al., J. Org. Chem. 2003, 68, 5519; Gudmundsson et al., J. Med. Chem. 2000, 43, 2473; Jean-Baptiste et al., Synlett 2008, 817; Wilson et al., Synthesis 1995, 1465; Lin et al., J. Med. Chem. 1991, 34, 2607; Matsuda et al., J. Med. Chem. 1991, 34, 812; Robins et al., J. Med. Chem. 1992, 35, 2283; Serafinowski et al., Tetrahedron 1996, 52, 7929; Serafinowski et al., Tetrahedron 2000, 56, 333; Houlton et al., Tetrahedron 1993, 49, 8087; Serafinowski et al., Synthesis 1997, 225; McCarthy et al., Tetrahedron 1996, 52, 45; Schmit, Synlett 1994, 241; Hirota et al., ChemComm 1999, 1827; Babu et al., Org. Biomol. Chem. 2003, 1, 3514; Samano et al., J. Am. Chem. Soc. 1992, 114, 4007; Beard et al., Carbohydrate Res. 1990, 87; Wigerinck et al., J. Med. Chem. 1991, 34, 2383; Ye et al., J. Org. Chem. 2005, 70, 7902; Eldrup et al., J. Med. Chem. 2004, 47, 2283 and 5284; Tang et al., J. Org. Chem. 1999, 64, 747; Jeannot et al., Org. Biomol. Chem. 2003, 1, 2096; Li et al., Org. Lett. 2001, 3, 1025; Marcotte et al., Synthesis 2001, 929; Dai et al., Org. Lett. 2001, 3, 807; Yoshimura et al., Bioorg. Med. Chem. Lett. 1994, 4, 721; Ohtawa et al., J. Med. Chem. 2007, 50, 2007; McGee et al., J. Org. Chem. 1996, 61, 781; Ogamino et al., J. Org. Chem. 2005, 70, 1684; Ichikawa et al., Org. Biomol. Chem. 2006, 4, 1284; Pan et al., J. Org. Chem. 1999, 64, 4; Huang et al., J. Med. Chem. 1991, 34, 1640; Kodama et al., Tetrahedron 2006, 62, 10011; He et al., J. Org. Chem. 2003, 68, 5519; Kumamoto et al., J. Med. Chem. 2006, 49, 7861; and Haraguchi et al., Org. Lett. 2004, 6, 2645.

The synthesis of 4'-substituted nucleoside analogs have also been well documented in the literature, see references cited in a review article by Hayakawa et al., Antiviral Chem. Chemother. 2004, 15, 169 and nonlimiting examples of process: Cook et al., J. Am. Chem. Soc. 1979, 101, 1554; Haraguchi et al., J. Med. Chem. 2008, 51, 1885; Kubota et al., J. Org. Chem. 2006, 71, 1099; Haraguchi et al., Org. Lett. 2003, 5, 1399; Haraguchi et al., J. Org. Chem. 2006, 71, 4433; Haraguchi et al., J. Am. Chem. Soc. 1975, 97, 4433; Maag et al., J. Med. Chem. 1992, 35, 1440; Marx et al., Helv. Chim. Acta 1996, 79, 1980; Youssefyeh et al., J. Org. Chem. 1979, 44, 1301; Jones et al., J. Org. Chem. 1979, 44, 1309; Perrone et al., J. Med. Chem. 2007, 50, 5463; Smith et al., Bioorg. Med. Chem. Lett. 2007, 17, 2570; Nomura et al., J. Med. Chem. 1999, 42, 2901; Wang et al., J. Org. Chem.

2009, 74, 6819; Reddy et al., *J. Org. Chem.* 2011, 76, 3782; Moon et al., *Tetrahedron* 2010, 66, 6707; and Maag et al., *J. Med. Chem.* 1994, 37, 431.

One of the general procedures to synthesize the fused 2',3'-cyclopropanated nucleosides (II) or their derivatives (II-1) of the present invention is shown in Scheme 1 (wherein LG is a leaving group and PG is a hydroxy protecting group), in which a suitable substituted, fused 2,3-cyclopropanated furanosyl derivative (1-1) is glycosylated with a suitable substituted nucleobase, optionally in the presence of a Lewis acid or a base and optionally at elevated temperature. A suitable substituted, fused 2,3-cyclopropanated furanosyl derivative includes but not limited to its 1-acetate, 1-benzoate, 1-bromide, and 1-chloride. A suitable substituted nucleobase may be activated with one or more N-silylations, which are known to those in the art. A suitable Lewis Acid includes but is not limited to tin(IV) chloride, trimethylsilyl triflate, boron trifluoride etherate and ethylaluminium dichloride. A suitable base includes but not limit to cesium carbonate, potassium tert-butoxide, DBU and NaH. The glycosylation reaction may have certain α- and β-face selectivity to produce a mixture of α- and β-glycosides. A compound of Formular (II-1) may be converted to nucleoside (II) through deprotection, functional group manipulation or a combination of both.

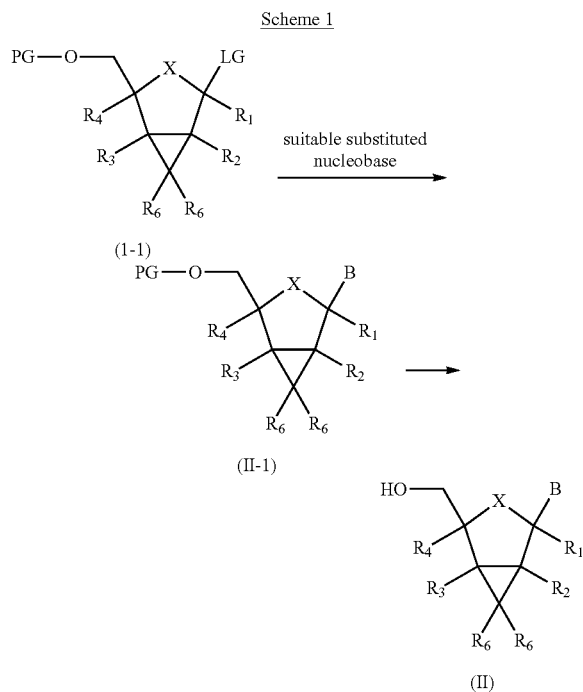

Another general procedure to synthesize the fused 2',3'-cyclopropanated nucleosides (II) or their derivatives (II-1) of the present invention is shown in Scheme 2, in which a suitable substituted nucleoside derivative (2-1) containing a 2',3'-olefinic double bond is cyclopropanated using the method known to those in the art. The cyclopropanation condition may include but not limited to diiodomethane-diethylzin optionally in the presence of trifluoroacetic acid; chloroiodomethane-samarium; diazomethane optionally in the presence of a palladium or copper catalyst; sodium chlorodifluoroacetate under heating; chloroform-NaOH in the presence of a phase-transfer catalyst; and ethyl diazoacetate under heating or light or in the presence of a metal catalyst.

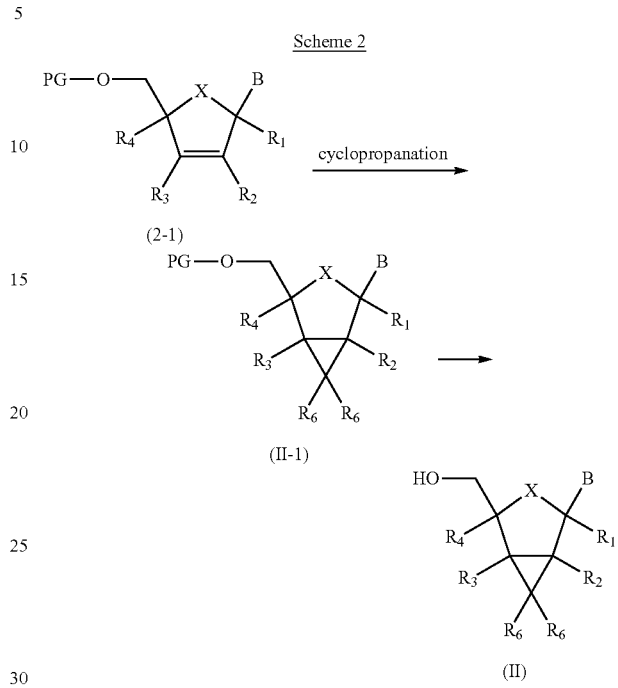

An illustrative procedure to synthesize glycosylation donor intermediate (1-1 in Scheme 1) is shown in Scheme 1a. Commercially available pyruvate 1a-1 is converted to 2-acetoxyacrylate 1a-2, which is then treated with ethyl dibromofluoroacetate in the presence of zinc powder to produce a mixture of tetra-substituted cyclopropane syn- and anti-dicarboxylate 1a-3. The α-fluorocarboxylate in 1a-3 is selectively reduced to the desired primary alcohol 1a-4 after column chromatography, by a two-step consecutive reduction with lithium triethylborohydride and lithium (tri-tert-butoxy)aluminum hydride. The conversion of alcohol 1a-4 to intermediate 1a-5 can be realized by a three-step procedure: 1) hydroxy protection as tert-butyl diphenylsilyl (TBDPS) ether; 2) subsequent treatment with N,O-dimethylhydroxylamine converts the remaining carboxylate to Weinreb amide and releases the cyclopropyl alcohol; and 3) triethysilyl ether formation. Reduction of the Weinreb amide in 1a-5 affords an aldehyde intermediate, which is then reacted with vinylmagnesium bromide to afford allylic alcohol 1a-6. The double bond is cleaved by ozone, followed by treatment with sodium borohydride to afford a vicinal diol 1a-7. Conversion from 1a-7 to 1a-8 can be achieved in three steps: 1) cleavage of the triethylsilyl ether in the presence of pyridium p-toluenesulfonate (PPTS) to afford a triol; 2) protection of the terminal diol as acetonide with 2,2-dimethoxypropane in the presence of PPTS; and 3) protection of the cyclopropyl alcohol as acetate by acetic anhydride. The TBDPS ether in intermediate 1a-8 is deprotected with hydrogen fluoride-pyridine to afford a primary alcohol, which is then oxidized to aldehyde 1a-9 by Dess-Martin Periodinane. Treatment of the aldehyde 1a-9 with aqueous acetic acid affords the requisite ribosyl hemiacetal, which is then converted to acetate 1a-10. The anomeric acetate can be converted to bromide 1a-11 by hydrogen bromide in acetic acid. Both acetate 1a-10 and bromide 1a-11 can serve as universal donors in glycosylation reaction.

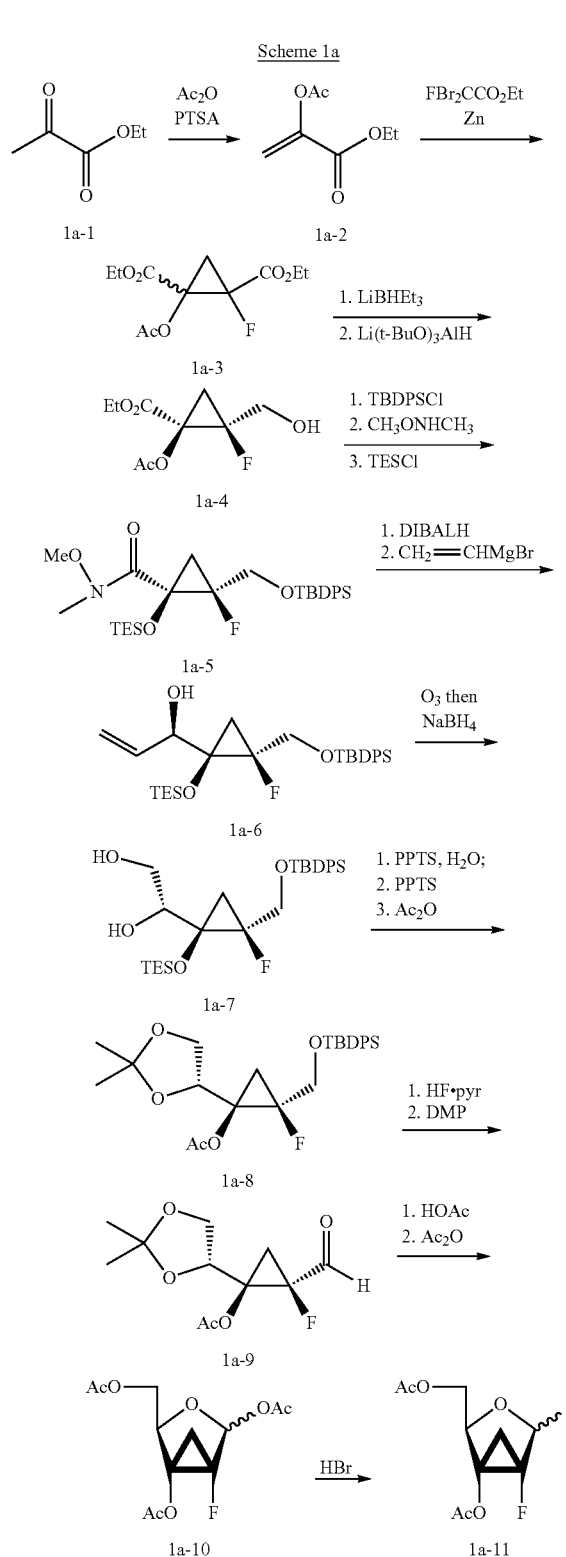

When switching some reaction sequence and using similar chemistry described above and in Scheme 1a, the alcohol intermediate 1a-4 may be converted to glycosylation donors 1b-1 and 1b-2, as shown in Scheme 1b.

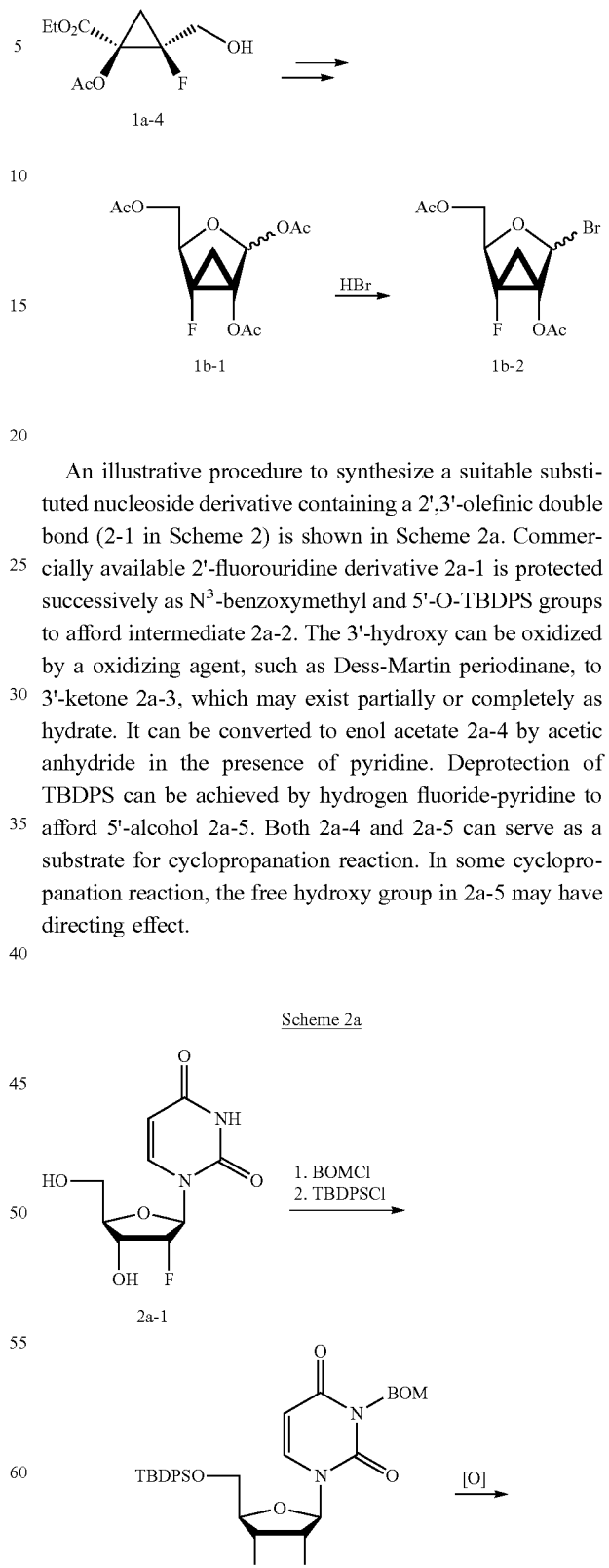

An illustrative procedure to synthesize a suitable substituted nucleoside derivative containing a 2',3'-olefinic double bond (2-1 in Scheme 2) is shown in Scheme 2a. Commercially available 2'-fluorouridine derivative 2a-1 is protected successively as $N^3$-benzoxymethyl and 5'-O-TBDPS groups to afford intermediate 2a-2. The 3'-hydroxy can be oxidized by a oxidizing agent, such as Dess-Martin periodinane, to 3'-ketone 2a-3, which may exist partially or completely as hydrate. It can be converted to enol acetate 2a-4 by acetic anhydride in the presence of pyridine. Deprotection of TBDPS can be achieved by hydrogen fluoride-pyridine to afford 5'-alcohol 2a-5. Both 2a-4 and 2a-5 can serve as a substrate for cyclopropanation reaction. In some cyclopropanation reaction, the free hydroxy group in 2a-5 may have directing effect.

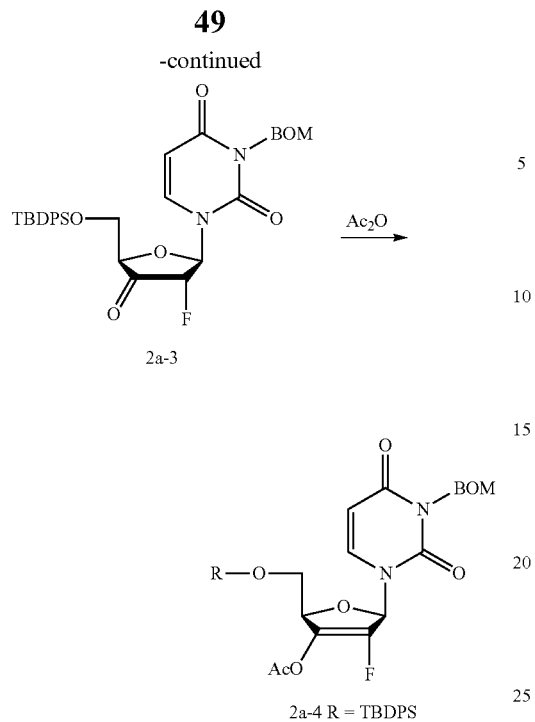

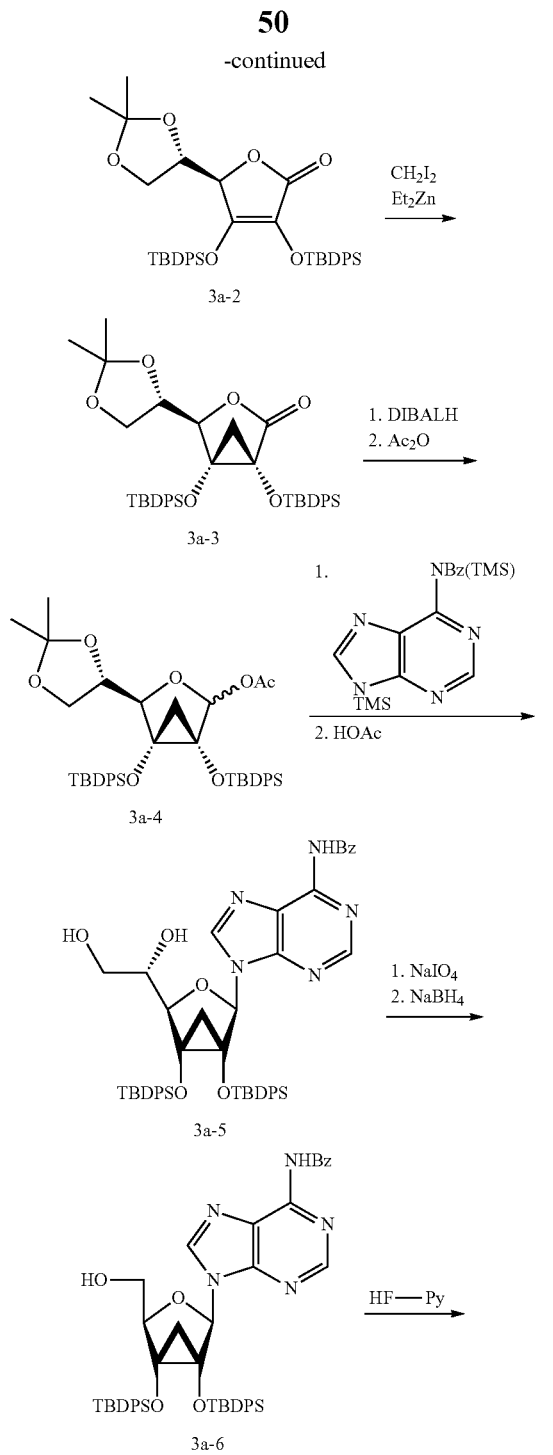

Additionally as shown in Scheme 3a, the synthesis of the fused 2',3'-cyclopropanated nucleosides (II) or their derivatives (II-1) of the present invention can also be achieved by sequential cyclopropanation on a suitable olefinic precursor and glycosylation of a suitable ribosyl derivative with a masked 5'-moiety, though additional functional group manipulation steps may be necessary. L-ascorbic acid 3a-1 is protected to afford derivative 3a-2 by known procedure (H. Kato et al., *Chem. Pharm. Bull.* 2007, 55, 1700). Cyclopropanation of 3a-2 may be achieved with a suitable reaction condition, which are known to those in the art, includes but not limited to diiodomethane-diethylzinc, a sulfur ylide such as $Me_2S^+CH_2^-$ or $Me_2S(O)^+CH_2^-$, to afford compound 3a-3. The lactone can be reduced by DIBAL-H to a hemiacetal, which is acetylated by acetic anhydride to 3a-4. Glycosylation between 3a-4 and 2,4-bis ((trimethylsilyl)oxy)purine may be catalyzed by trimethylsilyl triflate to afford nucleoside derivative 3a-5 after deprotection with acetic acid. The vicinal diol is treated with sodium periodate, followed by sodium borohydride reduction, to afford 5'-alcohol 3a-6. Optionally, TBDPS deprotections by hydrogen fluoride-pyridine afford compound 3a-7.

Scheme 3a

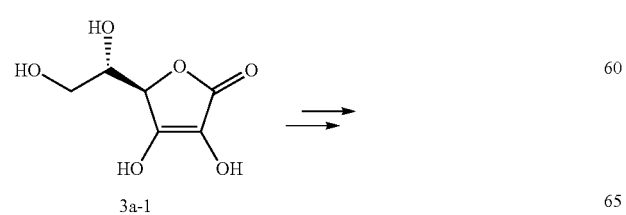

The synthesis of nucleoside 5'-monophosphate prodrugs have also been well documented in the literature, see references cited in accounts by Cahard et al., *Mini-Reviews Med. Chem.* 2004, 4, 371; Meier et al., *Mini-Reviews Med. Chem.* 2004, 4, 383; Peyrottes et al., *Mini-Reviews Med. Chem.* 2004, 4, 395; Drontle et al., *Mini-Reviews Med. Chem.* 2004, 4, 409; and nonlimiting examples of recent process: Gisch et al., *J. Med. Chem.* 2007, 50, 1658; Boyer et al., *J. Med. Chem.* 2006, 49, 7711; Khamnei et al., *J. Med. Chem.* 1996, 39, 4109; Li et al., *Synlett* 2004, 2600; Perrone et al., *J. Med. Chem.* 2007, 50, 5463; Gisch et al., *J. Med. Chem.* 2007, 50, 1658 and 1840; Hecker et al., *J. Med. Chem.* 2007, 50, 3891; Prakash et al., *J. Med. Chem.* 2005, 48, 1199; Sofia et al., *J. Med. Chem.* 2010, 53, 7202; Ross et al., *J. Org. Chem.* 2011, 76, 8311; and Gunic et al., *Bioorg. Med. Chem. Lett.* 2007, 17, 2452 (for 3',5'-cyclic monophosphate prodrug).

The synthesis of nucleoside phosphonates and/or their prodrugs have also been well documented in the literature, see references cited in accounts by Hecker et al., *J. Med. Chem.* 2008, 51, 2328; Krise et al., *Adv. Drug Deliv. Rev.* 1996, 19, 287; Berkowitz et al., *J. Fluorine Chem.* 2001, 112, 13; Romanenko et al., *Chem. Rev.* 2006, 106, 3868; De Clercq, *Antiviral Res.* 2007, 75, 1; De Clercq et al., *Nat. Rev.-Drug Disc.* 2005, 4, 928; and nonlimiting examples of recent process: Mackman et al., *Bioorg. Med. Chem.* 2007, 15, 5519; Dang et al, *Bioorg. Med. Chem. Lett.* 2007, 17, 3412; Meier et al., *J. Med. Chem.* 2005, 48, 8079; Wu et al., *Nucleosides Nucleotides Nuclic Acids* 2005, 24, 1543; Choi et al., *J. Med. Chem.* 2004, 47, 2864; Sekiya et al., *J. Med. Chem.* 2002, 45, 3138; Louie et al., *Nucleosides Nucleotides Nuclic Acids* 2001, 20, 1099; Serafinowska et al., *J. Med. Chem.* 1995, 38, 1372; Koh et al., *J. Med. Chem.* 2005, 48, 2867; Mackman et al., *Bioorg. Med. Chem.* 2007, 15, 5519; Wang et al., *Nucleosides Nucleotides Nuclic Acids* 2004, 23, 317; Dyatkina et al., *Tetrahedron* 1995, 51, 761; Reddy et al., *J. Med. Chem.* 2008, 51, 666; Krecmerova et al., *J. Med. Chem.* 2007, 50, 5765.

It will be appreciated that, with appropriate manipulation and protection of any chemical functionality, synthesis of compounds of Formula (I) is accomplished by methods analogous to those above and to those described in the Experimental section. Suitable protecting groups can be found, but are not restricted to those found in T W Greene and P G M Wuts "Protective Groups in Organic Synthesis", 3rd Ed (1999), J Wiley and Sons.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

EXAMPLES

The compounds and processes of the present invention will be better understood in connection with the following examples, which are intended as an illustration only and not limiting of the scope of the invention.

Intermediate 1a-2

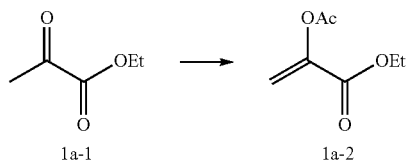

Step 1.

A solution of ethyl pyruvate (40.642 g, 0.3500 mol) and PTSA.H$_2$O (1.332 g, 7.000 mmol) in acetic anhydride (66.17 mL) was stirred in a sealed tube at 140° C. for 24 hours. The mixture was allowed to cool down and purified by vacuum distillation to afford compound 1a-2 as a colorless oil (29.758 g, 54%). $^1$H NMR (500 MHz, CDCl$_3$) δ 6.04 (s, 1H), 5.46 (s, 1H), 4.25 (q, J=7.1 Hz, 2H), 2.47 (s, 3H), 1.31 (t, J=7.1 Hz, 3H).

Intermediate 1a-3

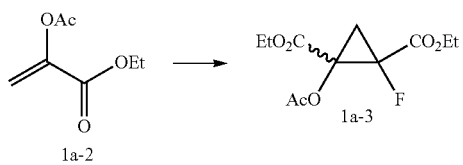 [SMILES: C=C(OC(C)=O)C(=O)OCC ; CCOC(=O)C1(F)CC1(OC(C)=O)C(=O)OCC]

Step 2.

LiCl (1.272 g, 30.00 mmol) and Zn (1.962 g, 30.00 mmol) was dried under vacuum at 170° C. for 30 min before being allowed to cool down. THF (50 mL) was added, followed by DMSO (0.08 mL) and TMSCl (0.16 mL). The mixture was vigorously stirred at 50° C. for 15 min. 10 drops of a solution of FBr$_2$CCO$_2$Et (5.278 g, 20.00 mmol) in THF (10 mL) were added. The mixture was cooled to 0° C. A solution of compound 1a-2 (1.582 g, 10.00 mmol) in THF (10 mL) was added at 0° C. The rest of the solution of FBr$_2$CCO$_2$Et was added at 0° C. dropwise over 30 min. After addition, the mixture was stirred at 0° C. for 30 min before being poured into a mixture of EtOAc (250 mL) and 0.5N HCl aq. (150 mL). The organic phase was washed with brine, dried (Na$_2$SO$_4$), filtered and concentrated. The residue was purified by flash column chromatography (silica, EtOAc-hexanes) to afford compound 1a-3 as a yellow oil (1.394 g, 53%), which is a mixture of cis/trans isomers. 1H NMR (500 MHz, CDCl$_3$) δ 4.32-4.19 (m, 8H), 2.64 (dd, J=8.8, 19.4 Hz, 1H), 2.49 (dd, J=9.4, 15.8 Hz, 1H), 2.21-2.18 (m, 4H), 2.10 (s, 3H), 1.85 (dd, J=9.4, 21.3 Hz, 1H), 1.35-1.24 (m, 12H).

Intermediate 1a-4

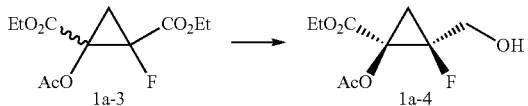

Step 3.

To a solution of compound 1a-3 (3.400 g, 12.97 mmol) in THF (60 mL) cooled at −78° C. was added super-hydride (1.0M in THF, 13.61 mL, 13.61 mmol) dropwise. The mixture was stirred at −78° C. for 30 min. More super-hydride (1.0M in THF, 13.61 mL, 13.61 mmol) was added dropwise. After another 30 min at −78° C., 3N HCl solution (9.96 mL) was added at −78° C. to quench the reaction. The mixture was allowed to warm up to rt. THF was evaporated. The residue was diluted with EtOAc and brine. The organic phase was washed with saturated NaHCO$_3$ solution, brine, dried (Na$_2$SO$_4$), filtered and concentrated. The residue was dried under vacuum to afford the intermediate aldehyde as a yellow oil (3.040 g), which was used directly for next step.

1H NMR (500 MHz, CDCl₃) δ 9.76 (d, J=3.5 Hz, 1H), 9.63 (d, J=12.7 Hz, 1H), 4.29-4.24 (m, 4H), 2.67 (dd, J=8.8, 19.2 Hz, 1H), 2.56 (dd, J=9.4, 15.1 Hz, 1H), 2.18-2.05 (m, 8H), 1.43-1.27 (m, 6H).

Step 4.

To a solution of the compound from step 3(3.040 g, 12.97 mmol at most) in THF (60 mL) cooled at 0° C. was added Li(t-BuO)₃AlH (1.0M in THF, 14.26 mL, 14.26 mmol) dropwise. The mixture was stirred at 0° C. for 1 hour. 3N HCl solution (6.00 ml) was added at 0° C. to quench the reaction. The mixture was allowed to warm up to rt. THF was evaporated. More 3N HCl solution (20 mL) was added until pH ~1 and no precipitate remained. The mixture was diluted with EtOAc. The organic phase was washed with saturated NaHCO₃ solution, brine, dried (Na₂SO₄), filtered and concentrated. The residue was purified by flash column chromatography (silica, EtOAc-hexanes) to afford the compound 1a-4 as a yellow oil (0.625 g, 22% over 2 steps). ¹H NMR (500 MHz, CDCl₃) δ 4.32 (t, J=14.4 Hz, 1H), 4.24 (q, J=7.1 Hz, 2H), 4.08 (dd, J=13.2, 30.1 Hz, 1H), 2.17 (s, 3H), 1.96 (dd, J=8.9, 16.4 Hz, 1H), 1.76 (dd, J=8.9, 22.3 Hz, 1H), 1.28 (t, J=7.1 Hz, 3H).

Intermediate 1a-5

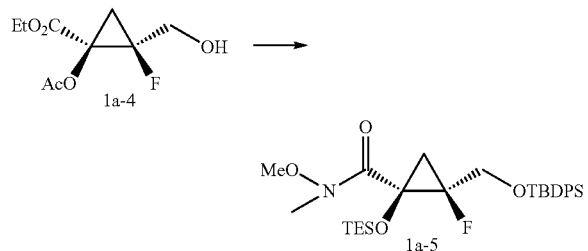

Step 5.

To a solution of compound 1a-4 (6.200 g, 28.16 mmol) in dichloromethane (150 mL) at rt was added imidazole (3.834 g, 56.32 mmol), followed by TBDPSCl (9.52 mL, 36.60 mmol). The resulting yellow suspension was stirred at rt for 2 hours. Isopropanol (1.2 mL) was added at rt to quench the reaction. After 30 min, the mixture was diluted with 50% brine and EtOAc. The organic phase was washed with brine, dried (Na₂SO₄), filtered and concentrated. The residue was purified by flash column chromatography (silica, EtOAc-hexanes) to afford the desired compound as a colorless oil (11.00 g, 85%). ¹H NMR (500 MHz, CDCl₃) δ 7.72-7.65 (m, 4H), 7.43-7.39 (m, 6H), 4.25 (dd, J=12.8, 22.2 Hz, 1H), 4.17-4.13 (m, 2H), 4.07 (dd, J=12.8, 37.0 Hz, 1H), 2.13 (s, 3H), 1.94 (dd, J=18.8, 25.7 Hz, 1H), 1.57 (dd, J=18.8, 21.7 Hz, 1H), 1.20 (t, J=7.2 Hz, 3H), 1.06 (s, 9H).

Step 6.

A mixture of the compound from step 5 (11.00 g, 23.99 mmol) and N,O-dimethylhydroxyamine hydrochloride (7.019 g, 71.96 mmol) in THF (350 mL) was cooled to −20° C. i-PrMgCl (2.0M in THF, 71.96 mL, 0.1439 mol) was added dropwise at −20° C. over 30 min. After the addition, the mixture was stirred at −20° C. for 30 min. More i-PrMgCl (2.0M in THF, 5.99 mL, 12.00 mmol) was added dropwise at −20° C. After 30 min at −20° C., excess saturated NH₄Cl solution was added to quench the reaction. The mixture was allowed to warm up to rt and diluted with brine and EtOAc. The aqueous layer was extracted with EtOAc. The combined organic phases were washed with brine, dried (Na₂SO₄), filtered and concentrated. The residue was purified by flash column chromatography (silica, EtOAc-hexanes) to afford the desired compound as a colorless oil (6.200 g, 60%). ¹H NMR (500 MHz, CDCl₃) δ 7.68-7.63 (m, 4H), 7.42-7.37 (m, 6H), 4.06 (dd, J=12.9, 17.1 Hz, 1H), 3.82 (s, 3H), 3.74 (dd, J=12.7, 29.9 Hz, 1H), 3.26 (s, 3H), 1.77 (dd, J=8.3, 14.2 Hz, 1H), 1.63 (br s, 1H), 1.36 (dd, J=8.3, 23.0 Hz, 1H), 1.04 (s, 9H).

Step 7.

To a solution of the compound from step 6 (0.140 g, 0.324 mmol) and imidazole (66.3 mg, 0.973 mmol) in DMF (4 mL) at rt was added TESCl (0.071 mL, 0.422 mmol) dropwise. The resulting clear solution was stirred at rt for 1 hour. EtOH (0.05 mL) was added at rt to quench the reaction. After 10 min, the mixture was diluted with MTBE and H₂O. The organic phase was washed with brine (*2), dried (Na₂SO₄), filtered and concentrated. The residue was purified by flash column chromatography (silica, MTBE-hexanes) to afford compound 1a-5 as a colorless oil (0.175 g, 99%). ¹H NMR (500 MHz, CDCl₃) δ 7.68-7.63 (m, 4H), 7.43-7.36 (m, 6H), 3.92 (br s, 1H), 3.69 (s, 3H), 3.42 (br s, 4H), 1.66 (dd, J=8.4, 14.3 Hz, 1H), 1.23 (dd, J=8.4, 13.2 Hz, 1H), 1.05 (s, 9H), 0.97 (t, J=7.9 Hz, 9H), 0.68 (q, J=7.9 Hz, 6H).

Intermediate 1a-6

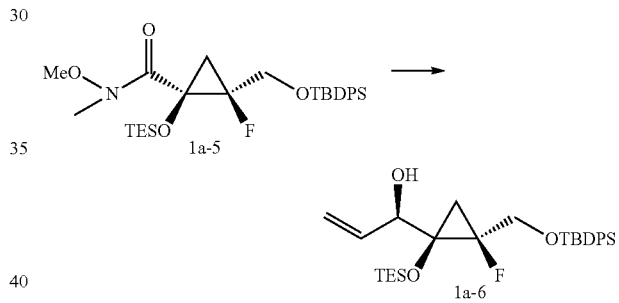

Step 8.

To a solution of compound 1a-4 (50.0 mg, 0.0916 mmol) in dichloromethane (2 mL) cooled at −78° C. was added DIBAL-H (1.0M in hexanes, 0.11 mL, 0.110 mmol) dropwise. The resulting clear solution was stirred at −78° C. for 1 hour. More DIBAL-H (1.0M in hexanes, 0.03 mL, 0.030 mmol) was added. After 30 min, the mixture was poured into a vigorously stirred potassium sodium tartrate solution. The mixture was stirred at rt for 1 h. The layers were separated. The aqueous phase was extracted with dichloromethane. The combined organic phases were dried (Na₂SO₄), filtered and concentrated. The residue was purified by flash column chromatography (silica, MTBE-hexanes) to afford the desired aldehyde as a colorless oil (36.6 mg, 82%). ¹H NMR (500 MHz, CDCl₃) δ 9.66 (s, 1H), 7.84-7.64 (m, 4H), 7.45-7.38 (m, 6H), 4.16 (dd, J=12.9, 17.9 Hz, 1H), 3.75 (dd, J=12.9, 20.9 Hz, 1H), 1.68 (dd, J=8.0, 15.0 Hz, 1H), 1.53 (dd, J=8.0, 21.5 Hz, 1H), 1.04 (s, 9H), 0.99 (t, J=7.9 Hz, 9H), 0.80-0.70 (m, 6H).

Step 9.

To a solution of the compound from step 8 (0.820 g, 1.685 mmol) in THF (30 mL) cooled at −78° C. was added vinylmagnesium bromide (1.0M in THF, 1.68 mL, 1.68 mmol) dropwise. The mixture was stirred at −78° C. for 20 min. More vinylmagnesium bromide (1.0M in THF, 0.25 mL, 0.25 mmol) was added. After 20 min at −78° C., More vinylmagnesium bromide (1.0M in THF, 0.17 mL, 0.17 mmol) was added. After 15 min at −78° C., the reaction was quenched with excess saturated NH$_4$Cl solution. The mixture was allowed to warm up to rt and diluted with MTBE. The organic phase was washed with brine, dried (Na$_2$SO$_4$), filtered and concentrated. The residue was purified by flash column chromatography (silica, MTBE-hexanes) to afford compound 1a-6 as a colorless oil (0.310 g, 36%), along with the undesired diastereomer (0.322 g, 37%). $^1$H NMR (500 MHz, CDCl$_3$) δ 7.73-7.66 (m, 4H), 7.45-7.38 (m, 6H), 6.03-5.97 (m, 1H), 5.36 (d, J=17.3 Hz, 1H), 5.18 (d, J=10.6 Hz, 1H), 4.20 (dd, J=13.0, 18.1 Hz, 1H), 4.10 (br s, 1H), 3.62 (dd, J=13.0, 22.6 Hz, 1H), 2.76 (br s, 1H), 1.15-1.09 (m, 2H), 1.09 (s, 9H), 0.97 (t, J=7.9 Hz, 9H), 0.75-0.68 (m, 6H).

Intermediate 1a-7

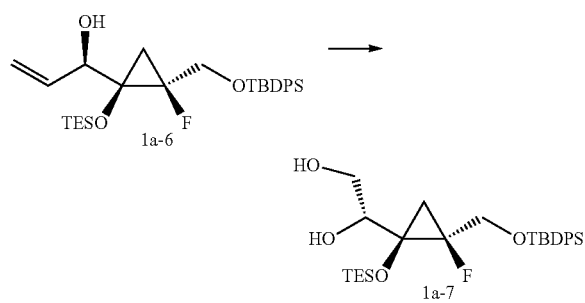

Step 10.

To a cloudy solution of compound 1a-6 (3.250 g, 6.313 mmol) in dichloromethane (150 mL) cooled at −78° C. was passed a stream of O$_3$ until the solution turned blue. O$_2$ was bubbled through the reaction mixture for 15 min. NaBH$_4$ (0.478 g, 12.63 mmol) was added in one portion, followed by MeOH (70 mL) at −78° C. After 15 min at −78° C., more NaBH$_4$ (0.120 g, 3.156 mmol) was added. After another 15 min at −78° C., the mixture was allowed to warm up to rt. Saturated NH$_4$Cl solution was added carefully to quench the reaction. The mixture was diluted with brine and the layers were separated. The aqueous layer was extracted with EtOAc. The combined organic layers were washed with brine, dried (Na$_2$SO$_4$), filtered and concentrated. The residue was purified by flash column chromatography (silica, EtOAc-hexanes) to afford compound 1a-7 as a colorless oil (3.100 g, 95%). $^1$H NMR (500 MHz, CDCl$_3$) δ 7.71-7.66 (m, 4H), 7.45-7.38 (m, 6H), 4.24 (dd, J=13.1, 17.8 Hz, 1H), 4.12 (dd, J=7.1, 13.2 Hz, 1H), 3.94-3.89 (m, 1H), 3.84-3.80 (m, 1H), 3.65 (dd, J=12.9, 22.1 Hz, 1H), 3.48-3.44 (m, 1H), 2.60 (d, J=6.5 Hz, 1H), 2.17-2.15 (m, 1H), 1.13-1.07 (m, 2H), 1.07 (s, 9H), 0.97 (t, J=7.9 Hz, 9H), 0.77-0.64 (m, 6H).

Intermediate 1a-8

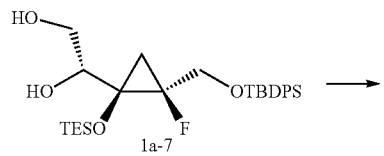

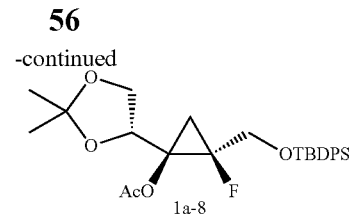

Step 11.

A solution of compound 1a-7 (3.100 g, 5.975 mmol) and PPTS (1.502 g, 5.975 mmol) in acetone/H$_2$O (9/1, 35 mL) was stirred at rt for 5 h. The mixture was concentrated. The residue was co-evaporated with toluene (*2), and used directly for next step.

Step 12.

A suspension of the crude product from step 10 (5.975 mmol at most) in acetone/2,2-dimethoxypropane (1/1, 50 mL) was heated at 50° C. for 3 h before being allowed to cool down and concentrated. The residue was purified by flash column chromatography (silica, EtOAc-hexanes) to afford the desired compound as a colorless oil (2.320 g, 86% over 2 steps). $^1$H NMR (500 MHz, CDCl$_3$) δ 7.70-7.66 (m, 4H), 7.46-7.38 (m, 6H), 4.28-4.10 (m, 3H), 4.02 (t, J=6.8 Hz, 1H), 3.67 (dd, J=13.2, 33.2 Hz, 1H), 2.55 (s, 1H), 1.44 (s, 3H), 1.36 (s, 3H), 1.27-1.17 (m, 2H), 1.04 (s, 9H).

Step 13.

To a solution of the compound from step 12 (2.320 g, 5.218 mmol) in CH$_2$Cl$_2$/pyridine (4/1, 50 mL) at rt was added Ac$_2$O (1.48 mL, 15.65 mmol), followed by DMAP (19.1 mg, 0.156 mmol). The mixture was stirred at rt for 2 h. Excess i-PrOH was added to quench the reaction. The mixture was concentrated. The residue was purified by flash column chromatography (silica, EtOAc-hexanes) to afford the compound 1a-8 as a colorless oil (2.510 g, 99%). $^1$H NMR (500 MHz, CDCl$_3$) δ 7.71-7.69 (m, 4H), 7.43-7.39 (m, 6H), 4.55 (t, J=6.6 Hz, 1H), 4.15 (t, J=12.6 Hz, 1H), 4.10-3.95 (m, 3H), 2.10 (s, 3H), 1.36-1.26 (m, 2H), 1.27 (s, 3H), 1.08 (s, 9H).

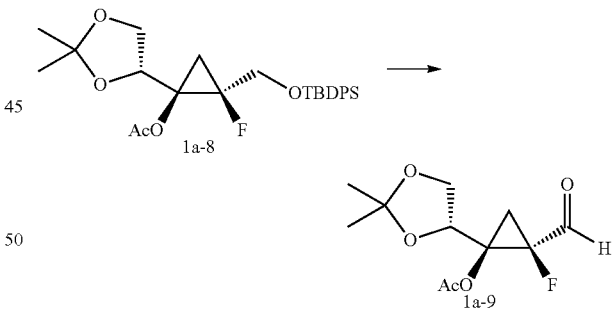

Step 14.

To a solution of the compound 1a-8 (2.510 g, 5.158 mmol) in THF (12 mL) at rt was added HF.Pyr (prepared by diluting commercial 70% (HF)$_x$.Pyr (1 volume) in pyridine (4 volume), 9 mL). The mixture was stirred at rt for 2 h before being diluted with EtOAc. Saturated NaHCO$_3$ solution and NaHCO$_3$ powder were added carefully until no bubble formed. The two layers were separated. The aqueous layer was extracted with EtOAc. The combined organic layers were washed with brine, dried (Na$_2$SO$_4$), filtered and concentrated. The residue was purified by flash column chromatography (silica, EtOAc-hexanes) to afford the desired alcohol as a colorless oil (1.180 g, 92%). $^1$H NMR (500 MHz, CDCl$_3$) δ 4.67 (t, J=7.4 Hz, 1H), 4.24 (dd, J=14.1, 17.7 Hz, 1H), 3.97-3.86 (m, 2H), 2.38 (br s, 1H), 2.08 (s, 3H), 1.46-1.30 (m, 2H), 1.38 (s, 3H), 1.33 (s, 3H).

Step 15.

To a solution of the compound from step 14 (1.180 g, 4.753 mmol) in CH$_2$Cl$_2$/pyridine (20/1, 42 mL) at rt was added Dess-Martin periodinane (4.032 g, 9.506 mmol). The mixture was stirred at rt for 2 h before being concentrated. The residue was dissolved in dichloromethane and purified by flash column chromatography (silica, EtOAc-hexanes) to afford compound 1a-9 as a colorless oil (0.878 g, 75%). $^1$H NMR (500 MHz, CDCl$_3$) δ 9.63 (d, J=10.7 Hz, 1H), 4.66 (t, J=6.2 Hz, 1H), 4.07-3.99 (m, 2H), 2.15 (dd, J=9.0, 14.1 Hz, 1H), 2.10 (s, 3H), 1.81 (dd, J=8.9, 21.7 Hz, 1H), 1.43 (s, 3H), 1.33 (s, 3H).

Intermediate 1a-10

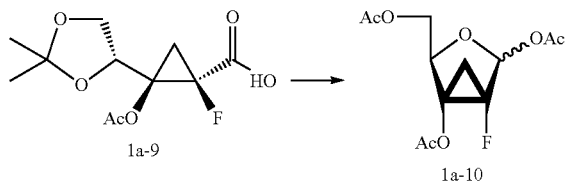

Step 16.

A solution of the compound 1a-9 (0.602 g, 2.445 mmol) in HOAc/H$_2$O (4/1, 15 mL) was stirred at rt for 26 h before being diluted with toluene and concentrated. The residue was co-evaporated with toluene (*2), dried under vacuum to afford the desired cyclization product as a slightly yellow oil (0.533 g), which was used directly for next step. $^1$H NMR (500 MHz, CDCl$_3$) δ (major diastereomer) 5.37 (d, J=1.7 Hz, 1H), 4.55 (t, J=4.8 Hz, 1H), 3.78-3.63 (m, 2H), 2.17 (s, 3H), 2.09 (s, 3H), 1.74-1.39 (m, 2H).

Step 17.

To a solution of the compound from step 16 (0.533 g, 2.445 mmol at most) in CH$_2$Cl$_2$/pyridine (4/1, 20 mL) at rt was added Ac$_2$O (1.39 mL, 14.67 mmol) dropwise, followed by DMAP (6.0 mg, 0.0489 mmol). The mixture was stirred at rt for 14 h. Isopropanol (1.13 ml, 14.67 mmol) was added at rt to quench the reaction. The mixture was freed of volatiles. The residue was purified by flash column chromatography (silica, EtOAc-hexanes) to afford compound 1a-10 as a colorless oil (0.262 g, 37% over 2 steps). 1H NMR (500 MHz, C$_6$D$_6$) δ (major diastereomer) 6.41 (d, J=1.5 Hz, 1H), 4.74 (m, 1H), 4.39 (dd, J=3.2, 12.2 Hz, 1H), 3.99-3.94 (m, 1H), 1.58 (s, 3H), 1.56 (s, 3H), 1.45 (s, 3H), 1.36-1.10 (m, 2H).

Intermediate 1a-11

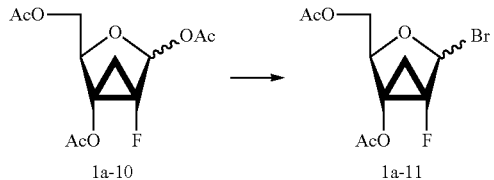

Step 18.

To a solution of the compound 1a-10 (0.100 g, 0.345 mmol) in dichloromethane (4 ml) was added HBr (33% in HOAc, 1 mL). The mixture was stirred in a sealed tube at rt overnight before being concentrated. The residue was co-evaporated with dichloromethane (*1), benzene (*2), dried under vacuum to afford compound 1a-11 as a brown oil, which was used directly for next step. $^1$H NMR (500 MHz, C$_6$D$_6$) δ 5.82 (d, J=2.0 Hz, 1H), 4.58 (dd, J=3.4, 8.2 Hz, 1H), 4.35 (dd, J=3.4, 12.5 Hz, 1H), 1.54 (s, 3H), 1.42 (s, 3H), 1.24 (dd, J=9.0, 18.1 Hz, 1H), 1.12 (t, J=9.0 Hz, 1H).

Example 1

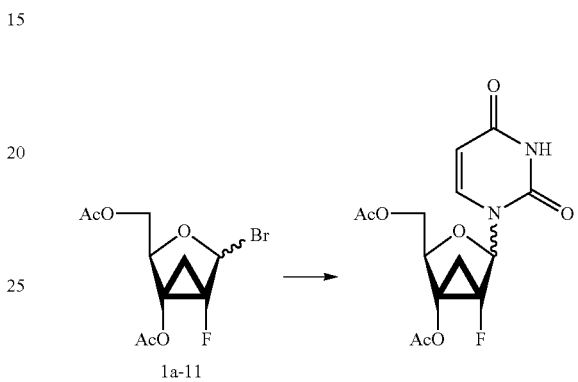

Step 19.

To a suspension of uracil (0.116 g, 1.034 mmol) in acetonitrile (5 mL) was added N,O-bis(trimethylsilyl)acetamide (0.53 mL, 2.067 mmol). The mixture was heated in a sealed tube at 86° C. for 2 h before being allowed to cool down and concentrated. The residue was dried under vacuum for 30 min. A solution of the compound 1a-11 (0.345 mmol at most) in 1,2-dichloroethane (6 ml) was added. The mixture was stirred at 80° C. for 2 h before being allowed to cool down and concentrated. The residue was purified by chromatography (silica, EtOAc-hexanes) to afford the title compound as a yellow foam (84.0 mg, 71% over 2 steps, α/β ratio ~2/1). ESIMS m/z=343.23 [M+H]$^+$.

Example 2

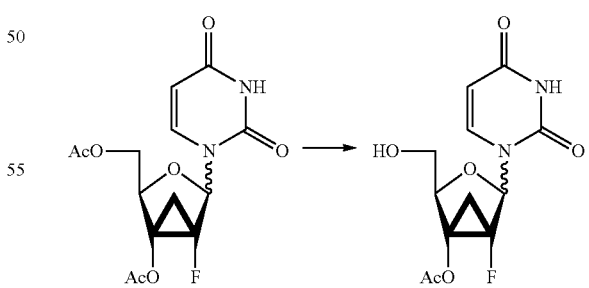

Step 20.

To a suspension of the compound from example 1 (43.0 mg, 0.126 mmol) and N,O-dimethylhydroxyamine hydrochloride (49.0 mg, 0.503 mmol) in THF (5 mL) cooled at −30° C. was added i-PrMgCl (2.0M in THF, 0.31 mL, 0.628 mmol) dropwise over 30 min. After the addition, the mixture was stirred at −30° C. for 10 min. More i-PrMgCl (2.0M in THF, 0.06 mL, 0.126 mmol) was added dropwise at −30° C. After 30 min at −30° C., more i-PrMgCl (2.0M in THF, 0.06 mL, 0.126 mmol) was added. After 30 min at −30° C., the reaction was quenched with excess Et₃N.HCl followed by saturated NH₄Cl solution. The mixture was allowed to warm up to rt. THF was evaporated. The mixture was diluted with H₂O and EtOAc. The aqueous layer was extracted with dichloromethane (*5). The combined organic phases were washed with brine, dried (Na₂SO₄), filtered and concentrated. The residue was purified by chromatography (silica, EtOAc-dichloromethane) to afford the title compound as a light yellow foam (11.3 mg, 30%). ESIMS m/z=301.30 [M+H]⁺.

Example 3

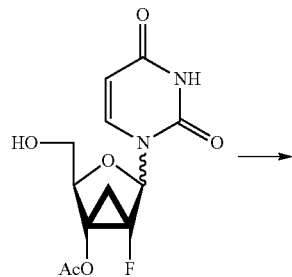

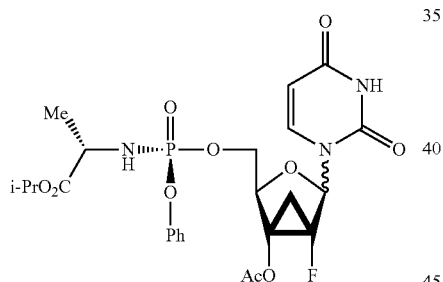

Step 21.

To a solution of the compound from example 2 (19.0 mg, 0.0633 mmol) in THF (2 mL) cooled at 0° C. was added t-BuMgCl (1.0M in THF, 0.32 mL, 0.316 mmol) dropwise. After the addition, the mixture was stirred at 0° C. for 30 min and then at rt for 30 min before being cooled back to 0° C. A solution of isopropyl((S)-(perfluorophenoxy)(phenoxy)-phosphoryl)-L-alaninate (86.1 mg, 0.190 mmol) in THF (0.4 mL) was added. The mixture was allowed to warm up to rt and stirred at rt for 1 h. More t-BuMgCl (1.0M in THF, 0.12 mL, 0.126 mmol) was added dropwise at rt. After 1 h at rt, more t-BuMgCl (1.0M in THF, 0.06 mL, 0.063 mmol) was added. After 30 min at rt, another batch of the solution of isopropyl((S)-(perfluorophenoxy)(phenoxy)phosphoryl)-L-alaninate (43.0 mg, 0.0950 mmol) in THF (0.2 mL) was added. After 1 h at rt, the reaction was quenched with saturated NH₄Cl solution. The mixture was diluted with H₂O and EtOAc. The aqueous layer was extracted with dichloromethane (*2). The combined organic phases were washed with brine, dried (Na₂SO₄), filtered and concentrated. The residue was purified by chromatography (silica, EtOAc-dichloromethane) to afford the title compound as a yellow foam (9.5 mg, 26%). ESIMS m/z=570.17 [M+H]⁺.

Example 4

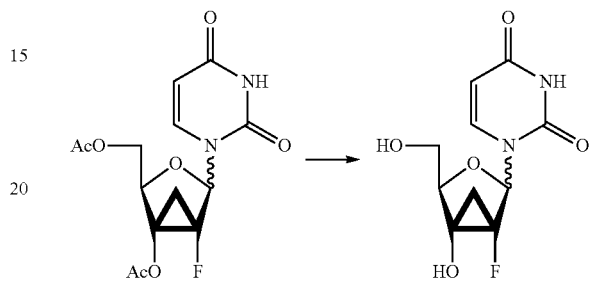

Step 22.

To a solution of the compound from example 1 (55.0 mg, 0.161 mmol) in CH₂Cl₂/MeOH (9/1, 4 mL) was added PTSA.H₂O (61.1 mg, 0.321 mmol) at rt. The reaction mixture was heated at 40° C. in a sealed tube for 24 h before being allowed to cool down and freed of volatiles. The residue was dried under vacuum to afford the title compound as a yellow oil containing 2 equivalents of PTSA, which was used directly for next step without further purification. ESIMS m/z=259.33 [M+H]⁺.

Example 5

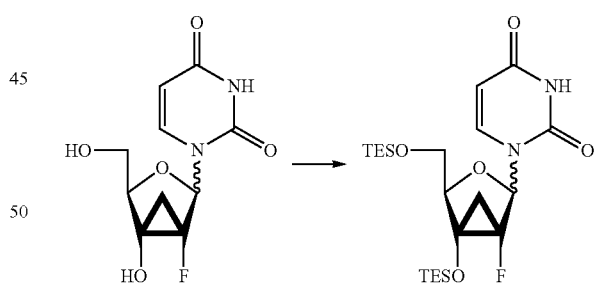

Step 23.

To a solution of the compound from example 4 (0.161 mmol at most, contains 2 equivalent of PTSA) in CH₂Cl₂/pyridine (9/1, 4 mL) heated at 40° C. was added TESOTf (0.14 mL, 0.619 mmol) dropwise. The reaction mixture was stirred at 40° C. for 3 minutes before EtOH (0.40 mL) was added to quench the reaction. The mixture was allowed to cool down and freed of volatiles. The residue was taken up in CH₂Cl₂ and purified by flash column chromatography (silica, CH₂Cl₂-EtOAc) to afford the title compound as a colorless oil (43.4 mg, 55% over 2 steps). ESIMS m/z=487.37 [M+H]⁺.

Example 6

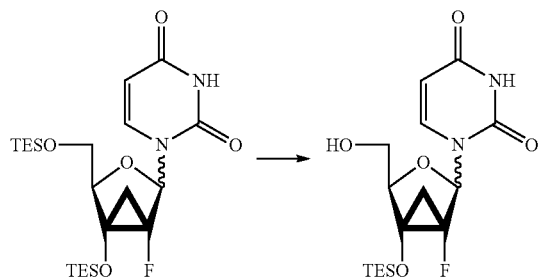

Step 24.

To a solution of the compound from example 5 (29.4 mg, 0.0604 mmol) in acetone/H$_2$O (9/1, 2 mL) cooled at 0° C. was added PPTS (3.0 mg, 0.0121 mmol). The reaction mixture was stirred at 0° C. for 2 h before being diluted with EtOAc and brine. The aqueous layer was extracted with EtOAc (*2). The combined organic layers were dried (Na$_2$SO$_4$), filtered and concentrated. The residue was purified by preparative thin layer chromatography (silica, EtOAc) to afford the title compound as a white solid (6.2 mg, 19%) along with the undesired α-anomer (14.7 mg, 44%). ESIMS m/z=373.20 [M+H]$^+$ for example 6.

Example 7

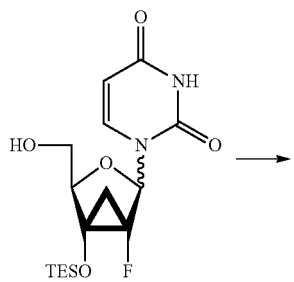

Step 25.

To a solution of the compound from example 6 (10.0 mg, 0.0268 mmol) in THF (1.5 mL) cooled at 0° C. was added t-BuMgCl (1.0M in THF, 0.11 mL, 0.107 mmol) dropwise. After the addition, the mixture was stirred at 0° C. for 30 min and then at rt for 30 min. A solution of isopropyl((S)-(perfluorophenoxy)(phenoxy)phosphoryl)-L-alaninate (24.3 mg, 0.0537 mmol) in THF (0.1 mL) was added at rt. The mixture was stirred at rt for 1 h. Another batch of the solution of isopropyl((S)-(perfluorophenoxy)(phenoxy)phosphoryl)-L-alaninate (24.3 mg, 0.0537 mmol) in THF (0.1 mL) was added at rt. After 1 h at rt, a third batch of the solution of isopropyl((S)-(perfluorophenoxy)(phenoxy)phosphoryl)-L-alaninate (24.3 mg, 0.0537 mmol) in THF (0.1 mL) was added. After 1 h, more t-BuMgCl (1.0M in THF, 0.05 mL, 0.0537 mmol) was added dropwise at rt. After 30 min at rt, more t-BuMgCl (1.0M in THF, 0.03 mL, 0.0268 mmol) was added. After 30 min at rt, the reaction was quenched with saturated NH$_4$Cl solution. The mixture was diluted with H$_2$O and EtOAc. The organic layer was washed with brine, dried (Na$_2$SO$_4$), filtered and concentrated. The residue was purified by flash column chromatography (silica, EtOAc-dichloromethane) to afford the title compound as a yellow oil (10.0 mg, 58%). ESIMS m/z=642.25 [M+H]$^+$.

Example 8

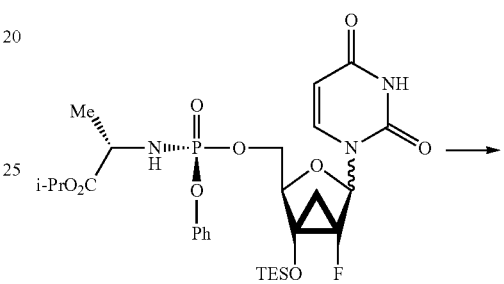

Example 7

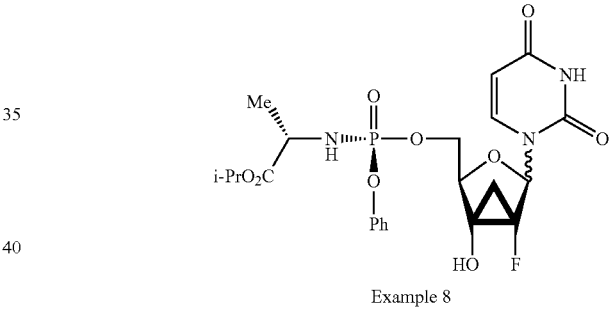

Example 8

Step 26.

To a solution of the compound from example 7 (5.0 mg, 7.79 μmol) in acetone/H$_2$O (9/1, 1.0 mL) at rt was added PPTS (2.0 mg, 7.79 μmol). The resulting solution was stirred at rt for 6 h before being freed of volatiles to afford the crude title compound as a colorless oil. ESIMS m/z=528.15 [M+H]$^+$.

In Vitro Antiviral Activity

Cells

Human embryonic lung (HEL) fibroblasts (ATCC CCL137) or E$_6$SM (human diploid fibroblasts) are used at low passages (10 to 17). They are maintained in minimum essential medium (MEM) supplemented with 10% heat-inactivated fetal calf serum (FCS),1% L-glutamine and 0.3% sodium bicarbonate.

HeLa cells are used and maintained in minimum essential medium (MEM) supplemented with 10% heat-inactivated fetal calf serum (FCS), 1% L-glutamine and 0.3% sodium bicarbonate.

Vero cells are used and maintained in minimum essential medium (MEM) supplemented with 10% heat-inactivated fetal calf serum (FCS), 1% L-glutamine and 0.3% sodium bicarbonate.

Primary human keratinocytes (PHKs) are isolated from neonatal foreskins. Tissue fragments are incubated with trypsin-EDTA for 1 h at 37° C. The epithelial cells are detached and cultured with Serum-Free Keratinocyte Medium (Gibco, Invitrogen Corporation, UK) supplemented with 0.5 µg/ml hydrocortisone, 10 ng/ml epidermal growth factor, 10% fetal calf serum, 2 mmol/liter L-glutamine, 10 mmol/liter HEPES, 1 mmol/liter sodium pyruvate, $10^{-10}$ mol/liter cholera toxin, 5 tg:ml insulin, 5 ug/ml transferrine and $15\times10^{-4}$ mg/ml 3,3',5'-triiodo-L-thyronine.

Primary lamb keratinocytes (PLKs) are isolated from foreskin tissue of 3 to 12 month old lambs. Thin sheets of foreskin tissue are cut in small pieces and then incubated with trypsin-EDTA (Gibco, Invitrogen Corporation, UK) for 30 minutes at 37° C. Trypsinized cells are filtered and then centrifuged for 10 minutes at 1200 rpm. The cell pellet is resuspended in the growth medium (a mixture of Ham's F12 and Dulbecco's modified Eagle's medium (1:4), supplemented with 0.5 µg/ml hydrocortisone, 10 ng/ml epidermal growth factor, 10% fetal calf serum, 2 mmol/liter L-glutamine, 10 mmol/liter HEPES, 1 mmol/liter sodium pyruvate, 10-10 mol/liter cholera toxin, 5 tg:ml insulin, 5 Rg/ml transferring, and 15×10-4 mg/ml 3,3'.5'-triiodo-L-thyronine.

UC1-B cells (murine embryo fibroblasts, ATCC 6465-CRL) and BS-C-1 cells (African green monkey kidney cell line, ATCC CCL-26) are maintained in minimum essential medium (MEM) supplemented with 10% heat-inactivated fetal calf serum (FCS), 1% L-glutamine and 0.3% sodium bicarbonate.

Primary human keratinocytes (PHKs) are isolated from neonatal foreskins. Tissue fragments are incubated with trypsin-EDTA for 1 h at 37° C. The epithelial cells are detached and cultured with Serum-Free Keratinocyte Medium (Gibco, Invitrogen Corporation, UK) supplemented with 0.5 µg/ml hydrocortisone, 10 ng/ml epidermal growth factor, 10% fetal calf serum, 2 mmol/liter L-glutamine, 10 mmol/liter HEPES, 1 mmol/liter sodium pyruvate, 10-10 mol/liter cholera toxin, 5 µg/ml insulin, 5 Rg/ml transferring, and $15\times10^{-4}$ mg/ml 3,3',5'-triiodo-L-thyronine.

Also other cell types are used in the experiments such as described herein, namely human T-lym-phoblast HSB-2 and MOLT-3 cells.

Viruses

The Human Cytomegalovirus (HCMV) reference strains AD-169 (ATCC VR538) and Davis (ATCC VR 807) are used. Virus stocks are prepared in HEL cells. When 100% cytopathogenic effect is obtained, the cells and supernatant are frozen. After one cycle freezing/thawing, the cell debris is removed by centrifugation and the supernatant stored in aliquots at −80° C.

The Varicella-Zoster Virus (VZV) reference strains Oka (ATCC VR-795) and YS are used as well as the thymidine kinase (TK)-deficient strains YS-R and 07-1. Virus stocks are prepared as described previously (Andrei G. et al., Eur. J. Clin. Microbiol. Infect. Dis. 1995, 14 (4), 318-329). Virus stocks are prepared in HEL cells. When 70% cytopathogenic effect is obtained, the cells are trypsinized and resuspended in medium containing 10% DMSO and stored in aliquots at −80° C.

The Herpes simplex virus (HSV) reference strains KOS (ATCC VR-1493), F (ATCC VR-733), McIntyre (ATCC VR-539), G (ATCC VR-734), 196, Lyons are used as well as the thymidine kinase (TK)-deficient strain KOS ACVr. Virus stocks are prepared in E$_6$SM cells. When 100% cytopathogenic effect is obtained, the cells and supernatant are frozen. After one cycle freezing/thawing, the cell debris is removed by centrifugation and the supernatant stored in aliquots at −80° C.

Also human herpesvirus 6 strains are used, namely HHV-6A (strain GS) and HHV-6B (strain Z29).

Human adenovirus type 2: Ad2 as clinical isolate is used on HEL cells.

For the orthopoxviruses, the vaccinia virus strains Lederle chorioallantoic (ATCC CCL-137), Western Reserve (ATCC VR-119), Lister (VR-1549, Elstree), Copenhagen strain and the Cowpox virus strain Brighton (ATCC VR-302) are used. For the parapoxviruses, the orf virus strain NZ 2 (ATCC VR-1548) is used. Virus stocks are prepared as described previously. Virus stocks are prepared in HEL cells. When 100% cytopathogenic effect is obtained, the cells and supernatant are frozen. After one cycle freezing/thawing, the cell debris is removed by centrifugation and the supernatant stored in aliquots at −80° C. Also recombinant virus strains resistant against HPMPC are used to test the activity of the compounds of the present invention. These recombinant virus strains are prepared as known in the art.

Vesicular stomatitis virus, Coxsakie virus B4, parainfluenza-3 virus, respiratory syncytial virus, Reovirus-1, Sindbis virus and Punta Toro virus are taken as representative for the respective following families of viruses: rhabdoviruses, enteroviruses, paramyxoviruses (pneumovivuses/RSV), reoviruses, togaviruses and bunyaviruses. Virus stocks are prepared as described previously. Virus stocks are prepared in the appropriated cell line for each virus. When 100% cytopathogenic effect is obtained, the cells and supernatant are frozen. After one cycle freezing/thawing, the cell debris is removed by centrifugation and the supernatant stored in aliquots at −80° C.

Polyomavirus: Four murine polyomavirus strains [MN/RDE Toronto, PTA, 2PTA2, and LID-1] and three simian polyomavirus strains [SV40 (a vacuolating agent) strain A2895, SV40 PML-1 strain EK, and SV40 PML-2 strain DAR] are used. The polyomavirus strains and the SV40 strains are propagated and assessed in UC1-B and BS-C-1 cells, respectively.

Moluscum contagiosum virus (MCV): Fresh lesions obtained from preadolescent children are used to recover the clinical samples of molluscum contagiosum virus.

Minimal Cytotoxic Concentration and Cytotoxicity Assays

Minimal cytotoxic concentration for the different cell lines: The minimal cytotoxic concentration (MCC) is the lowest concentration of the compound in the antiviral assay where morphological changes characteristic of cytotoxicity are recorded.

Cytotoxicity assay for HEL and PHK cells: Toxicity of the compounds for the host cells is based on inhibition of cell growth. The cells are seeded at $4\times10^3$ cells per well in a volume of 0.1 ml into 96-well microtiter plates and allowed to proliferate for 24 h in MEM containing 20% FCS, 0.1% L-glutamine, and 0.3% sodium bicarbonate. Twenty-four hours later, MEM (with 2% FCS, 0.1% L-glutamine, and 0.3% sodium bicarbonate) containing different concentrations (in duplicate) of the test compounds is added (0.1 ml/well). After three days of incubation at 37° C. in 5% CO$_2$ atmosphere, the cell number is determined with a Coulter counter. The toxicity of the compounds is expressed as CC$_{50}$ or the compound concentration required to reduce cell growth by 50%, as compared to an untreated control.

(1). Antiviral Assays for VZV and HCMV in HEL Cells.

VZV- and HCMV-drug susceptibility assays are performed as previously described (Andrei G., et al., Eur. J. Clin. Microbiol. Infect. Dis. 1991, 10 (12), 1026-1033).

Confluent HEL cells in 96-well microtiter plates are infected with 20 pfu of cell-associated virus per well (VZV) or 100 pfu of cell-free virus (HCMV). After 2 hours incubation, the inoculum is removed and replaced by the different dilutions (in duplicate) of the tested molecules. After 5 (VZV) or 7 (HCMV) days of incubation the cells are fixed and stained with Giemsa. The activity is determined by counting the number of plaques (VZV) or evaluating the CPE (HCMV) for each dilution. The activity is expressed as $EC_{50}$ or the effective compound concentration required to reduce virus-induced cytopathicity (CPE) by 50%, as compared to the untreated control.

(2). Antiviral Assays for HSV, VSV, Coxsackie, RSV, Para-influenza-3, Reovirus, and Punta Toro Virus.

Confluent $E_6SM$ cells (HSV and VSV), HeLa cells (VSV, Coxsackie and RSV), Vero cells (Para-influenza, Reovirus, Sindbis, and Punta Toro viruses) grown in 96-well microtiter plates are infected with 100 $CCID_{50}$, of cell free viruses. After 1 hour incubation, (2 hours for RSV), the inocu-lum is removed and replaced by the different dilutions (in duplicate) of the tested molecules. After 2 to 3 days incubation the CPE is evaluated under the microscope. The activity is expressed as $EC_{50}$, or effective compound concentration required reducing virus-induced cytopathicity (CPE) by 50%, as compared to the untreated control.

More specifically for anti-Coxsackie virus assay: Ninety-six-well cell culture plates can be seeded with Vero cells in DMEM medium containing 10 fetal calf serum (FCS) so that cells reach confluency 24-48 hr later. Medium can then be removed and serial 5-fold dilutions of the test compounds can be added in a total volume of 100 µl, after which the virus inoculum (100 µl) can be added to each well. The virus inoculum used results normally in a 90-100% destruction of the cell monolayer after 5 days incubation at 37° C. Uninfected cells and cells receiving virus without compound can be included in each assay plate. After 5 days, the medium can be removed and 90 IA of DMEM-FCS and 10 µl of MTS/PMS solution (Promega) is added to each well. Following a 2 h incubation period at 37° C., the optical density of the wells can be read at 498 nm in a microplate reader. The 50% effective concentration ($EC_{50}$) value can than be defined as the concentration of compound that protects 50% of the cell monolayer from the virus-induced cytopathic effect.

(3). Antiviral Assay for Human Adenovirus Type 2

Human embryonic lung (HEL) fibroblast cells are seeded in 96-well plates at 10000 cells per well and incubated for 4-5 days until confluency. To each well, 50 µl of Ad2 (a clinical isolate of adenovirus type 2) is added, diluted in medium to obtain a virus input of 5 PFU per well. After 2 hr at 37° C., virus is aspirated and replaced by serial dilutions of the test compounds (200 ul per well). Mock-treated cultures receiving only the test compounds are included in each plate. After 10-12 days incubation at 37° C., microscopy is performed to score the virus-induced cyto-pathic effect (CPE), and compound toxicity, expressed as the Minimum Cytotoxic Concentration. The plates are then subjected to the MTS-based calorimetric assay for cell viability according to the Manufacturer's instructions (Promega, Leiden, The Netherlands). The A490 nm values, corrected for cytotoxicity exerted by the test compounds (as determined in mock-infected cultures), are used to calculate the percent cell viability. The 50% effective concentration ($EC_{50}$) is determined by extrapolation and defined as the compound concentration that produced 50% protection against the virus. (Naesens et al., Antimicrob. Agents Chemother. (2005), 49: 1010-1016).

(4). Antiviral Assays for Human Herpesvirus 6

HHV-6 assays are performed in human T-lympho-blast HSB-2 (for HHV-6A, strain GS) and MOLT-3 (for HHV-6B, strain Z29) cells. Virus stocks are added to concentrated cell suspensions at a multiplicity of infection of 100 $CCID_{50}$ (50% cell culture infective dose) per $10^6$ cells. After 2 hr, cells are centrifuged to remove unadsorbed virus, resuspended in medium containing serial dilutions of the compounds, and transferred to 48-well plates. After 10-12 days incubation, viral CPE and compound cytotoxicity are scored by microscopy, and total DNA is extracted from the cells for quantitation of the viral DNA by qPCR. Anti-HHV-6 activity is expressed as $EC_{50}$ i.e., the compound concentration that produces 50% inhibition of virus replication, as estimated from the CPE score, or the amount of viral DNA as measured in the PCR assay.

For qPCR analysis on the DNA extracts, the SYBR® Green qPCR method is used. The forward and reverse primers are chosen to amplify a 150-bp fragment of the HHV-6 U67 gene. A standard curve is obtained by amplification of known amounts of a pGEM T-vector in which a 511-bp fragment of the HHV-6 U67 gene is inserted using common cloning procedures. These standard curves are used to convert the cycle threshold ($C_t$) values for the cell extracts into the absolute number of HHV-6 DNA copies. The $EC_{50}$, value is calculated by extrapolation as the compound concentration at which the number of viral DNA copies at 10-12 days p.i. is 50% compared to the value obtained for the virus control. (De Bolle et al., Biochem. Pharmacol. (2004), 67: 325-336.)

(5). Antiviral Assays for Ortho- and Parapoxviruses

These susceptibility assays are performed as previously described. Confluent HEL (ortho- and parapoxvi-ruses), PHK (orthopoxviruses) and PLK (parapoxviruses) cells in 96-well microtiter plates are infected with a viral inoculum with a titer ranging from 20 to 60 pfu/well. After 2 hours of incubation at 37° C. and 5% $CO_2$, residual virus is removed and the infected cells are further incubated with medium containing serial dilutions of the compounds (in duplicate). After 2 to 3 days of incubation at 37° C. and 5% $CO_2$, the viral cytopathic effect (CPE) is recorded. The activity is expressed as $EC_{50}$, or effective compound concentration required reducing virus-induced cytopathicity (CPE) by 50%, as compared to the untreated control.

(6). Antiviral assays for (primate or murine) polyomavirus

Confluent monolayers of UC1-B or BS-C-1 cells grown in 96-well microtiter plates are infected with 100 $CCID_{50}$ of cell-free viruses. After 2 hours incubation, the inoculum is removed and replaced by the different dilutions (in duplicate) of the tested molecules. After 4 to 5 days (polyomavirus strains) or 6 to 7 days (SV40 strains) of incubation virus induced cytopathic effect (CPE) is monitored microscopically. The activity is expressed as $EC_{50}$ or effective compound concentration required for reducing virus-induced cytopathicity (CPE) by 50%, as compared to the untreated control.

Cytotoxicity Assays.

Confluent monolayers of UC-B or BS-C-1 grown in 96-well microtiter plates are incubated with different concentrations of the compounds (in duplicate) for 5 to 6 days. The cells are then trypsinized and the cell number is determined with a Coulter Counter. The toxicity of the compounds is expressed as $CC_{50}$ or compound concentration required for reducing cell number by 50%, as compared to an untreated control. The selectivity index is the ratio of $CC_{50}$ for cell toxicity to $EC_{50}$ for viral CPE.

(7). Antiviral Assays for Moluscum Contagio Sum Virus (MCV)

Twenty-four hour-old monolayers of PHKs grown in 96-well microtiter plates are infected with 100 $CCID_{50}$ of cell-free viruses. After 2 hours incubation, the inoculum is removed and replaced by the different dilutions (in duplicate) of the tested molecules. After 6 to 7 days of incubation virus induced cytopathic effect (CPE), characterized by the appearance of large infected cells, with internal organelles dislocated and obliterated by a large intracytoplasmic inclusion, is monitored microscopically. The activity is expressed as $EC_{50}$ or effective compound concentration required for reducing virus-induced cytopathicity (CPE) by 50%, as compared to the untreated control.

(8). Screening Assays for DENV, JEV, POWV, WNV, YFV, PTV, RVFV, CHIKV, EEEV, VEEV, WEEV, TCRV, PCV, JUNV, MPRLV Primary Cytopathic Effect (CPE) Reduction Assay.

Four-concentration CPE inhibition assays are performed. Confluent or near-confluent cell culture monolayers in 96-well disposable microplates are prepared. Cells are maintained in MEM or DMEM supplemented with FBS as required for each cell line. For antiviral assays the same medium is used but with FBS reduced to 2% or less and supplemented with 50 µg/ml gentamicin. The test compound is prepared at four $log_{10}$ final concentrations, usually 0.1, 1.0, 10, and 100 µg/ml or µM. The virus control and cell control wells are on every microplate. In parallel, a known active drug is tested as a positive control drug using the same method as is applied for test compounds. The positive control is tested with each test run. The assay is set up by first removing growth media from the 96-well plates of cells. Then the test compound is applied in 0.1 ml volume to wells at 2× concentration. Virus, normally at <100 50% cell culture infectious doses ($CCID_{50}$) in 0.1 ml volume, is placed in those wells designated for virus infection. Medium devoid of virus is placed in toxicity control wells and cell control wells. Virus control wells are treated similarly with virus. Plates are incubated at 37° C. with 5% $CO_2$ until maximum CPE is observed in virus control wells. The plates are then stained with 0.011% neutral red for approximately two hours at 37° C. in a 5% $CO_2$ incubator. The neutral red medium is removed by complete aspiration, and the cells may be rinsed 1× with phosphate buffered solution (PBS) to remove residual dye. The PBS is completely removed and the incorporated neutral red is eluted with 50% Sorensen's citrate buffer/50% ethanol (pH 4.2) for at least 30 minutes. Neutral red dye penetrates into living cells, thus, the more intense the red color, the larger the number of viable cells present in the wells. The dye content in each well is quantified using a 96-well spectrophotometer at 540 nm wavelength. The dye content in each set of wells is converted to a percentage of dye present in untreated control wells using a Microsoft Excel computer-based spreadsheet. The 50% effective ($EC_{50}$, virus-inhibitory) concentrations and 50% cytotoxic ($CC_{50}$, cell-inhibitory) concentrations are then calculated by linear regression analysis. The quotient of $CC_{50}$ divided by $EC_{50}$ gives the selectivity index (SI) value.

Secondary CPE/Virus Yield Reduction (VYR) Assay.

This assay involves similar methodology to what is described in the previous paragraphs using 96-well microplates of cells. The differences are noted in this section. Eight half-$log_{10}$ concentrations of inhibitor are tested for antiviral activity and cytotoxicity. After sufficient virus replication occurs, a sample of supernatant is taken from each infected well (three replicate wells are pooled) and held for the VYR portion of this test, if needed. Alternately, a separate plate may be prepared and the plate may be frozen for the VYR assay. After maximum CPE is observed, the viable plates are stained with neutral red dye. The incorporated dye content is quantified as described above. The data generated from this portion of the test are neutral red $EC_{50}$, $CC_{50}$, and SI values. Compounds observed to be active above are further evaluated by VYR assay. The VYR test is a direct determination of how much the test compound inhibits virus replication. Virus that is replicated in the presence of test compound is titrated and compared to virus from untreated, infected controls. Titration of pooled viral samples (collected as described above) is performed by endpoint dilution. This is accomplished by titrating logio dilutions of virus using 3 or 4 microwells per dilution on fresh monolayers of cells by endpoint dilution. Wells are scored for presence or absence of virus after distinct CPE (measured by neutral red uptake) is observed. Plotting the $log_{10}$ of the inhibitor concentration versus $log_{10}$ of virus produced at each concentration allows calculation of the 90% (one $log_{10}$) effective concentration by linear regression. Dividing $EC_{90}$ by the $CC_{50}$ obtained in part 1 of the assay gives the SI value for this test.

(9). Screening Assays for Lassa Fever Virus (LASV)

Primary Lassa Fever Virus Assay.

Confluent or near-confluent cell culture monolayers in 12-well disposable cell culture plates are prepared. Cells are maintained in DMEM supplemented with 10% FBS. For antiviral assays the same medium is used but with FBS reduced to 2% or less and supplemented with 1% penicillin/streptomycin. The test compound is prepared at four $log_{10}$ final concentrations, usually 0.1, 1.0, 10, and 100 µg/ml or µM. The virus control and cell control will be run in parallel with each tested compound. Further, a known active drug is tested as a positive control drug using the same experimental set-up as described for the virus and cell control. The positive control is tested with each test run. The assay is set up by first removing growth media from the 12-well plates of cells, and infecting cells with 0.01 MOI of LASV strain Josiah. Cells will be incubated for 90 min: 500 µl inoculum/M12 well, at 37° C., 5% $CO_2$ with constant gentle rocking. The inoculums will be removed and cells will be washed 2× with medium. Then the test compound is applied in 1 ml of total volume of media. Tissue culture supernatant (TCS) will be collected at appropriate time points. TCS will then be used to determine the compounds inhibitory effect on virus replication. Virus that is replicated in the presence of test compound is titrated and compared to virus from untreated, infected controls. For titration of TCS, serial ten-fold dilutions will be prepared and used to infect fresh monolayers of cells. Cells will be overlaid with 1% agarose mixed 1:1 with 2×MEM supplemented with 10% FBS and 1% penicillin, and the number of plaques determined. Plotting the $log_{10}$ of the inhibitor concentration versus $log_{10}$ of virus produced at each concentration allows calculation of the 90% (one $log_{10}$) effective concentration by linear regression.

Secondary Lassa Fever Virus Assay.

The secondary assay involves similar methodology to what is described in the previous paragraphs using 12-well plates of cells. The differences are noted in this section. Cells are being infected as described above but this time overlaid with 1% agarose diluted 1:1 with 2×MEM and supplemented with 2% FBS and 1% penicillin/streptomycin and supplemented with the corresponding drug concentration. Cells will be incubated at 37° C. with 5% $CO_2$ for 6 days. The overlay is then removed and plates stained with 0.05% crystal violet in 10% buffered formalin for approximately twenty minutes at room temperature. The plates are then ished, dried and the number of plaques counted. The number of plaques is in each set of compound dilution is converted to a percentage relative to the untreated virus control. The 50% effective (EC50, virus-inhibitory) concentrations are then calculated by linear regression analysis.

(10). Screening Assays for Ebola virus (EBOV) and Nipah virus (NIV) Primary Ebola/Nipah virus assay.

Four-concentration plaque reduction assays are performed. Confluent or near-confluent cell culture monolayers in 12-well disposable cell culture plates are prepared. Cells are maintained in DMEM supplemented with 10% FBS. For antiviral assays the same medium is used but with FBS reduced to 2% or less and supplemented with 1% penicillin/streptomycin. The test compound is prepared at four login final concentrations, usually 0.1, 1.0, 10, and 100 μg/ml or μM. The virus control and cell control will be run in parallel with each tested compound. Further, a known active drug is tested as a positive control drug using the same experimental set-up as described for the virus and cell control. The positive control is tested with each test run. The assay is set up by first removing growth media from the 12-well plates of cells. Then the test compound is applied in 0.1 ml volume to wells at 2× concentration. Virus, normally at approximately 200 plaque forming units in 0.1 ml volume, is placed in those wells designated for virus infection. Medium devoid of virus is placed in toxicity control wells and cell control wells. Virus control wells are treated similarly with virus. Plates are incubated at 37° C. with 5% $CO_2$ for one hour. Virus-compound inoculums will be removed, cells washed and overlaid with 1.6% tragacanth diluted 1:1 with 2×MEM and supplemented with 2% FBS and 1% penicillin/streptomycin and supplemented with the corresponding drug concentration. Cells will be incubated at 37° C. with 5% $CO_2$ for 10 days. The overlay is then removed and plates stained with 0.05% crystal violet in 10% buffered formalin for approximately twenty minutes at room temperature. The plates are then ished, dried and the number of plaques counted. The number of plaques is in each set of compound dilution is converted to a percentage relative to the untreated virus control. The 50% effective ($EC_{50}$, virus-inhibitory) concentrations are then calculated by linear regression analysis.

Secondary Ebola/Nlpah virus assay with VYR component.

The secondary assay involves similar methodology to what is described in the previous paragraphs using 12-well plates of cells. The differences are noted in this section. Eight half-$log_{10}$ concentrations of inhibitor are tested for antiviral activity. One positive control drug is tested per batch of compounds evaluated. For this assay, cells are infected with virus. Cells are being infected as described above but this time incubated with DMEM supplemented with 2% FBS and 1% penicillin/streptomycin and supplemented with the corresponding drug concentration. Cells will be incubated for 10 days at 37° C. with 5% $CO_2$, daily observed under microscope for the number of green fluorescent cells. Aliquots of supernatant from infected cells will be taken daily and the three replicate wells are pooled. The pooled supernatants are then used to determine the compounds inhibitory effect on virus replication. Virus that is replicated in the presence of test compound is titrated and compared to virus from untreated, infected controls. For titration of pooled viral samples, serial ten-fold dilutions will be prepared and used to infect fresh monolayers of cells. Cells are overlaid with tragacanth and the number of plaques determined. Plotting the $log_{10}$ of the inhibitor concentration versus $log_{10}$ of virus produced at each concentration allows calculation of the 90% (one $log_{10}$) effective concentration by linear regression.

(11). Anti-Dengue Virus Cytoprotection Assay

Cell Preparation: BHK21 cells (Syrian golden hamster kidney cells, ATCC catalog #CCL-I 0) are passaged in DMEM supplemented with 10% FBS, 2 mM L-glutamine, 100 U/mL penicillin, and 100 μg/mL streptomycin in T-75 flasks prior to use in the antiviral assay. On the day preceding the assay, the cells are split 1:2 to assure they are in an exponential growth phase at the time of infection. Total cell and viability quantification is performed using a hemocytometer and Trypan Blue dye exclusion. Cell viability is greater than 95% for the cells to be utilized in the assay. The cells are resuspended at $3 \times 10^3$ cells per well in tissue culture medium and added to flat bottom microtiter plates in a volume of 100 μL. The plates are incubated at 37° C./5% $CO_2$ overnight to allow for cell adherence. Monolayers are observed to be approximately 70% confluent.

Virus Preparation: The Dengue virus type 2 New Guinea C strain is obtained from ATCC (catalog#VR-1584) and is grown in LLC-MK2 (Rhesus monkey kidney cells; catalog #CCL-7.1) cells for the production of stock virus pools. An aliquot of virus pretitered in BHK21 cells is removed from the freezer (−80° C.) and allowed to thaw slowly to room temperature in a biological safety cabinet. Virus is resuspended and diluted into assay medium (DMEM supplemented with 2% heat-inactivated FBS, 2 mM L-glutamine, 100 U/mL penicillin, and 100 μg/mL streptomycin) such that the amount of virus added to each well in a volume of 100 μL is the amount determined to yield 85 to 95% cell killing at 6 days post-infection.

Plate Format: Each plate contains cell control wells (cells only), virus control wells (cells plus virus), triplicate drug toxicity wells per compound (cells plus drug only), as well as triplicate experimental wells (drug plus cells plus virus).

Efficacy and Toxicity XTT: Following incubation at 37° C. in a 5% $CO_2$ incubator, the test plates are stained with the tetrazolium dye XTT (2,3-bis(2-methoxy-4-nitro-5-sulfophenyl)-5-[(phenylamino)carbonyl]-2H-tetrazolium hydroxide). XTT-tetrazolium is metabolized by the mitochondrial enzymes of metabolically active cells to a soluble formazan product, allowing rapid quantitative analysis of the inhibition of virus-induced cell killing by antiviral test substances. XTT solution is prepared daily as a stock of 1 mg/mL in RPMI 1640. Phenazine methosulfate (PMS) solution is prepared at 0.15 mg/mL in PBS and stored in the dark at −20° C. XTT/PMS stock is prepared immediately before use by adding 40 μL of PMS per ml of XTT solution. Fifty microliters of XTT/PMS is added to each well of the plate and the plate is reincubated for 4 hours at 37° C. Plates are sealed with adhesive plate sealers and shaken gently or inverted several times to mix the soluble formazan product and the plate is read spectrophotometrically at 450/650 nm with a Molecular Devices Vmax plate reader.

Data Analysis: Raw data is collected from the Softmax Pro 4.6 software and imported into a Microsoft Excel spreadsheet for analysis. The percent reduction in viral cytopathic effect compared to the untreated virus controls is calculated for each compound. The percent cell control value is calculated for each compound comparing the drug treated uninfected cells to the uninfected cells in medium alone.

(12). Anti-RSV Cytoprotection Assay

Cell Preparation: HEp2 cells (human epithelial cells, ATCC catalog#CCL-23) are passaged in DMEM supplemented with 10% FBS, 2 mM L-glutamine, 100 U/mL penicillin, 100 μg/mL streptomycin 1 mM sodium pyruvate, and 0.1 mM NEAA, in T-75 flasks prior to use in the antiviral assay. On the day preceding the assay, the cells are split 1:2 to assure they are in an exponential growth phase at the time of infection. Total cell and viability quantification is performed using a hemocytometer and Trypan Blue dye exclusion. Cell viability is greater than 95% for the cells to be utilized in the assay. The cells are resuspended at $1\times10^4$ cells per well in tissue culture medium and added to flat bottom microtiter plates in a volume of 100 µL. The plates are incubated at 37° C./5% $CO_2$ overnight to allow for cell adherence.

Virus Preparation: The RSV strain Long and RSV strain 9320 are obtained from ATCC (catalog#VR-26 and catalog #VR-955, respectively) and are grown in HEp2 cells for the production of stock virus pools. A pretitered aliquot of virus is removed from the freezer (−80° C.) and allowed to thaw slowly to room temperature in a biological safety cabinet. Virus is resuspended and diluted into assay medium (DMEM supplemented with 2% heat-inactivated FBS, 2 mM L-glutamine, 100 U/mL penicillin, 100 µ,g/mL streptomycin, 1 mM sodium pyruvate, and 0.1 mM NEAA) such that the amount of virus added to each well in a volume of 100 µL is the amount determined to yield 85 to 95% cell killing at 6 days post-infection. Efficacy and Toxicity XTT-Plates are stained and analyzed as previously described for the Dengue cytoprotection assay.

(13). Anti-Influenza Virus Cytoprotection Assay

Cell Preparation: MOCK cells (canine kidney cells, ATCC catalog#CCL-34) are passaged in DMEM supplemented with 10% FBS, 2 mM L-glutamine, 100 U/mL penicillin, 100 µg/mL streptomycin 1 mM sodium pyruvate, and 0.1 mM NEAA, in T-75 flasks prior to use in the antiviral assay. On the day preceding the assay, the cells are split 1:2 to assure they are in an exponential growth phase at the time of infection. Total cell and viability quantification is performed using a hemocytometer and Trypan Blue dye exclusion. Cell viability is greater than 95% for the cells to be utilized in the assay. The cells are resuspended at $1\times10^4$ cells per well in tissue culture medium and added to flat bottom microtiter plates in a volume of 100 µL. The plates are incubated at 37° C./5% $CO_2$ overnight to allow for cell adherence.

Virus Preparation: The influenza A/PR/8/34 (A TCC #VR-95), A/CA/05/09 (CDC), A/NY/18/09 (CDC) and A/NWS/33 (ATCC #VR-219) strains are obtained from ATCC or from the Center of Disease Control and are grown in MDCK cells for the production of stock virus pools. A pretitered aliquot of virus is removed from the freezer (−80° C.) and allowed to thaw slowly to room temperature in a biological safety cabinet. Virus is resuspended and diluted into assay medium (DMEM supplemented with 0.5% BSA, 2 mM L-glutamine, 100 U/mL penicillin, 100 µg/mL streptomycin, 1 mM sodium pyruvate, 0.1 mM NEAA, and 1 µg/ml TPCK-treated trypsin) such that the amount of virus added to each well in a volume of 100 µL is the amount determined to yield 85 to 95% cell killing at 4 days post-infection. Efficacy and Toxicity XTT-Plates are stained and analyzed as previously described for the Dengue cytoprotection assay.

(14). Anti-Hepatitis C Virus Assay

The HCV RNA replicon assay utilizes the cell line Huh7 ET (luc-ubi-neo/ET), which contains a HCV RNA replicon with a stable luciferase (LUC) reporter (Murray, M; Korba, B "Hepatitis C Virus Assays", http://niaid-aacf.org/protocols/HCV.htm). The LUC reporter is used as an indirect measure of HCV replication. The activity of the LUC reporter is directly proportional to HCV RNA levels and positive control antiviral compounds behave comparably using either LUC or RNA endpoints.

Cell Culture: The reporter cell line Huh-luc/neo-ET is obtained from Dr. Ralf Bartenschlager (Department of Molecular Virology, Hygiene Institute, University of Heidelberg, Germany) by ImQuest BioSciences through a specific licensing agreement. This cell line harbors the persistently replicating $I_{389}$ luc-ubi-neo/NS3-3'/ET replicon containing the firefly luciferase gene-ubiquitin-neomycin phosphotransferase fusion protein and EMCV IRES driven NS3-5B HCV coding sequences containing the ET tissueculture adaptive mutations (E 1202G, T12081, and K1846T). A stock culture of the Huh-luc/neo-ET is expanded by culture in DMEM supplemented with 10% FCS, 2 mM glutamine, penicillin (100 µU/mL)/streptomycin (100 µg/mL) and I X nonessential amino acids plus 1 mg/mL G418. The cells are split 1:4 and cultured for two passages in the same media plus 250 ug/mL G418. The cells are treated with trypsin and enumerated by staining with trypan blue and seeded into 96-well tissue culture plates at a cell culture density $7.5\times10^3$ cells per well and incubated at 37° C. 5% $CO_2$ for 24 hours. Following the 24 hour incubation, media is removed and replaced with the same media minus the G418 plus the test compounds in triplicate. Six wells in each plate received media alone as a no-treatment control. The cells are incubated an additional 72 hours at 37° C. 5% $CO_2$ then anti-HCV activity is measured by luciferase endpoint. Duplicate plates are treated and incubated in parallel for assessment of cellular toxicity by XTT staining.

Cellular Viability: The cell culture monolayers from treated cells are stained with the tetrazolium dye XTT to evaluate the cellular viability of the Huh-luc/neo-ET reporter cell line in the presence of the compounds.

Measurement of Virus Replication: HCV replication from the replicon assay system is measured by luciferase activity using the britelite plus luminescence reporter gene kit according to the manufacturer's instructions (Perkin Elmer, Shelton, Conn.). Briefly, one vial of britelite plus lyophilized substrate is solubilized in 10 mL of britelite reconstitution buffer and mixed gently by inversion. After 5 minute incubation at room temperature, the britelite plus reagent is added to the 96 well plates at 100 µL per well. The plates are sealed with adhesive film and incubated at room temperature for approximately 10 minutes to lyse the cells. The well contents are transferred to a white 96-well plate and luminescence is measured within 15 minutes using the Wallac 1450Microbeta Trilux liquid scintillation counter. The data are imported into a customized Microsoft Excel 2007 spreadsheet for determination of the 50% virus inhibition concentration (EC50).

The anti-HCV activity and toxicity of the exemplary compounds also can be tested in another two biological assays a cell-based HCV replicon assay and cytotoxicity assay which are described in WO 2007/027248.

(15). Anti-Parainfluenza-3 Cytoprotection Assay

Cell Preparation: HEp2 cells (human epithelial cells, ATCC catalog#CCL-23) are passaged in DMEM supplemented with 10% FBS, 2 mM L-glutamine, 100 U/mL penicillin, 100 µg/mL streptomycin 1 mM sodium pyruvate, and 0.1 mM NEAA, in T-75 flasks prior to use in the antiviral assay. On the day preceding the assay, the cells are split 1:2 to assure they are in an exponential growth phase at the time of infection. Total cell and viability quantification is performed using a hemocytometer and Trypan Blue dye exclusion. Cell viability is greater than 95% for the cells to be utilized in the assay. The cells are resuspended at $1\times10^4$ cells per well in tissue culture medium and added to flat bottom microtiter plates in a volume of 100 µL. The plates are incubated at 37° C./5% $CO_2$ overnight to allow for cell adherence.

Virus Preparation: The Parainfluenza virus type 3 SF4 strain is obtained from ATCC (catalog#VR-281) and is grown in HEp2 cells for the production of stock virus pools. A pretitered aliquot of virus is removed from the freezer (−80° C.) and allowed to thaw slowly to room temperature in a biological safety cabinet. Virus is resuspended and diluted into assay medium (DMEM supplemented with 2% heat-inactivated FBS, 2 mM L-glutamine, 100 U/mL penicillin, and 100 μg/mL streptomycin) such that the amount of virus added to each well in a volume of 100 μL is the amount determined to yield 85 to 95% cell killing at 6 days post-infection.

Plate Format: Each plate contains cell control wells (cells only), virus control wells (cells plus virus), triplicate drug toxicity wells per compound (cells plus drug only), as well as triplicate experimental wells (drug plus cells plus virus).

Efficacy and Toxicity XTT: Following incubation at 37° C. in a 5% $CO_2$ incubator, the test plates are stained with the tetrazolium dye XTT (2,3-bis(2-methoxy-4-nitro-5-sulfophenyl)-5-[(phenylamino)carbonyl]-2H-tetrazolium hydroxide). XTT-tetrazoliumis metabolized by the mitochondrial enzymes of metabolically active cells to a soluble formazan product, allowing rapid quantitative analysis of the inhibition of virus-induced cell killing by antiviral test substances. XTT solution is prepared daily as a stock of 1 mg/mL in RPMI1640. Phenazine methosulfate (PMS) solution is prepared at 0.15 mg/mL in PBS and stored in the dark at −20° C. XTT/PMS stock is prepared immediately before use by adding 40 μL of PMS per ml of XTT solution. Fifty microliters of XTT/PMS is added to each well of the plate and the plate is reincubated for 4 hours at 37° C. Plates are sealed with adhesive plate sealers and shaken gently or inverted several times to mix the soluble fomlazan product and the plate is read spectrophotometrically at 450/650 nm with a Molecular Devices Vmax platereader.

Data Analysis: Raw data is collected from the Softmax Pro 4.6 software and imported into a Microsoft Excel spreadsheet for analysis. The percent reduction in viral cytopathic effect compared to the untreated virus controls is calculated for each compound. The percent cell control value is calculated for each compound comparing the drug treated uninfected cells to the uninfected cells in medium alone.

(16). Influenza Polymerase Inhibition Assay

Virus Preparation: Purified influenza virus A/PR/8/34 (1 ml) is obtained from Advanced Biotechnologies, Inc. (Columbia, Md.), thawed and dispensed into five aliquots for storage at −80° C. until use. On the day of assay set up, 20 μL of 2.5% Triton N-101 is added to 180 μL of purified virus. The disrupted virus is diluted 1:2 in a solution containing 0.25% Triton and PBS. Disruption provided the source of influenza ribonucleoprotein (RNP) containing the influenza RNA-dependent RNA polymerase and template RNA. Samples are stored on ice until use in the assay.

Polymerase reaction: Each 50 μL polymerase reaction contained the following: 5 μL of the disrupted RNP, 100 mM Tris-HCl (pH 8.0), 100 mM KCl, 5 mM $MgCl_2$. 1 mM dithiothreitol, 0.25% Triton N-101, 5 μCi of [α-$^{32}$P] GTP, 100 μM ATP, 50 μM each (CTP, UTP), 1 μM GTP, and 200 μM adenyl (3'-5') guanosine. For testing the inhibitor, the reactions contained the inhibitor and the same is done for reactions containing the positive control (2'-Deoxy-2'-fluoroguanosine-5'-triphosphate (2-DFGTP)). Other controls included RNP+reaction mixture, and RNP+1% DMSO. The reaction mixture without the ApG primer and NTPs is incubated at 30° C. for 20 minutes. Once the ApG and NTPs are added to the reaction mixture, the samples are incubated at 30° C. for 1 hour then immediately followed by the transfer of the reaction onto glass-fiber filter plates and subsequent precipitation with 10% trichloroacetic acid (TCA). The plate is then washed five times with 5% TCA followed by one wash with 95% ethanol. Once the filter had dried, incorporation of [α-$^{32}$P] GTP is measured using a liquid scintillation counter (Micro beta).

Plate Format: Each test plate contained triplicate samples of the three compounds (6 concentrations) in addition to triplicate samples of RNP+reaction mixture (RNP alone), RNP+1% DMSO, and reaction mixture alone (no RNP).

Data Analysis: Raw data is collected from the Micro Beta scintillation counter. The incorporation of radioactive GTP directly correlates with the levels of polymerase activity. The "percent inhibition values" are obtained by dividing the mean value of each test compound by the RNP+1% DMSO control. The mean obtained at each concentration of 2DFGTP is compared to the RNP+reaction control. The data is then imported into Microsoft Excel spreadsheet to calculate the $IC_{50}$ values by linear regression analysis.

(17). HCV Polymerase Inhibition Assay

Activity of compounds for inhibition of HCV polymerase is evaluated using methods previously described (Lam et al. 2010. Antimicrobial Agents and Chemotherapy 54(8):3187-3196). HCV NS5B polymerase assays are performed in 20 μL volumes in 96 well reaction plates. Each reaction contained 40 ng/μL purified recombinant NS5BA22 genotype-1b polymerase, 20 ng/μL of HCV genotype-1b complimentary IRES template, 1 μM of each of the four natural ribonucleotides, 1 U/mL Optizyme RNAse inhibitor (Promega, Madison, Wis.), 1 mM $MgCl_2$, 0.75 mM $MnCl_2$, and 2 mM dithiothreitol (DTT) in 50 mM HEPES buffer (pH 7.5). Reaction mixtures are assembled on ice in two steps. Step 1 consisted of combining all reaction components except the natural nucleotides and labeled UTP in a polymerase reaction mixture. Ten microliters (10 μL) of the polymerase mixture is dispensed into individual wells of the 96 well reaction plate on ice. Polymerase reaction mixtures without NS5B polymerase are included as no enzyme controls. Serial half-logarithmic dilutions of test and control compounds, 2'-O-Methyl-CTP and 2'-O-Methyl-GTP (Trilink, San Diego, Calif.), are prepared in water and 5 uL of the serial diluted compounds or water alone (no compound control) are added to the wells containing the polymerase mixture. Five microliters of nucleotide mix (natural nucleotides and labeled UTP) is then added to the reaction plate wells and the plate is incubated at 27° C. for 30 minutes. The reactions are quenched with the addition of 80 uL stop solution (12.5 mM EDTA, 2.25M NaCl, and 225 mM sodium citrate) and the RNA products are applied to a Hybond-N+ membrane (GE Healthcare, Piscataway, N.J) under vacuum pressure using a dot blot apparatus. The membrane is removed from the dot blot apparatus and ished four times with 4×SSC (0.6M NaCl, and 60 mM sodium citrate), and then rinsed one time with water and once with 100% ethanol. The membrane is air dried and exposed to a phosphoimaging screen and the image captured using a Typhoon 8600 Phospho imager. Following capture of the image, the membrane is placed into a Micro beta cassette along with scintillation fluid and the CPM in each reaction is counted on a Micro beta 1450. CPM data are imported into a custom Excel spreadsheet for determination of compound $IC_{50}$s.

(18). Anti-HBV Assay

The anti-HBV activity of the compounds can be determined by treating the AD-38 cell line carrying wild type HBV under the control of tetracycline (see Ladner S. K., Otto M. J., Barker C. S., Zaifert K., Wang G. H., Guo J. T., Seeger C. & King R. W. *Antimicrob. Agents Chemother.* 1997, 41, 1715-20). Removal of tetracycline from the medium [Tet (−)] results in the production of HBV. The levels of HBV in the culture supernatant fluids from cells treated with the compounds can be compared with that of the untreated controls. Control cultures with tetracycline [Tet (+)] can also be maintained to determine the basal levels of HBV expression. 3TC can be included as positive control.

(19). Anti-HIV (in PBM cells) Assay

Anti-HIV-1 activity of the compounds is determined in human peripheral blood mononuclear (PBM) cells as described previously (see Schinazi R. F., McMillan A., Cannon D., Mathis R., Lloyd R. M. Jr., Peck A., Sommadossi J.-P., St. Clair M., Wilson J., Furman P. A., Painter G., Choi W.-B., Liotta D. C. Antimicrob. Agents Chemother. 1992, 36, 2423; Schinazi R. F., Sommadossi J.-P., Saalmann V., Cannon D., Xie M.-Y., Hart G., Smith G., Hahn E. Antimicrob. Agents Chemother. 1990, 34, 1061). Stock solutions (20-40 mM) of the compounds are prepared in sterile DMSO and then diluted to the desired concentration in growth medium. Cells are infected with the prototype $^{HIV-1}$LAI at a multiplicity of infection of 0.01. Virus obtained from the cell supernatant is quantified on day 6 after infection by a reverse transcriptase assay using $(rA)_n \cdot (dT)12-18$ as template-primer. The DMSO present in the diluted solution (<0.1%) had no effect on the virus yield. AZT is included as positive control. The antiviral $EC_{50}$ and $EC_{90}$ are obtained from the concentration-response curve using the median effective method described previously (see Chou T.-C. & Talalay P. *Adv. Enzyme Regul.* 1984, 22, 27-55; Belen'kii M. S. & Schinazi R. F. *Antiviral Res.* 1994, 25, 1-11).

(20). Assay for Bone Marrow Cytotoxicity

Primary human bone marrow mononuclear cells can be obtained commercially from Cambrex Bioscience (Walkersville, Md.). CFU-GM assays can be carried out using a bilayer soft agar in the presence of 50 units/mL human recombinant granulocyte/macrophage colony-stimulating factor, while BFU-E assays use a methylcellulose matrix containing 1 unit/mL erythropoietin (see Sommadossi J P, Carlisle R. Toxicity of 3'-azido-3'-deoxythymidine and 9-(1, 3-dihydroxy-2-propoxymethyl) guanine for normal human hepatopoietic progenitor cells in vitro. Antimicrob. Agents Chemother. 1987; 31: 452-454; Sommadossi, J P, Schinazi, R F, Chu, C K, and Xie, M Y. Comparison of Cytotoxicity of the (−) and (+) enantiomer of 2',3'-dideoxy-3'-thiacytidine in normal human bone marrow progenitor cells. Biochem. Pharmacol. 1992; 44:1921-1925). Each experiment is performed in duplicate in cells from three different donors. AZT can be used as a positive control. Cells can be incubated in the presence of the compound for 14-18 days at 37° C. with 5% $CO_2$, and colonies of greater than 50 cells can be counted using an inverted microscope to determine $IC_{50}$. The 50% inhibitory concentration ($IC_{50}$) can be obtained by least-squares linear regression analysis of the logarithm of drug concentration versus BFU-E survival fractions. Statistical analysis can be performed with Student's t test for independent non-paired samples.

In Vitro Anti-Cancer Activity-TC50 assays with human cancer cell lines.

Plating Cells: The Huh7, HEPG2, HEK293, MCF-7, PK9, RPK9, or BxPC3 cells are passaged when they are about 70% confluent. The cells are counted using a hemocytometer, and then diluted cells to $0.5 \times 10^5$ cells per mL in DMEM+10% FBS. 100 uL of the cells (5,000 cells) are plated per well in a clear 96-well plate. The cells are allowed to attach for 24 hours at 37° C.

Treating the cells: Pre-warm the DMEM media without phenol red+2% FBS media to 37° C. Dilute the 100 mM stocks of the gemcitabine analogs to 0.5 mM in DMEM without phenol red+2% FBS. This will bring the final DMSO concentration to 0.5%. Use these 0.5 mM dilutions to further serially dilute the drugs in DMEM without phenol red+2% FBS+0.5% DMSO. This will keep the concentration of DMSO in each condition identical. Remove the 96-well plate from the 37° C. incubator. Replace the media on the plate with the dilutions of the drugs. Stagger these treatments by 1 h and write the treatment time on each set of plates. Return to 37° C. for 48 h or 96 h as indicated.

The compounds can be tested using the MTS Assay: The reagents from CellTiter 96 kit (Promega Corporation, Madison, Wis.) are thawed at room temperature in the dark for 1 h. The 96-well plate is removed from the 37° C. incubator at 48 h after drug treatment. 20 uL of the combined MTS/PMS reagent to each well of the plate, mixed, and the plate returned to 37° C. The absorbance of each well at 490 nm and 650 nm is determined using the Flexstation 3 microplate reader in endpoint mode every hour for 3 h. The solutions in the wells are mixed prior to each reading. Fit Data to the Emax model: $y=(Emax \cdot x)/(TC_{50}+x)$, where Emax is the maximum inhibition and $TC_{50}$ is the inhibitory dose 50%. Alternatively, fit the data to the Emax sigmoidal model: $y=(Emax \cdot x^{slope})/(TC_{50}^{slope}+x^{slope})$, where slope is the Hill Slope.

Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Although the invention has been described with respect to various preferred embodiments, it is not intended to be limited thereto, but rather those skilled in the art will recognize that variations and modifications may be made therein which are within the spirit of the invention and the scope of the appended claims.

What is claimed is:

1. A compound represented by Formula (I):

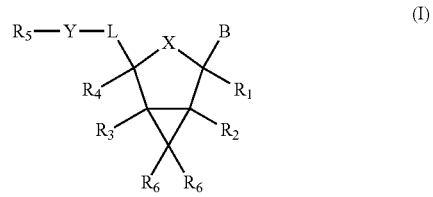

or a pharmaceutically acceptable salt thereof, wherein:
B is a nucleobase;
X is selected from the group consisting of: O, S, NH, NMe, $CH_2$, CHF, $CF_2$, $C=CH_2$, $C=CHF$, and $C=CF_2$;
$R_1$ and $R_4$ are each independently selected from the group consisting of: hydrogen, halogen, —CN, —$N_3$, and optionally substituted $C_1$-$C_4$ alkyl;
$R_2$ and $R_3$ are each independently selected from the group consisting of: hydrogen, OH, $OR_{11}$, halogen, —CN, —$N_3$, $NH_2$, $OC(O)R_{11}$, $OC(O)OR_{11}$, $OC(O)(NR_{11}R_{12})$, $N(R_{11})C(O)R_{11}$, $N(R_{11})C(O)OR_{11}$, $N(R_{11})C(O)(NR_{11}R12)$, $OP(O)(OR_{11})(OR_{12})$, $OP(O)(OR_{11})(NR_{11}R_{12})$, and $OP(O)(OR_{11})(NR_{11}R_{12})$; wherein at least one of $R_2$ and $R_3$ is not hydrogen; or alternatively, $R_2$ and $R_3$ are taken together with the carbon atoms to which they are attached to form a cyclic carbonate, optionally substituted cyclic carbamate, optionally substituted cyclic phosphate, optionally substituted cyclic phosphoramidate or optionally substituted cyclic phosphorodiamidate;

$R_{11}$ and $R_{12}$ at each occurrence are independently selected from the group consisting of: hydrogen, optionally substituted $C_1$-$C_{20}$ alkyl, and optionally substituted $C_2$-$C_{20}$ alkenyl; or alternatively, when they occur together $R_{11}$ and $R_{12}$ are taken together with the atoms to which they are attached and any intervening atoms to form a heterocyclic ring;

L is $CH_2$, CHMe or absent;

Y is O, $NR_{11}$, or $CH_2$;

$R_5$ is selected from the group consisting of: monophosphoryl, diphosphoryl, triphosphoryl, $C(O)R_{11}$, $C(O)OR_{11}$, $C(O)(NR_{11}R_{12})$, and $-(P(=Y^1)(-Y^2-R^x)(-Y^3))_n-R^y$; wherein n is 1, 2, or 3; $Y^1$ is O or S; $Y^2$ and $Y^3$ at each occurrence are each independently O, S, or NH; $R^x$ and $R^y$ at each occurrence are each independently selected from the group consisting of: hydrogen, optionally substituted $C_1$-$C_{20}$ alkyl, optionally substituted $C_2$-$C_{20}$ alkenyl, optionally substituted $C_3$-$C_8$ cycloalkyl, optionally substituted aryl, and optionally substituted heteroaryl; or alternatively $R^x$ and $R^y$ are taken together with the atoms to which they are attached to form a heterocyclic ring or ring system;

alternatively, $R_3$ and $R_5$ are taken together with the atoms to which they are attached to form $-P(=Y^1)(-Y^2-R^x)Y^4-$; wherein $Y^4$ is O or NH; and R6 at each occurrence is independently selected from the group consisting of hydrogen, halogen, and optionally substituted $C_1$-$C_4$ alkyl.

2. A compound of claim 1 represented by Formula (III):

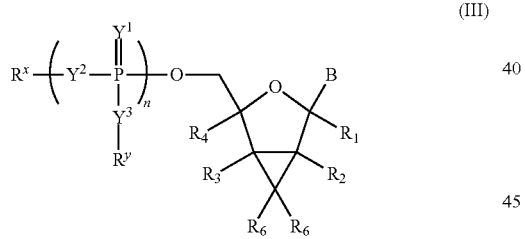

(III)

or a pharmaceutically acceptable salt thereof.

3. A compound of claim 1 represented by Formula (IIIa):

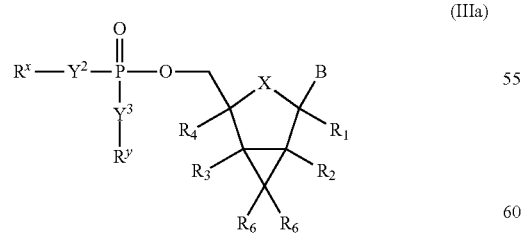

(IIIa)

or a pharmaceutically acceptable salt thereof.

4. A pharmaceutical composition comprising a compound or a combination of compounds according to claim 1 or a pharmaceutically acceptable salt thereof, in combination with a pharmaceutically acceptable carrier or excipient.

5. The pharmaceutical composition of claim 4, further comprising a compound selected from the group consisting of cytokines, protease inhibitors, antiviral agents, proteases, immunomodulators, caspase inhibitors, antibodies and polymerase inhibitors.

6. A method of inhibiting the replication of an RNA or DNA-containing virus comprising contacting said virus with a therapeutically effective amount of a compound or combination of compounds of claim 1, or a pharmaceutically acceptable salt thereof.

7. A method of preventing or treating abnormal cellular proliferation, a viral infection, or a symptom thereof in a subject in need thereof comprising administering to the subject a therapeutically effective amount of a compound or combination of compounds of claim 1, or a pharmaceutically acceptable salt thereof.

8. The method of claim 6, wherein the virus is human immunodeficiency virus (HIV), hepatitis C virus (HCV) or hepatitis B virus (HBV).

9. The compound of claim 3, represented by Formula (IIIb), (IIIc) or (IIId):

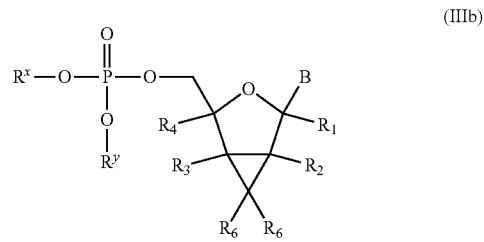

(IIIb)

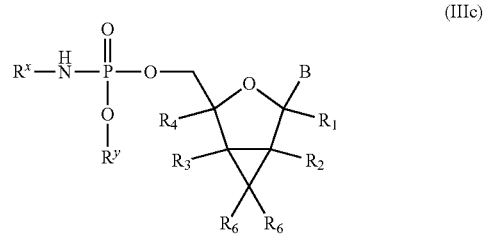

(IIIc)

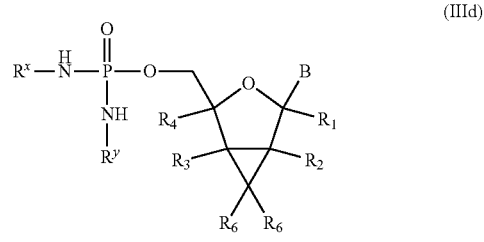

(IIId)

or a pharmaceutically acceptable salt thereof.

10. The compound of claim 3, represented by Formula (IIIe):

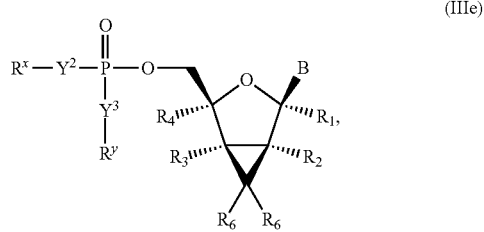

(IIIe)

or a pharmaceutically acceptable salt thereof.

11. The compound of claim 10, represented by Formula (IIIe1) to (IIIe9),

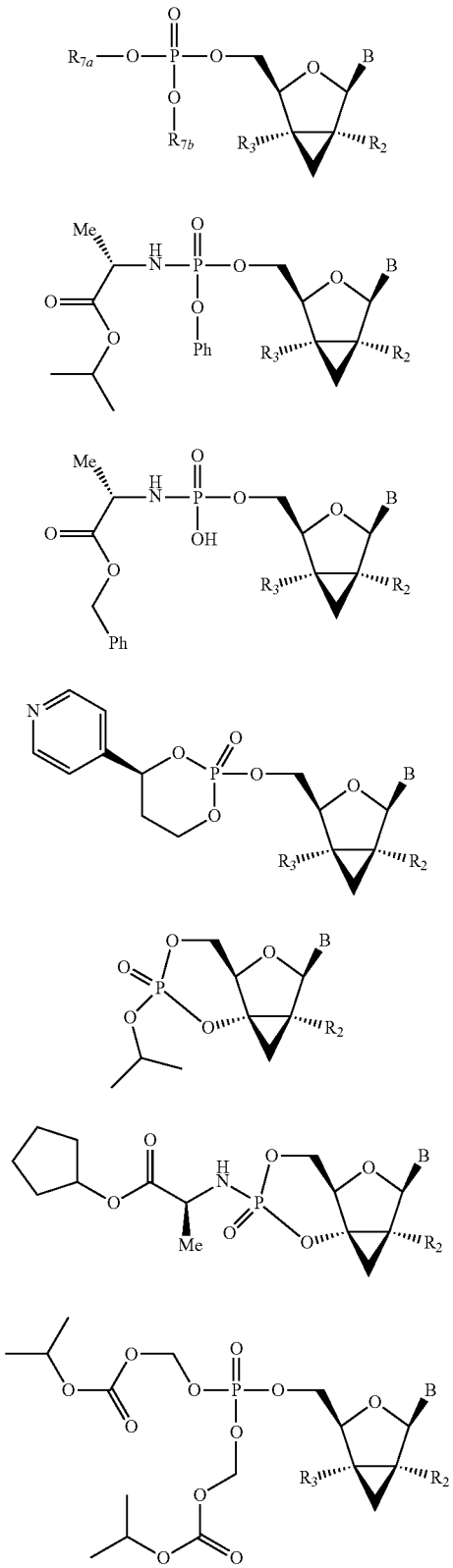

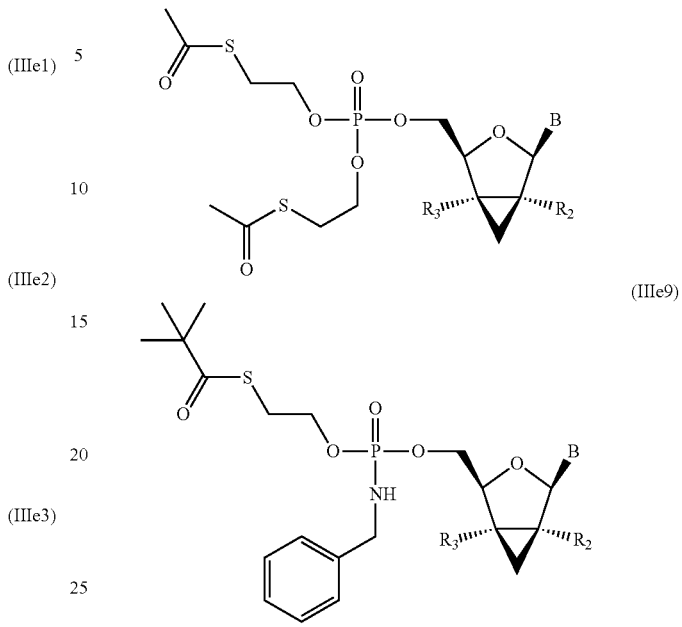

or a pharmaceutically acceptable salt thereof, wherein:
$R_{7a}$ and $R_{7b}$ are independently hydrogen or substituted or unsubstituted $C_1$-$C_{20}$ alkyl.

12. The compound of claim 1, wherein B is represented by Formula B1 or B2:

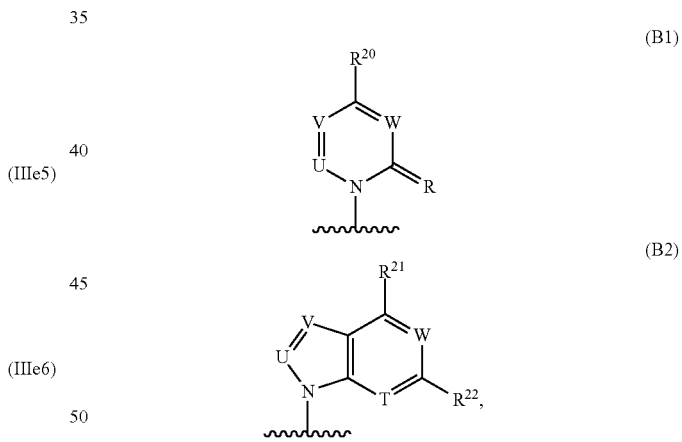

wherein:
R is selected from the group consisting of: O, S, $NR^x$, $NC(O)R^x$, $NC(O)OR^x$ and $NC(O)NR^xR^y$;
T, U, V and W are each independently N or $CR_{17}$; wherein $R_{17}$ at each occurrence is independently selected from a group consisting of: hydrogen, halogen, —CN, —C(O)$R^x$, —C(O)$NR^xR^y$, —NO$_2$, —N$_3$, —O$R^x$, —S$R^x$, —$NR^xR^y$, —OC(O)$R^x$, —OC(O)O$R^x$, —NHC(O)$R^x$, —NHC(O)O$R^x$ and —NHC(O)$NR^xR^y$, substituted or unsubstituted aryl, substituted or unsubstituted heteroaryl, substituted or unsubstituted heterocyclic, substituted or unsubstituted —$C_1$-$C_8$ alkyl, substituted or unsubstituted —$C_2$-$C_8$ alkenyl, substituted or unsubstituted —$C_2$-$C_8$ alkynyl;

$R^{20}$, $R^{21}$ and $R^{22}$ are each independently selected from the group consisting of: hydrogen, halogen, —CN, —C(O)R$^x$, —C(O)NR$^x$R$^y$, —NO$_2$, —N$_3$, —OR$^x$, —SR$^x$, —NR$^x$R$^y$, —OC(O)R$^x$, —OC(O)OR$^x$, —NHC(O)R$^y$, —NHC(O)OR$^x$ and —NHC(O)NR$^x$R$^y$, substituted or unsubstituted aryl, substituted or unsubstituted heteroaryl, substituted or unsubstituted heterocyclic, substituted or unsubstituted —C$_1$-C$_8$ alkyl, substituted or unsubstituted —C$_2$-C$_8$ alkenyl, substituted or unsubstituted —C$_2$-C$_8$ alkynyl.

13. The compound of claim 1, wherein B is represented by one of Formulas (B1a) to (B1r):

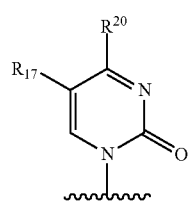
(B1a)

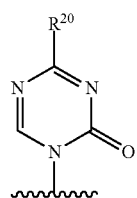
(B1b)

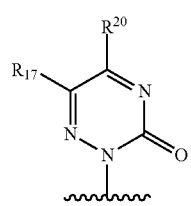
(B1c)

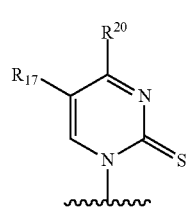
(B1d)

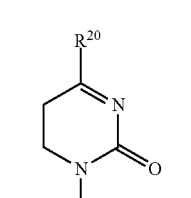
(B1e)

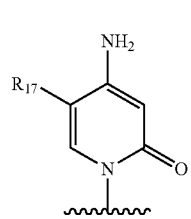
(B1f)

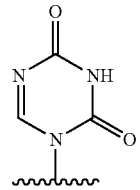
(B1g)

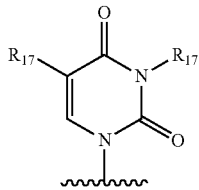
(B1h)

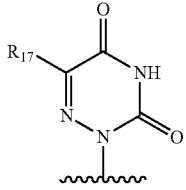
(B1i)

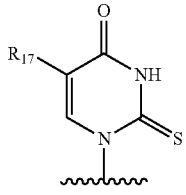
(B1j)

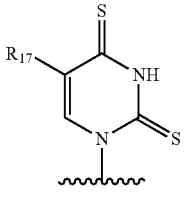
(B1k)

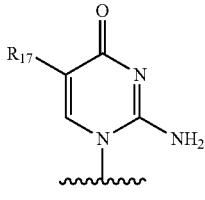
(B1l)

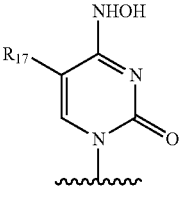
(B1m)

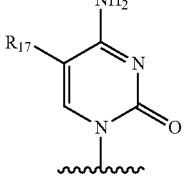
(B1n)

-continued

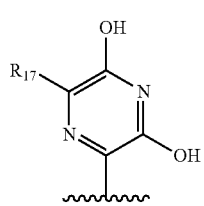
(B1o)

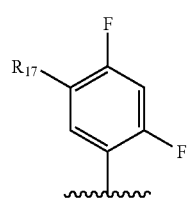
(B1p)

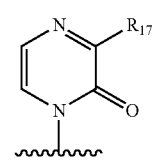
(B1q)

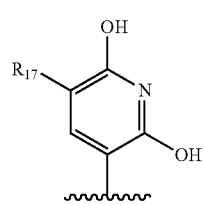
(B1r)

wherein:
R$_{17}$ at each occurrence is independently selected from a group consisting of: hydrogen, halogen, —CN, —C(O)R$^x$, —C(O)NR$^x$R$^y$, —NO$_2$, —N$_3$, —OR$^x$, —SR$^x$, —NR$^x$R$^y$, —OC(O)R$^x$, —OC(O)OR$^x$, —NHC(O)R$^x$, —NHC(O)OR$^x$ and —NHC(O)NR$^x$R$^y$, substituted or unsubstituted aryl, substituted or unsubstituted heteroaryl, substituted or unsubstituted heterocyclic, substituted or unsubstituted —C$_1$-C$_8$ alkyl, substituted or unsubstituted —C$_2$-C$_8$ alkenyl, substituted or unsubstituted —C$_2$-C$_8$ alkynyl; and R$^{20}$ is selected from the group consisting of: hydrogen, halogen, —CN, —C(O)R$^x$, —C(O)NR$^x$R$^y$, —NO$_2$, —N$_3$, —OR$^x$, —SR$^x$, —NR$^x$R$^y$, —OC(O)R$^x$, —OC(O)OR$^x$, —NHC(O)R$^y$, —NHC(O)OR$^x$ and —NHC(O)NR$^x$R$^y$, substituted or unsubstituted aryl, substituted or unsubstituted heteroaryl, substituted or unsubstituted heterocyclic, substituted or unsubstituted —C$_1$-C$_8$ alkyl, substituted or unsubstituted —C$_2$-C$_8$ alkenyl, substituted or unsubstituted —C$_2$-C$_8$ alkynyl.

14. The compound of claim 1, wherein B is represented by one of Formulas (B2a) to (B2o):

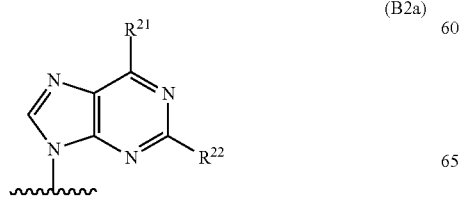
(B2a)

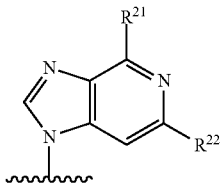
(B2b)

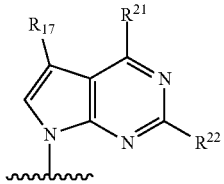
(B2c)

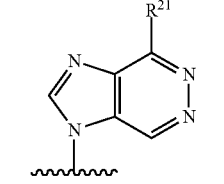
(B2d)

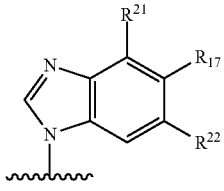
(B2e)

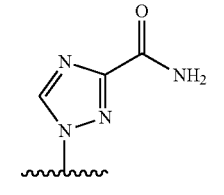
(B2f)

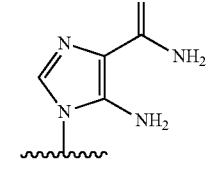
(B2g)

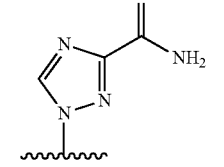
(B2h)

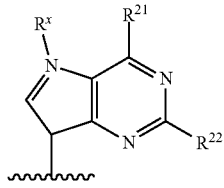
(B2i)

-continued

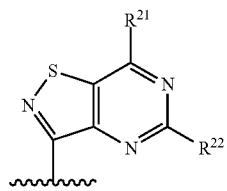
(B2j)

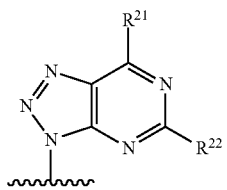
(B2k)

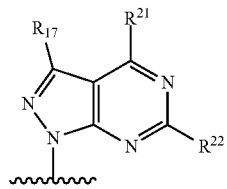
(B2l)

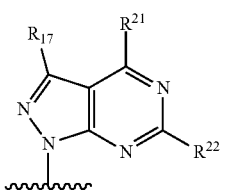
(B2m)

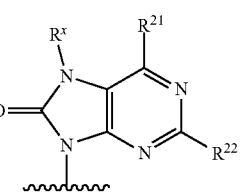
(B2n)

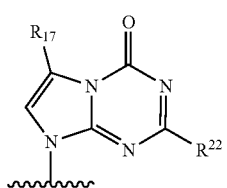
(B2o)

wherein:
$R_{17}$ at each occurrence is independently selected from a group consisting of: hydrogen, halogen, —CN, —C(O)$R^x$, —C(O)N$R^xR^y$, —NO$_2$, —N$_3$, —O$R^x$, —S$R^x$, —N$R^xR^y$, —OC(O)$R^x$, —OC(O)O$R^x$, —NHC(O)$R^x$, —NHC(O)O$R^x$ and —NHC(O)N$R^xR^y$, substituted or unsubstituted aryl, substituted or unsubstituted heteroaryl, substituted or unsubstituted heterocyclic, substituted or unsubstituted —C$_1$-C$_8$ alkyl, substituted or unsubstituted —C$_2$-C$_8$ alkenyl, substituted or unsubstituted —C$_2$-C$_8$ alkynyl; and $R^{21}$ and $R^{22}$ are independently selected from the group consisting of: hydrogen, halogen, —CN, —C(O)$R^x$, —C(O)N$R^xR^y$, —NO$_2$, —N$_3$, —O$R^x$, —S$R^x$, —N$R^xR^y$, —OC(O)$R^x$, —OC(O)O$R^x$, —NHC(O)$R^y$, —NHC(O)O$R^x$ and —NHC(O)N$R^xR^y$, substituted or unsubstituted aryl, substituted or unsubstituted heteroaryl, substituted or unsubstituted heterocyclic, substituted or unsubstituted —C$_1$-C$_8$ alkyl, substituted or unsubstituted —C$_2$-C$_8$ alkenyl, substituted or unsubstituted —C$_2$-C$_8$ alkynyl.

15. The compound of claim 12, wherein B is represented by one of Formulas (B3a) to (B3j):

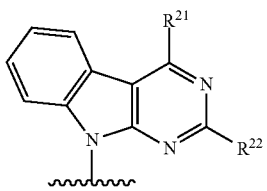
(B3a)

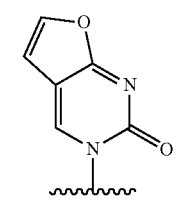
(B3b)

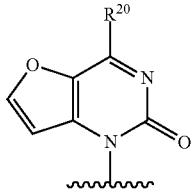
(B3c)

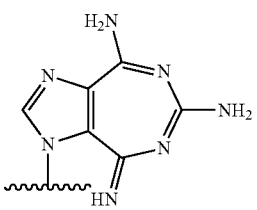
(B3d)

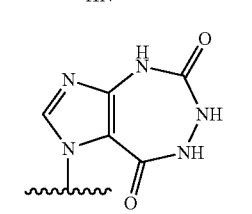
(B3e)

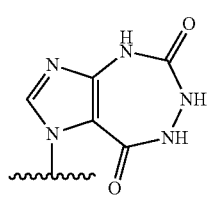
(B3f)

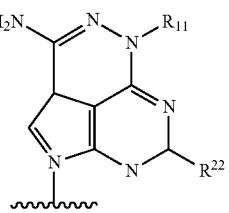
(B3g)

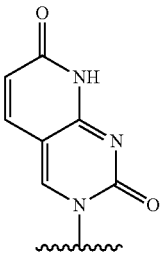

87
-continued

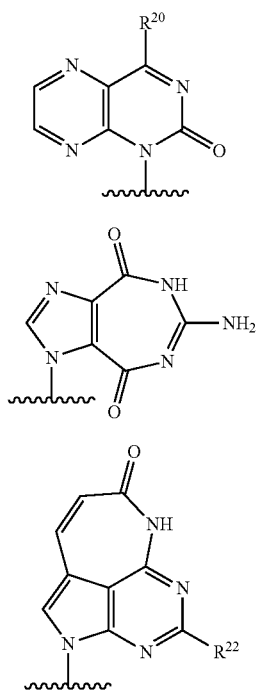

(B3h)

(B3i)

(B3j)

wherein:
R²⁰, R²¹ and R²² are each independently selected from the group consisting of: hydrogen, halogen, —CN, —C(O)ˣ, —C(O)NRˣRʸ, —NO₂, —N₃, —ORˣ, —SR', —NRˣRʸ, —OC(O)Rˣ, —OC(O)ORˣ, —NHC(O)Rˣ, —NHC(O)ORˣ and —NHC(O)NRˣRʸ, substituted or unsubstituted aryl, substituted or unsubstituted heteroaryl, substituted or unsubstituted heterocyclic, substituted or unsubstituted —C₁-C₈ alkyl, substituted or unsubstituted —C₂-C₈ alkenyl, substituted or unsubstituted —C₂-C₈ alkynyl.

16. The compound of claim 1, wherein X is O.

17. A compound selected from the compounds set forth in the table below, or a pharmaceutically acceptable salt thereof:

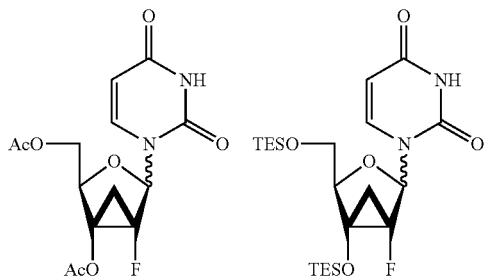

88
-continued

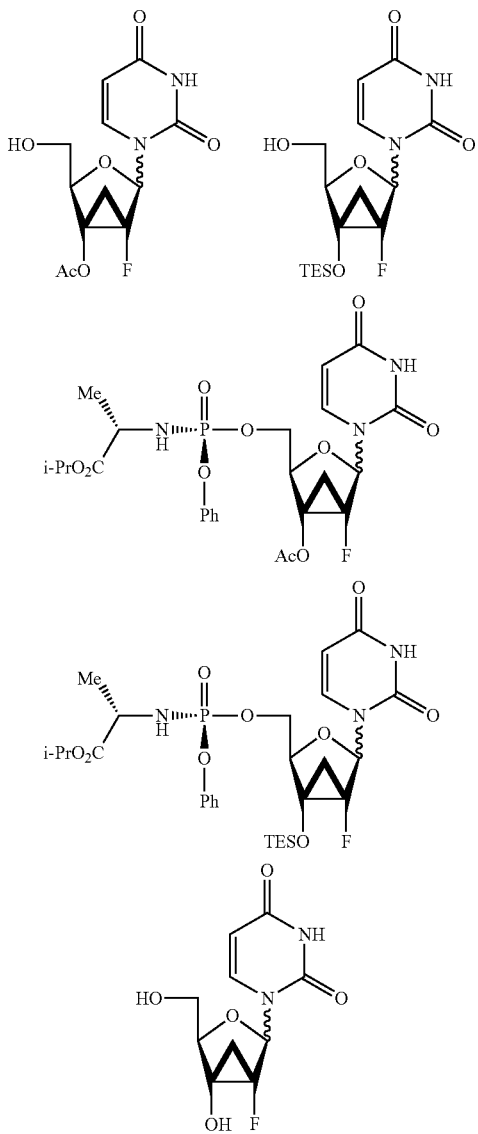

* * * * *

UNITED STATES PATENT AND TRADEMARK OFFICE
CERTIFICATE OF CORRECTION

PATENT NO. : 9,675,632 B2
APPLICATION NO. : 14/836157
DATED : June 13, 2017
INVENTOR(S) : Yao-Ling Qiu et al.

It is certified that error appears in the above-identified patent and that said Letters Patent is hereby corrected as shown below:

In the Claims

At Column 77

In Claim 3, Lines 52 through 60, delete " 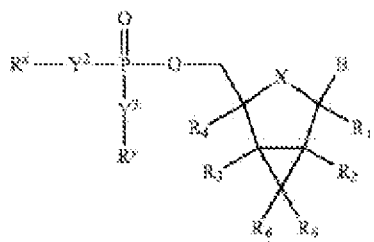 " and insert

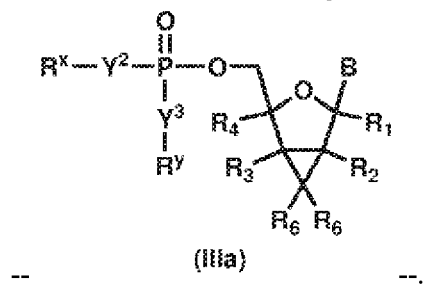

--                                     --.

Signed and Sealed this
Tenth Day of October, 2017

Joseph Matal
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 9,675,632 B2

At Column 82

In Claim 13, Lines 35 through 41, delete " 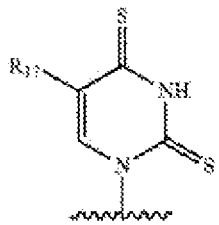 " and insert -- 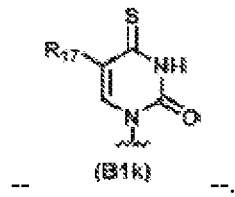 --.

At Column 87
In Claim 15, Line 33, delete "–SR'" and insert -- –SR$^x$ --.